US006689778B2

(12) United States Patent
Bemis et al.

(10) Patent No.: US 6,689,778 B2
(45) Date of Patent: Feb. 10, 2004

(54) INHIBITORS OF SRC AND LCK PROTEIN KINASES

(75) Inventors: Guy Bemis, Arlington, MA (US); Huai Gao, Natick, MA (US); Edmund Harrington, South Boston, MA (US); Francesco Salituro, Marlboro, MA (US); Jian Wang, Boston, MA (US); Mark Ledeboer, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/171,895

(22) Filed: Jun. 14, 2002

(65) Prior Publication Data

US 2003/0171389 A1 Sep. 11, 2003

Related U.S. Application Data

(60) Provisional application No. 60/302,969, filed on Jul. 3, 2001.

(51) Int. Cl.[7] .................... C07D 413/04; C07D 413/14; A61K 31/422

(52) U.S. Cl. .............................. 514/235.8; 514/252.19; 514/275; 544/122; 544/331

(58) Field of Search ................................ 544/122, 331; 514/235.8, 252.19, 275

(56) References Cited

FOREIGN PATENT DOCUMENTS

WO WO 01/12621 2/2001

OTHER PUBLICATIONS

Casanova et al., PubMed Abstract [Rev. Neurol. 28(9):909–15], May 1999.*

Simone, Oncology: Introduction, Cecil Textbook of Medicine, 20th Edition, vol. 1, pp. 1004–1010, 1996.*

Traxler, Review: Oncologic, Endocrine & Metabolic. Protein Tyrosine kinase inhibitors in cancer treatment, Exp. Opin. Ther. Patents, 7(6), pp. 571–588, 1997.*

Bolen, J.B., "Expression and Interactions of the Src Family of Tyrosine Protein Kinases in T Lymphocytes," *Advances in Cancer Research*, 57:103–149 (1991).

* cited by examiner

*Primary Examiner*—Deepak Rao
(74) *Attorney, Agent, or Firm*—Andrea L. C. Robidoux; Vertex Pharmaceuticals Incorporated

(57) ABSTRACT

The present invention provides compounds of formula I:

I

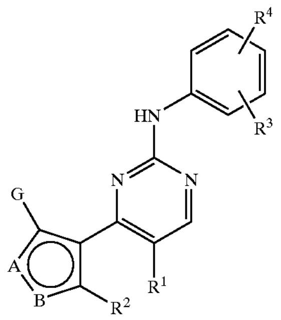

or a pharmaceutically acceptable derivative thereof, wherein A—B is N—O or O—N and G, $R^1$, $R^2$, $R^3$, and $R^4$ are as described in the specification. These compounds are inhibitors of protein kinase, particularly inhibitors of Src and Lck kinase. The invention also provides pharmaceutical compositions comprising the inhibitors of the invention and methods of utilizing those compositions in the treatment and prevention of various disorders.

17 Claims, No Drawings

INHIBITORS OF SRC AND LCK PROTEIN KINASES

CROSS REFERENCE TO RELATED APPLICATION

This application claims priority to U.S. Provisional Patent Application No. 60/302,969 filed Jul. 3, 2001, the contents of which are incorporated herein by reference.

TECHNICAL FIELD OF INVENTION

The present invention relates to inhibitors of kinases belonging to the Src family of protein kinases, especially Src and Lck protein kinases. Src kinases are implicated in cancer, immune disorders and bone diseases. The invention also provides pharmaceutical compositions comprising the inhibitors of the invention and methods of utilizing those compositions in the treatment and prevention of various disorders.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

One kinase family of particular interest is the Src family of kinases. These kinases are implicated in cancer, immune system dysfunction and bone remodeling diseases. For general reviews, see Thomas and Brugge, *Annu. Rev. Cell Dev. Biol.* (1997) 13, 513; Lawrence and Niu, *Pharmacol. Ther.* (1998) 77, 81; Tatosyan and Mizenina, *Biochemistry* (Moscow) (2000) 65, 49; Boschelli et al., *Drugs of the Future* 2000, 25(7), 717, (2000).

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 65, 49–58 (2000).

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell,* 69, 551 (1992) and Soriano et al., *Cell,* 64, 693 (1991).

Suppression of arthritic bone destruction has been achieved by the overexpression of CSK in rheumatoid synoviocytes and osteoclasts. Takayanagi et al., *J. Clin. Invest.,* 104, 137 (1999). CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717, (2000).

Src also plays a role in the replication of hepatitis B virus. The virally encoded transcription factor HBx activates Src in a step required for propagation of the virus. Klein et al., *EMBO J.,* 18, 5019, (1999) and Klein et al., *Mol.Cell. Biol.,* 17, 6427 (1997).

A number of studies have linked Src expression to cancers such as colon, breast, hepatic and pancreatic cancer, certain B-cell leukemias and lymphomas. Talamonti et al., *J. Clin. Invest.,* 91, 53 (1993); Lutz et al., *Biochem. Biophys. Res.* 243, 503 (1998); Rosen et al., *J. Biol. Chem.,* 261, 13754 (1986); Bolen et al., *Proc. Natl. Acad. Sci. USA,* 84, 2251 (1987); Masaki et al., *Hepatology,* 27, 1257 (1998); Biscardi et al., *Adv. Cancer Res.,* 76, 61 (1999); Lynch et al., *Leukemia,* 7, 1416 (1993); Furthermore, antisense Src expressed in ovarian and colon tumor cells has been shown to inhibit tumor growth. Wiener et al., *Clin. Cancer Res.,* 5, 2164 (1999); Staley et al., *Cell Growth Diff.,* 8, 269 (1997).

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature,* 357, 161 (1992). Hck, Fgr and Lyn have been identified as important mediators of integrin signaling in myeloid leukocytes. Lowell et al., *J. Leukoc. Diol.,* 65, 313 (1999). Inhibition of these kinase mediators may therefore be useful for treating inflammation. Boschelli et al., *Drugs of the Future* 2000, 25(7), 717, (2000).

There is a high unmet medical need to develop new therapeutic agents that are useful in treating the aforementioned conditions associated with Src and Lck kinase activation, especially considering the currently available, relatively inadequate treatment options for the majority of these conditions.

SUMMARY OF THE INVENTION

It has now been found that compounds of this invention, and pharmaceutically acceptable compositions thereof, are effective as inhibitors of Src and Lck protein kinases. These compounds have the formula I:

I

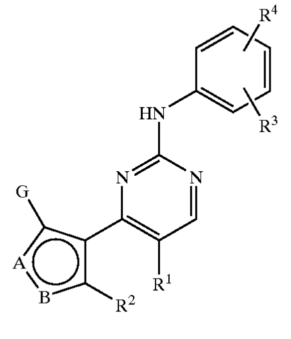

or a pharmaceutically acceptable derivative thereof, wherein A, B, G, $R^1$, $R^2$, $R^3$, and $R^4$ are as defined below.

These compounds, and pharmaceutically acceptable compositions thereof, are useful for treating or lessening the severity of a variety of disorders including hypercalcemia, osteoporosis, osteoarthritis, cancer, symptomatic treatment of bone metastasis, Paget's disease, autoimmune diseases such as transplant rejection, allergies, rheumatoid arthritis, and leukemia.

DETAILED DESCRIPTION OF THE INVENTION

The present invention relates to a compound of formula I:

I

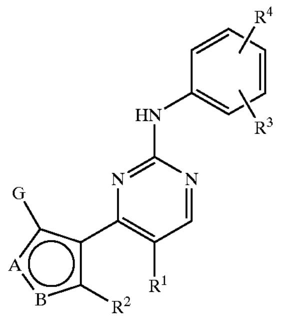

or a pharmaceutically acceptable derivative thereof, wherein:

A—B is N—O or O—N;

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), $C(O)CH_2C(O)$, C(O)C(O, C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

$R^3$ is selected from $ZQ_nR^5$ or $ZQ_nR^7$, wherein $ZQ_nR^7$ is not hydrogen;

Q is an optionally substituted $C_1$–$C_6$ alkylidene chain wherein:

one or two non-adjacent methylene units of Q are optionally and independently replaced by O, NR, NRC(O), C(O)NR, C(O), S, SO, $SO_2$, or $SO_2NR$; provided that said optionally replaced methylene unit of Q is a methylene unit non-adjacent to $R^7$;

each n is independently selected from zero or one;

Z is selected from a valence bond, O, S, SO, $SO_2$, NH, C(O), C(O)NH, NHC(O), $SO_2NH$, or $NHSO_2$;

$R^4$ is selected from R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, or:

two $R^4$ on adjacent positions of the phenyl ring are taken together to form a saturated, partially unsaturated, or fully unsaturated 5–7 membered ring having 0–3 heteroatoms independently selected from nitrogen, oxygen, or sulfur;

$R^5$ is $Ar^1$, wherein $R^5$ is optionally substituted with up to three $R^6$;

each $R^6$ is independently selected from R, halogen, $NO_2$, CN, OR, SR, $N(R)_2$, NRC(O)R, $NRC(O)N(R)_2$, $NRCO_2R$, C(O)R, $CO_2R$, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, or:

two $R^6$ on adjacent positions of $R^5$ are taken together to form a saturated, partially unsaturated, or fully unsaturated 5–7 membered ring having 0–3 heteroatoms independently selected from nitrogen, oxygen, or sulfur; and $R^7$ is selected from R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$;

provided that:

(a) when $R^3$ is $ZQR^7$, $R^1$ is other than hydrogen, and (b) when $R^1$ is hydrogen, $R^5$ is other than phenyl.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched $C_1$–$C_8$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation, and includes aryl rings.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —$R^o$, —$OR^o$, —$SR^o$, 1,2-methylene-dioxy, 1,2-ethylenedioxy, phenyl (Ph) optionally substituted with $R^o$, —O(Ph) optionally substituted with $R^o$, —$CH_2$(Ph) optionally substituted with $R^o$, —$CH_2CH_2$(Ph), optionally substituted with $R^o$, a 5–6 membered heteroaryl or heterocyclic ring optionally substituted with $R^o$, —$NO_2$, —CN, —$N(R^o)_2$, —$NR^oC(O)R^o$, —$NR^oC(O)N(R^o)_2$, —$NR^oCO_2R^o$, —$NR^oNR^oC(O)R^o$, —$NR^oNR^oC(O)N(R^o)_2$, —$NR^oNR^oCO_2R^o$, —$C(O)C(O)R^o$, —$C(O)CH_2C(O)R^o$, —$CO_2R^o$, —$C(O)R^o$, —$C(O)N(R^o)_2$, —$OC(O)N(R^o)_2$, —$S(O)_2R^o$, —$SO_2N(R^o)_2$, —$S(O)R^o$, —$NR^oSO_2N(R^o)_2$, —$NR^oSO_2R^o$, —$C(=S)N(R^o)_2$, —$C(=NH)—N(R^o)_2$, or —$(CH_2)_yNHC(O)R^o$, wherein each $R^o$ is independently selected from hydrogen, optionally substituted $C_{1-6}$ aliphatic, phenyl, —O(Ph), or —$CH_2$(Ph). Optional substituents on the aliphatic group of $R^o$ are selected from $NH_2$, $NH(C_{1-4}$ aliphatic), $N(C_{1-4}$ aliphatic$)_{21}$ halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =$NNHR^*$, =$NN(R^*)_2$, =$NNHC(O)R^*$, =$NNHCO_2$(alkyl), =$NNHSO_2$(alkyl), or =$NR^*$, where each $R^*$ is independently selected from hydrogen or an optionally substituted $C_{1-6}$ aliphatic. Optional substituents on the aliphatic group of $R^*$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo ($C_{1-4}$ aliphatic).

Optional substituents on the nitrogen of a non-aromatic heterocyclic ring are selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^+)_2$, —$C(=NH)—N(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$CH_2CH_2$(Ph), or an unsubstituted 5–6 membered heteroaryl or heterocyclic ring. Optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic).

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention. Such compounds are useful, for example, as analytical tools or probes in biological assays.

According to one embodiment, the present invention relates to a compound of formula Ia or Ib:

Ia

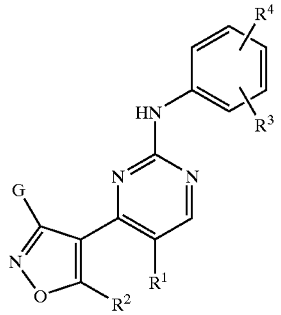

-continued

Ib

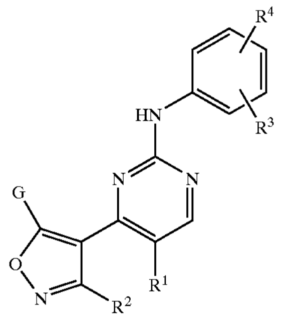

or a pharmaceutically acceptable derivative thereof, wherein G, $R^1$, $R^2$, $R^3$, and $R^4$ are as described above.

Preferred G groups of formulae Ia and Ib are selected from $X_mR$ or $X_mAr^1$, wherein each X, when present, is O, S, or NH, R is a $C_{1-4}$ aliphatic, and $Ar^1$ is an optionally substituted 5–6 membered saturated or aryl ring having 0–2 heteroaroms independently selected from nitrogen, oxygen, or sulfur. More preferred G groups of formulae Ia and Ib are selected from S-phenyl, O-phenyl, OMe, or an optionally substituted cyclohexyl, phenyl, piperidinyl, piperazinyl, pyrrolidinyl, morpholinyl, thiomorpholinyl, or pyridyl ring. Preferred substituents on the G group include $R^o$, $OR^o$, $C(O)N(R^o)_2$, $C(O)R^o$, and $C(O)OR^o$.

Preferred $R^2$ groups of formulae Ia and Ib are selected from R wherein R is an optionally substituted $C_{1-4}$ aliphatic group. More preferred $R^2$ groups of formulae Ia and Ib are selected from methyl, ethyl, propyl, isopropyl, cyclopropyl, or t-butyl.

Preferred $R^1$ groups of formulae Ia and Ib are selected from R, $T_yR$, or TCN, wherein each T is independently selected from a $C_{1-4}$ alkylidene chain wherein one methylene unit of T is replaced by O, C(O), C(O)O, C(O)NH, NH, or S, and each R is independently selected from hydrogen or an optionally substituted $C_{1-4}$ aliphatic. More preferred $R^1$ groups of formulae Ia and Ib are selected from hydrogen, methyl, ethyl, cyclopropyl, $CH_2CN$, $CO_2CH_3$, $OCH_3$, $CH_2OCH_3$, $CO_2H$, $C(O)NH_2$, $NH_2$, OH, $CH_2OCH_2CH_2CH_3$, and $CH_2OH$.

Preferred $R^4$ groups, when present in compounds of formulae Ia and Ib, are selected from R, OR, CN, halogen, and $N(R)_2$. More preferred $R^4$ groups, when present in compounds of formulae Ia and Ib, are selected from hydrogen, methyl, ethyl, t-butyl, propyl, isopropyl, cyclopropyl, $CF_3$, $CH_2F$, OH, $OCH_3$, chloro, fluoro, iodo, $NH_2$, $NHCH_3$, and $N(CH_3)_2$.

Preferred Z groups of formulae Ia and Ib are selected from a valence bond, O, NH, S, or NHC(O).

Preferred Q groups of formula formulae Ia and Ib, when present, are selected from a $C_{1-6}$ alkylidene chain wherein one or two non-adjacent methylene units of Q are optionally and independently replaced by O, NR, S, or C(O). More preferred Q groups of formulae Ia and Ib are selected from $-CH_2-$, $-CH_2CH_2-$, $-CH_2CH_2CH_2-$, $-CH_2CH_2CH_2CH_2-$, $-CH_2O-$, $-CH_2NR-$, $-CH_2CH_2O-$, $-CH_2CH_2NR-$, $-CH_2CH_2CH_2O-$, $-CH_2CH_2CH_2NR-$, $-CH_2CH_2CH_2CH_2O-$, $-CH_2CH_2CH_2CH_2NR-$, $-CH_2CH_2OCH_2CH_2-$, $-(CH_2)_4NHCH_2-$, $-(CH_2)_3NHCH_2CH_2-$, or $-CH_2CH_2NHCH_2CH_2-$.

Preferred $R^5$ groups of formulae Ia and Ib are selected from a 5–6 membered saturated or aryl ring having 0–2 heteroatoms independently selected from nitrogen, oxygen, or sulfur, wherein said ring is optionally substituted with up to two $R^6$ groups.

More preferred $R^5$ groups of formulae Ia and Ib are selected from optionally substituted tetrahydropyranyl, pyrrolidinyl, piperidinyl, piperazinyl, morpholinyl, thiomorpholinyl, pyridinyl, phenyl, or cyclohexyl. Preferred $R^6$ substituents on the $R^5$ ring, when present, are selected from R, OR, or $N(R)_2$. More preferred $R^6$ substituents on the $R^5$ ring are OH, $CH_2OH$, $CH_2CH_2OH$, and $CH_2CH_3$.

Preferred $R^7$ groups of formula Ia and Ib are selected from OR, $N(R)_2$, OC(O)R, $CO_2R$, $C(O)N(R)_2$, NRC(O)OR, and NRC(O)R. More preferred $R^7$ groups of formulae Ia and Ib are selected from OH, $OCH_3$, $NH_2$, $N(CH_3)_2$, $N(CH_2CH_3)_2$, $OC(O)CH_3$, $CO_2H$, $C(O)NH_2$, $NHCH_2CH_2OH$, $NHCH_2CH_2OCH_3$, $NHCH_2CH_2CH_2OH$, $N(CH_3)CH_2CH_2OH$, $NHCO_2$t-butyl, $CO_2CH_3$, $NHC(O)CH_3$, and $CH_2CH_2NHC(O)CH_3$.

Another embodiment of this invention relates to a compound of formula II:

II

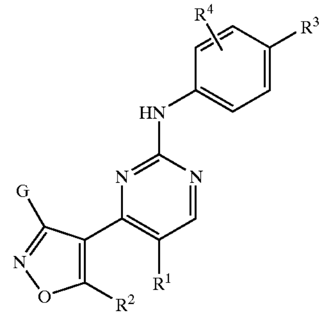

or a pharmaceutically acceptable derivative thereof, wherein G, $R^1$, $R^2$, $R^3$, and $R^4$ are as defined above.

Preferred G, $R^1$, $R^2$, and $R^4$ groups of formula II are those described for compounds of formulae Ia and Ib above.

Preferred $R^3$ groups of formula II are those wherein Z is a valence bond and Q is a $C_1$–$C_3$ alkylidene chain. Preferred $R^5$ and $R^7$ groups of $R^3$ of formula II are as described for compounds of formulae Ia and Ib above.

Exemplary structures of formula II are set forth in Table 1 below.

TABLE 1
Compounds of Formula II
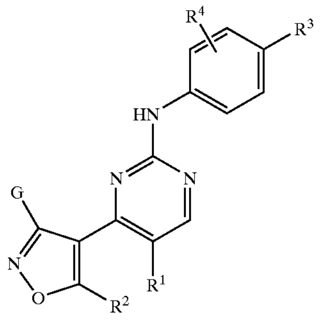
II
| No. | $R^1$ | 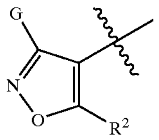 | 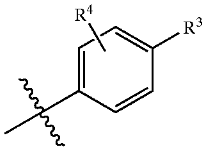 |
|---|---|---|---|
| II-1 | $CH_3$ | 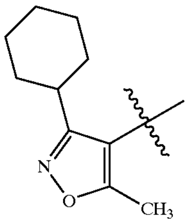 | 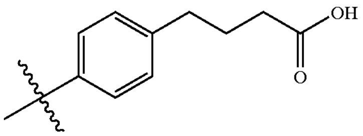 |
| II-2 | $CH_3$ | 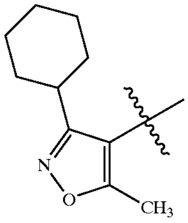 | 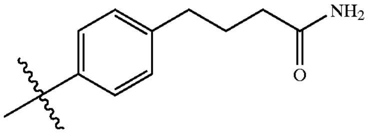 |
| II-3 | $CH_3$ | 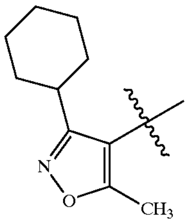 | 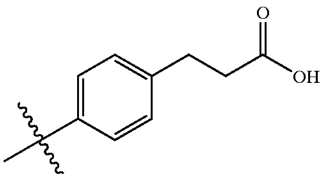 |
| II-4 | $CH_3$ | 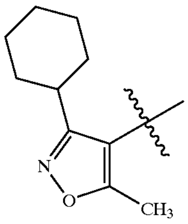 | 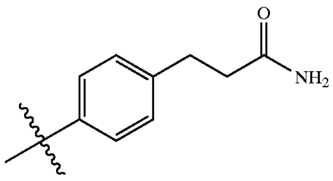 |

TABLE 1-continued
Compounds of Formula II
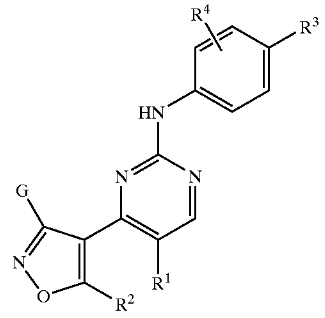
II
| No. | $R^1$ | 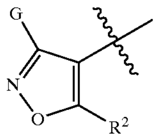 | 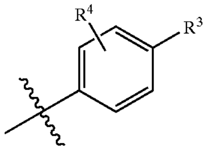 |
|---|---|---|---|
| II-5 | $CH_3$ | 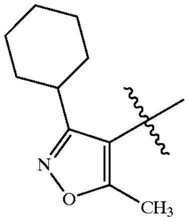 | 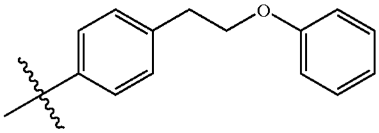 |
| II-6 | $CH_2CN$ | 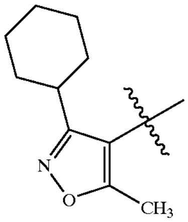 | 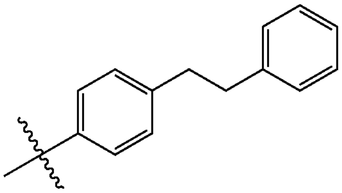 |
| II-7 | COOH | 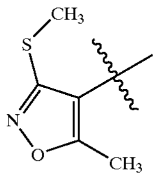 | 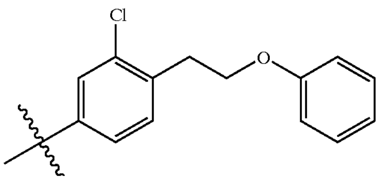 |
| II-8 | H | 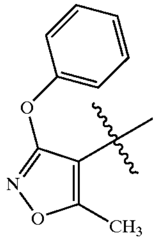 | 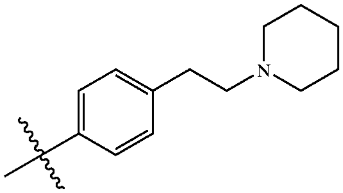 |

TABLE 1-continued

Compounds of Formula II

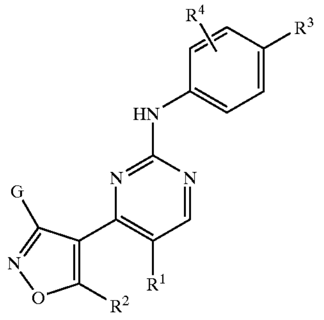

II

| No. | $R^1$ | 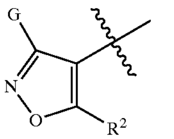 | 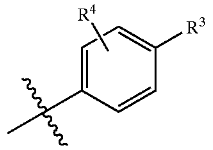 |
|---|---|---|---|
| II-9 | $CH_2CH_3$ | 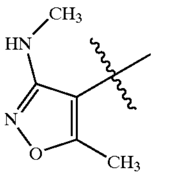 | 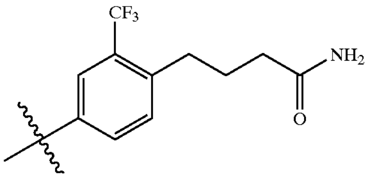 |
| II-10 | $C(O)NH_2$ | 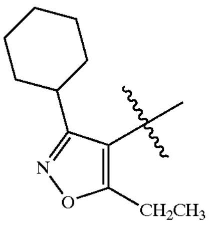 | 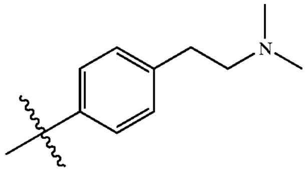 |

According to a preferred embodiment, the present invention relates to a compound of formula IIIa or IIIb:

IIIa

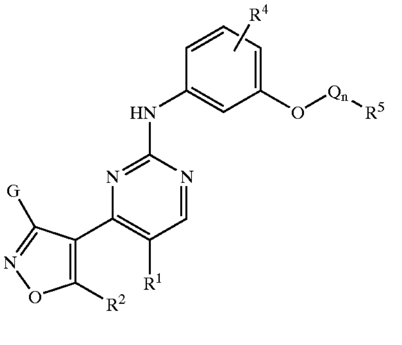

-continued

IIIb

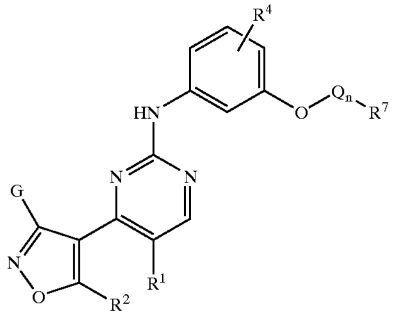

or a pharmaceutically acceptable derivative thereof, wherein G, Q, n, $R^1$, $R^2$, $R^4$, $R^5$, and $R^7$ are as defined above.

Preferred G. Q, n, $R^1$, $R^2$, $R^4$, $R^5$, and $R^7$ groups of formulae IIIa and IIIb are those described for compounds of formula Ia and Ib above.

Exemplary structures of formula IIIa are set forth in Table 2 below.

TABLE 2
Compounds of Formula IIIa
IIIa
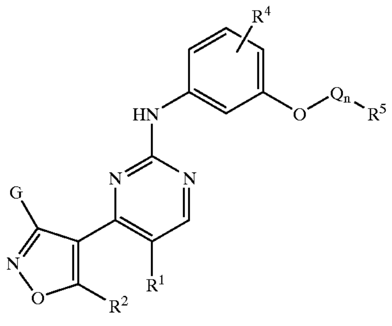
| No. | $R^1$ | 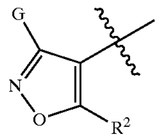 | 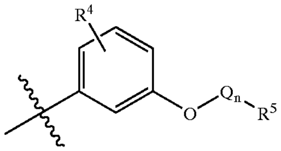 |
|---|---|---|---|
| IIIa-1 | H | 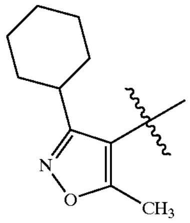 | 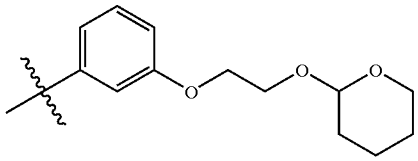 |
| IIIa-2 | H | 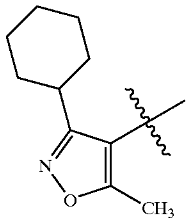 | 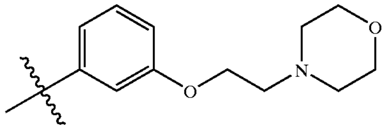 |
| IIIa-3 | H | 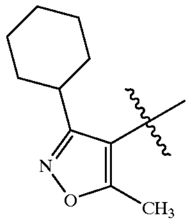 | 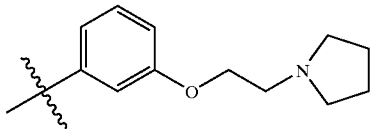 |
| IIIa-4 | H | 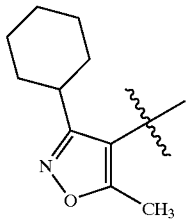 | 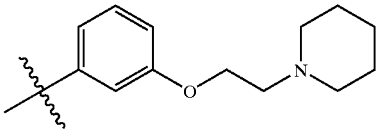 |

TABLE 2-continued
Compounds of Formula IIIa
IIIa
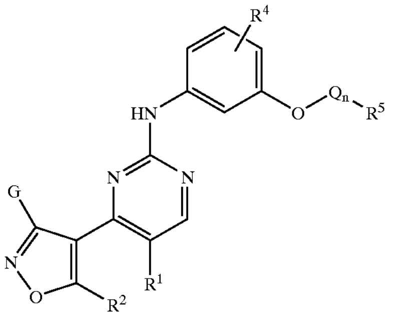
| No. | $R^1$ | 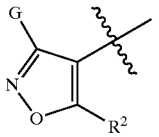 | 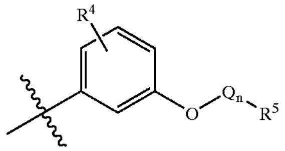 |
|---|---|---|---|
| IIIa-5 | H | 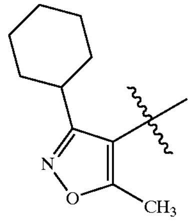 | 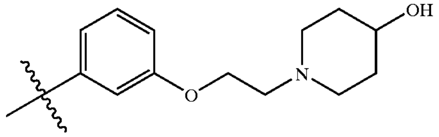 |
| IIIa-6 | H | 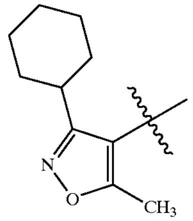 | 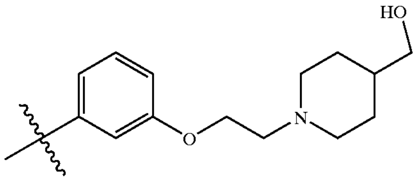 |
| IIIa-7 | H | 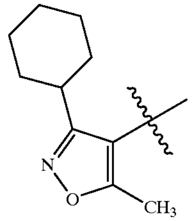 | 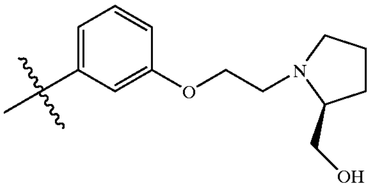 |
| IIIa-8 | H | 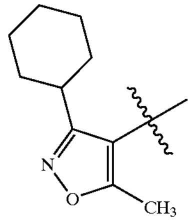 | 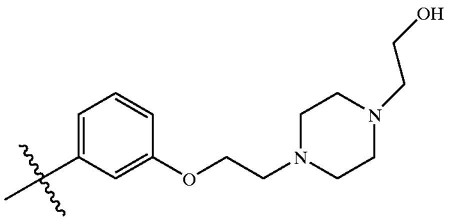 |

TABLE 2-continued
Compounds of Formula IIIa
IIIa
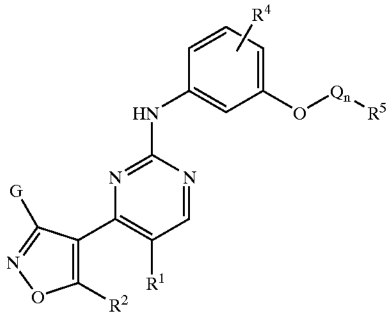
| No. | $R^1$ | 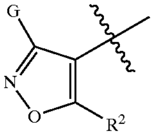 | 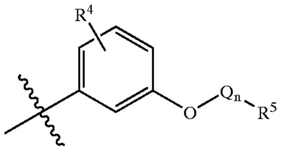 |
|---|---|---|---|
| IIIa-9 | H | 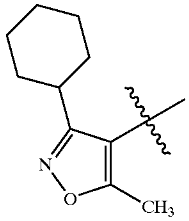 | 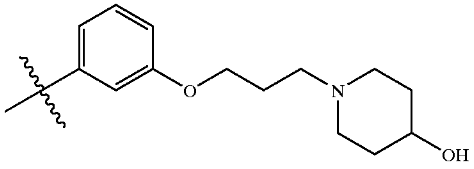 |
| IIIa-10 | H | 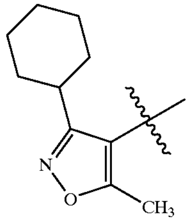 | 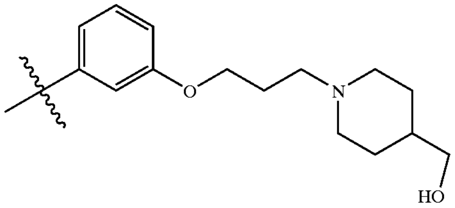 |
| IIIa-11 | H | 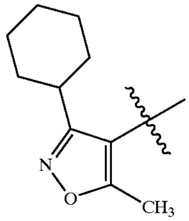 | 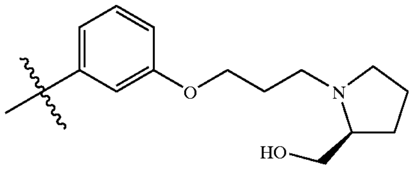 |
| IIIa-12 | H | 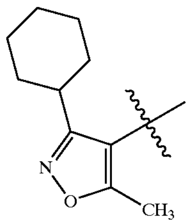 | 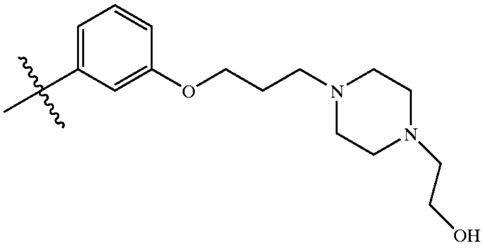 |

TABLE 2-continued
Compounds of Formula IIIa
IIIa
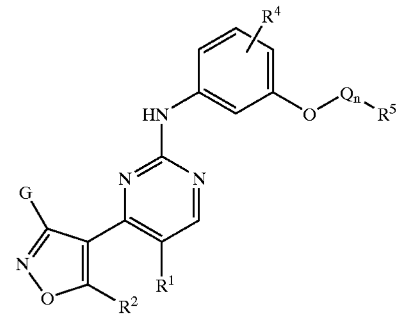
| No. | $R^1$ | 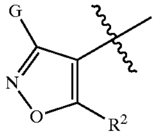 | 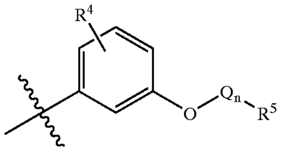 |
|---|---|---|---|
| IIIa-13 | H | 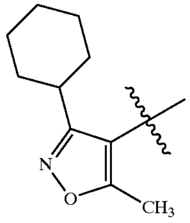 | 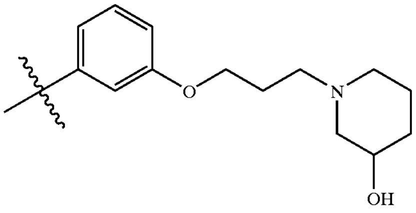 |
| IIIa-14 | H | 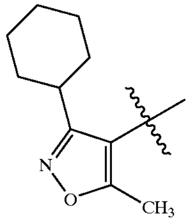 | 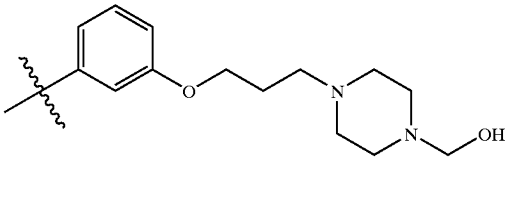 |
| IIIa-15 | H | 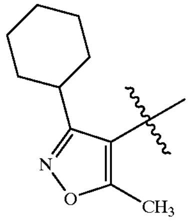 | 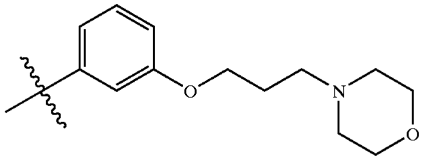 |
| IIIa-16 | H | 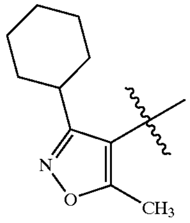 | 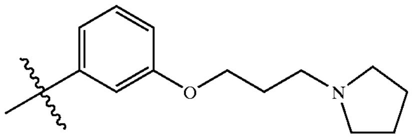 |

TABLE 2-continued
Compounds of Formula IIIa
IIIa
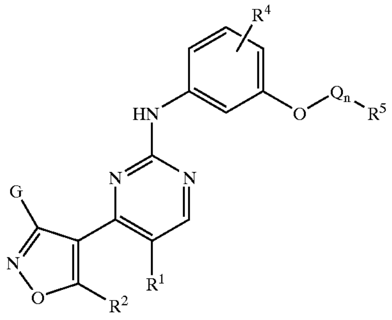
| No. | $R^1$ | 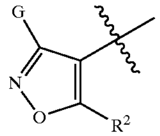 | 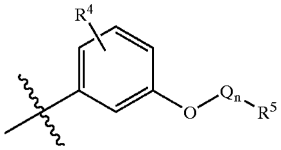 |
|---|---|---|---|
| IIIa-17 | H | 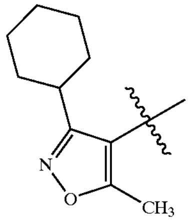 | 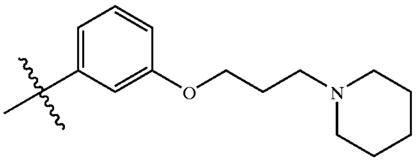 |
| IIIa-18 | H | 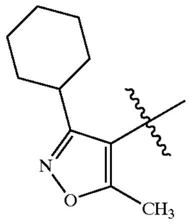 | 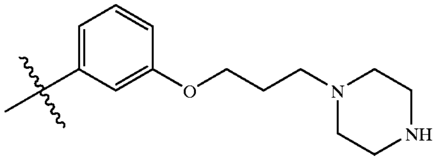 |
| IIIa-19 | H | 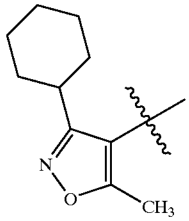 | 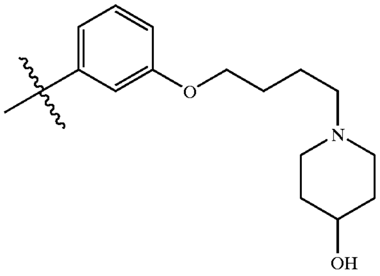 |
| IIIa-20 | H | 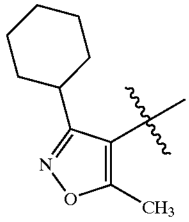 | 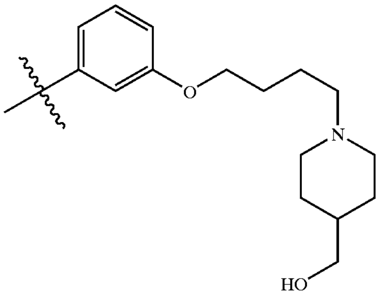 |

TABLE 2-continued
Compounds of Formula IIIa
IIIa
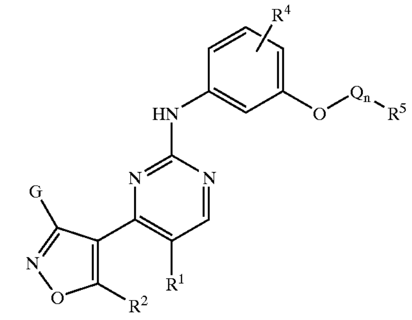
| No. | $R^1$ | 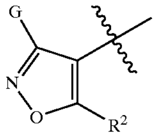 | 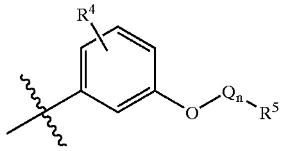 |
| --- | --- | --- | --- |
| IIIa-21 | H | 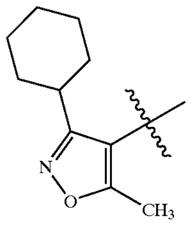 | 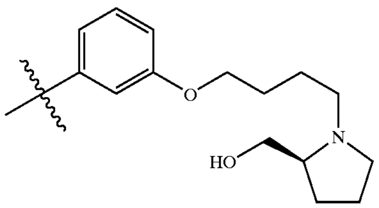 |
| IIIa-22 | H | 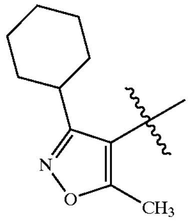 | 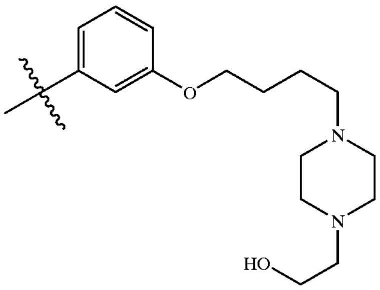 |
| IIIa-23 | H | 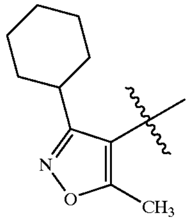 | 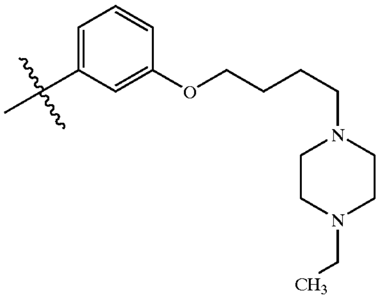 |
| IIIa-24 | H | 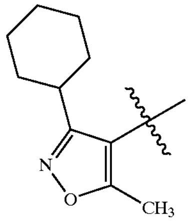 | 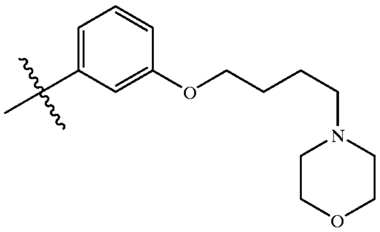 |

TABLE 2-continued
Compounds of Formula IIIa
IIIa
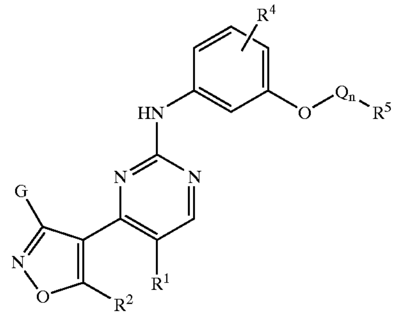
| No. | $R^1$ | 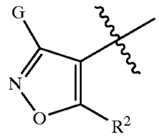 | 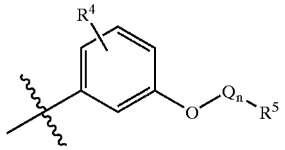 |
|---|---|---|---|
| IIIa-25 | H | 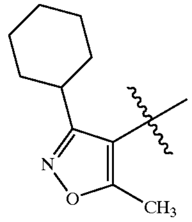 | 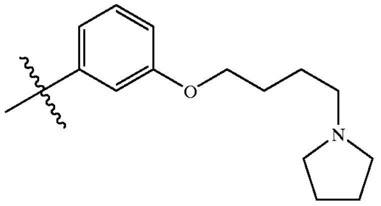 |
| IIIa-26 | H | 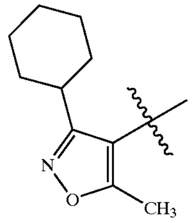 | 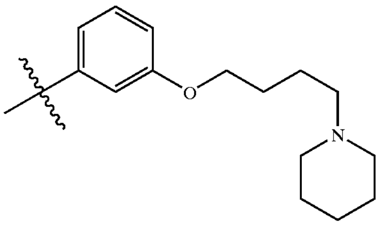 |
| IIIa-27 | H | 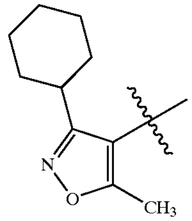 | 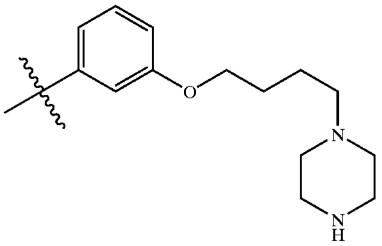 |
| IIIa-28 | H | 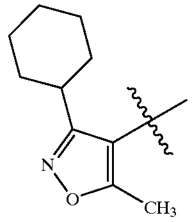 | 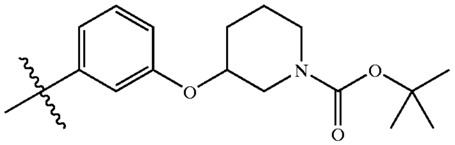 |

TABLE 2-continued
Compounds of Formula IIIa
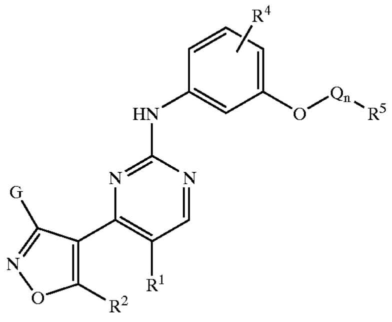
IIIa
| No. | $R^1$ | 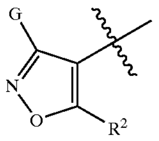 | 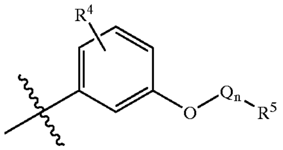 |
|---|---|---|---|
| IIIa-29 | H | 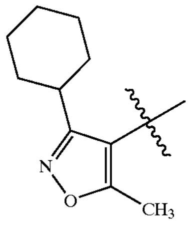 | 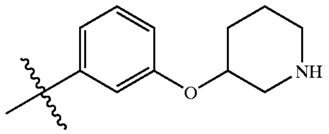 |
| IIIa-30 | H | 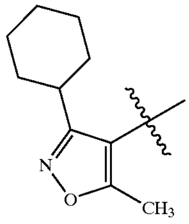 | 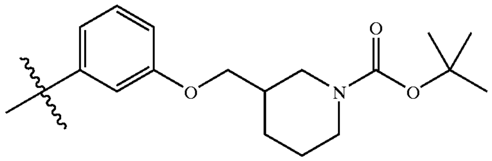 |
| IIIa-31 | H | 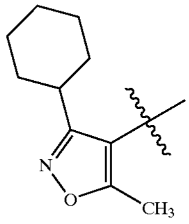 | 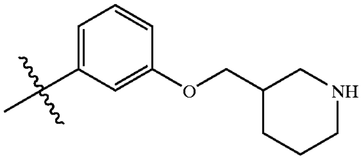 |
| IIIa-32 | $CH_3$ | 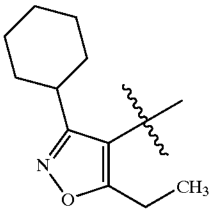 | 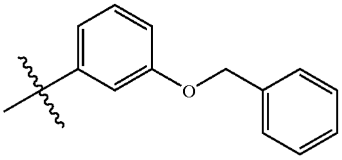 |

TABLE 2-continued
Compounds of Formula IIIa
IIIa
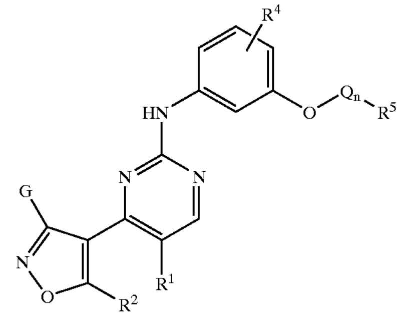
| No. | $R^1$ | 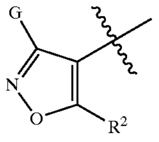 | 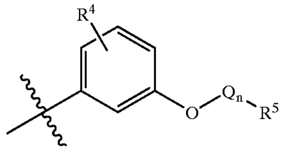 |
|---|---|---|---|
| IIIa-33 | CN | 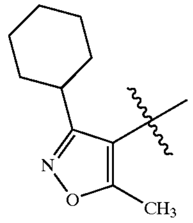 | 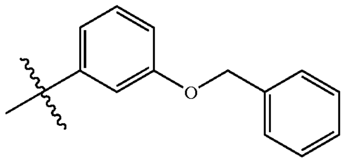 |
| IIIa-34 | H | 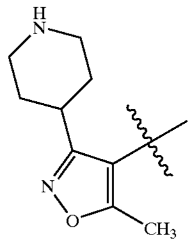 | 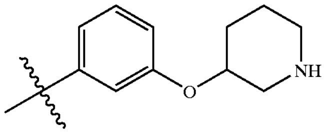 |
| IIIa-35 | H | 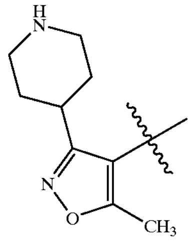 | 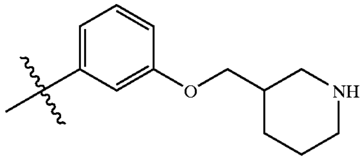 |
| IIIa-36 | $CH_3$ | 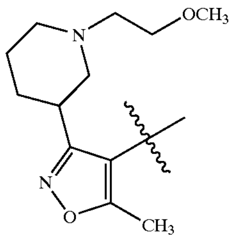 | 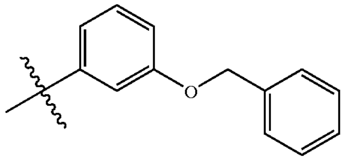 |

TABLE 2-continued
Compounds of Formula IIIa
IIIa
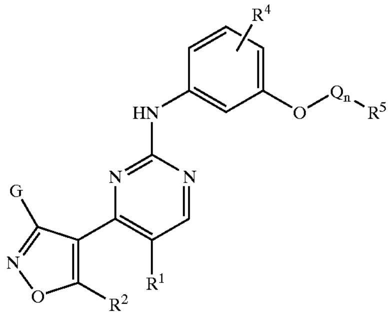
| No. | $R^1$ | 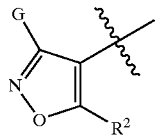 | 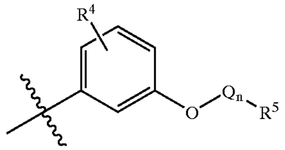 |
|---|---|---|---|
| IIIa-37 | $CH_3$ | 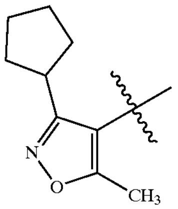 | 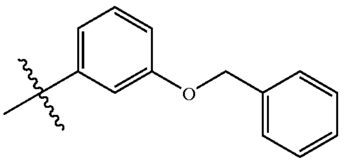 |
| IIIa-38 | $CH_3$ | 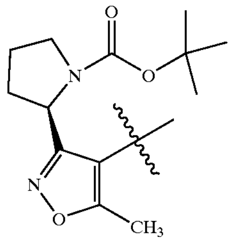 | 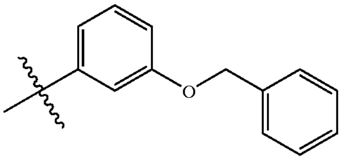 |
| IIIa-39 | $CH_3$ | 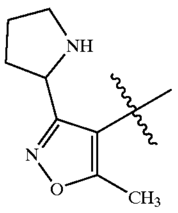 | 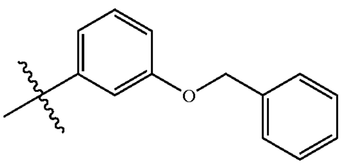 |
| IIIa-40 | 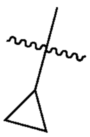 | 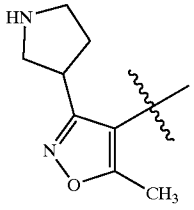 | 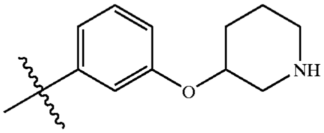 |

TABLE 2-continued
Compounds of Formula IIIa
IIIa
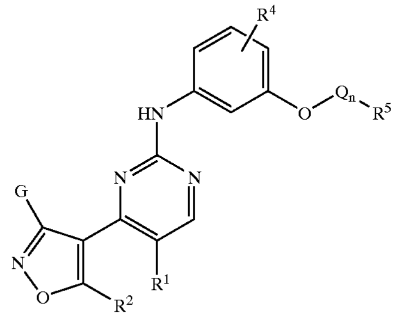
| No. | $R^1$ | 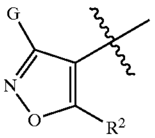 | 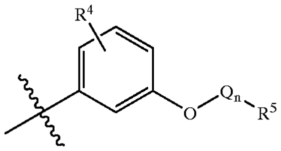 |
|---|---|---|---|
| IIIa-41 | OH | 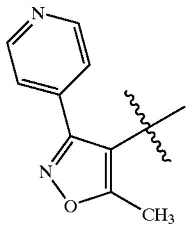 | 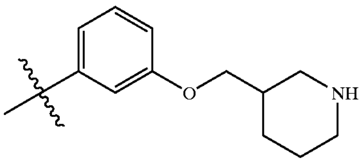 |
| IIIa-42 | $CH_3$ | 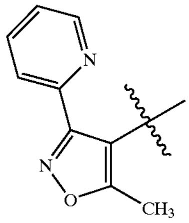 | 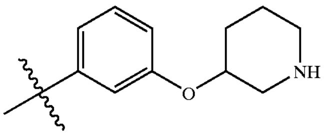 |
| IIIa-43 | H | 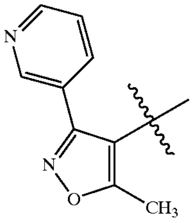 | 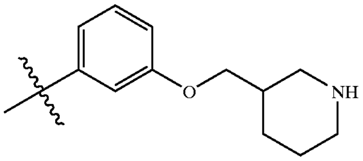 |

TABLE 2-continued
Compounds of Formula IIIa
IIIa
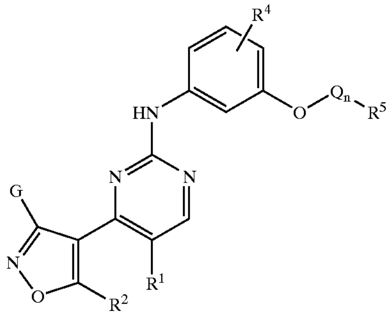
| No. | $R^1$ | 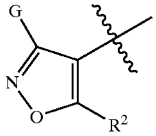 | 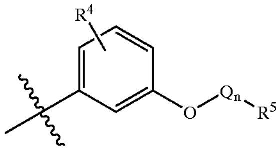 |
| --- | --- | --- | --- |
| IIIa-44 | H | 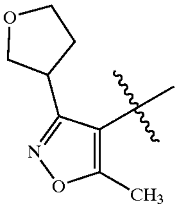 | 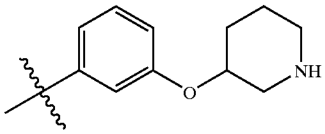 |
| IIIa-45 | H | 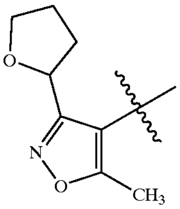 | 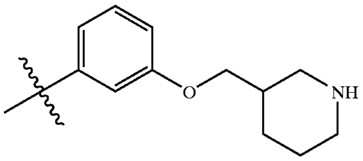 |
| IIIa-46 | H | 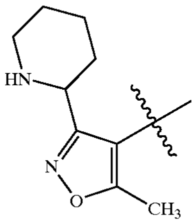 | 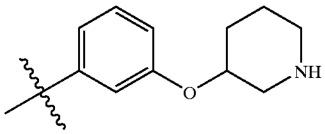 |

Exemplary structures of formula IIIb are set forth in Table 3 below.
TABLE 3
Compounds of Formula IIIb
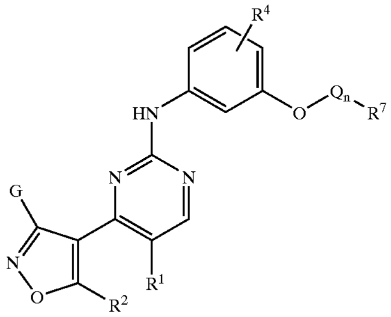
IIIb
| No. | $R^1$ | 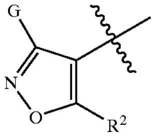 | 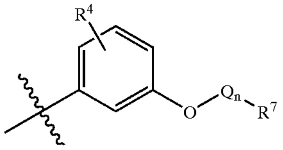 |
|---|---|---|---|
| IIIb-1 | $CH_3$ | 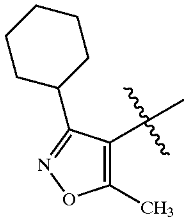 | 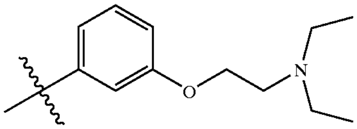 |
| IIIb-2 | $CH_3$ | 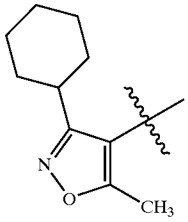 | 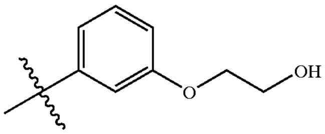 |
| IIIb-3 | $CH_2CH_3$ | 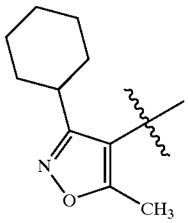 | 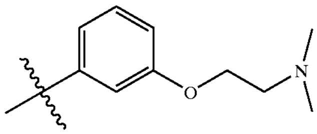 |
| IIIb-4 | $CH_2OH$ | 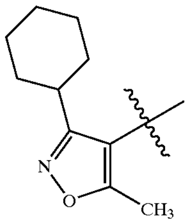 | 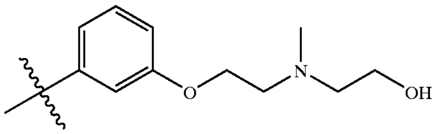 |

TABLE 3-continued
Compounds of Formula IIIb
IIIb
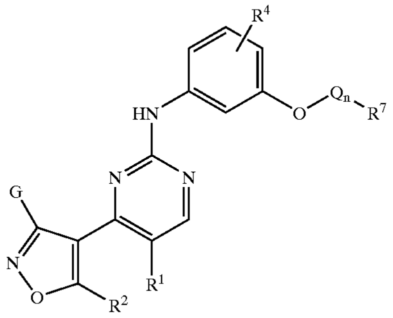
| No. | $R^1$ | 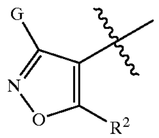 | 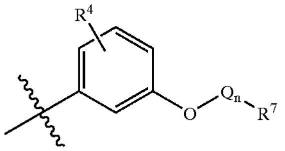 |
|---|---|---|---|
| IIIb-5 | $CH_3$ | 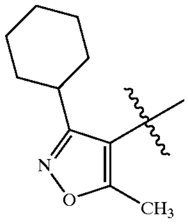 | 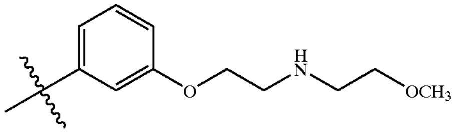 |
| IIIb-6 | $CH_2CN$ | 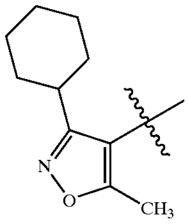 | 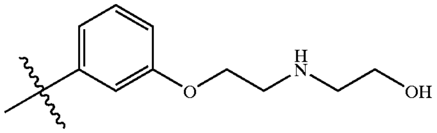 |
| IIIb-7 | $CH_2OH$ | 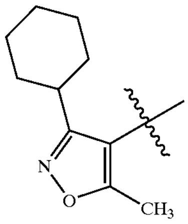 | 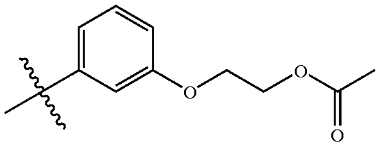 |
| IIIb-8 | $CH_3$ | 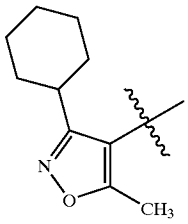 | 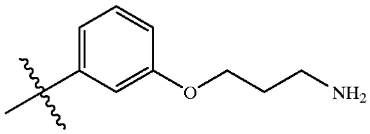 |

TABLE 3-continued
Compounds of Formula IIIb
IIIb
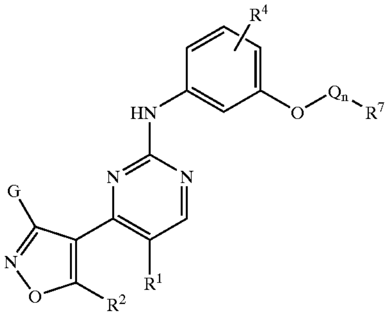
| No. | $R^1$ | 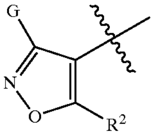 | 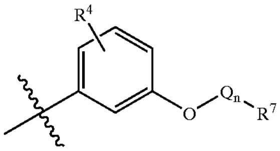 |
| --- | --- | --- | --- |
| IIIb-9 | $CH_3$ | 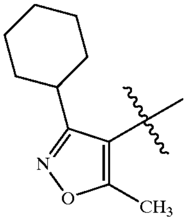 | 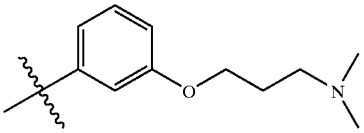 |
| IIIb-10 | $CH_2OH$ | 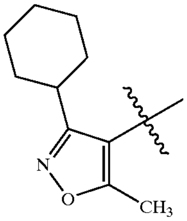 | 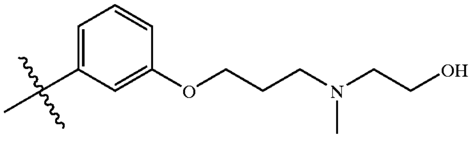 |
| IIIb-11 | $CH_3$ | 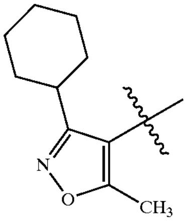 | 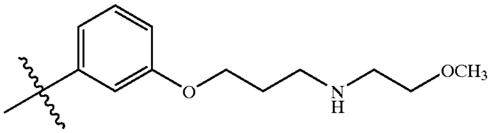 |
| IIIb-12 | $CH_2CH_3$ | 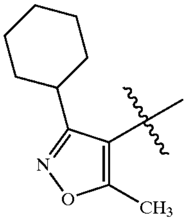 | 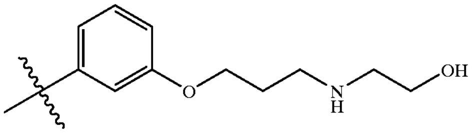 |

TABLE 3-continued
Compounds of Formula IIIb
IIIb
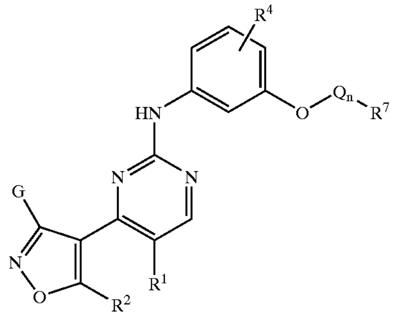
| No. | $R^1$ | 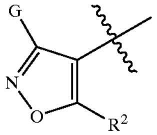 | 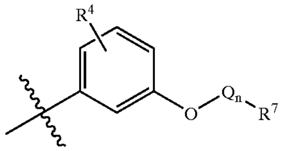 |
|---|---|---|---|
| IIIb-13 | $CH_3$ | 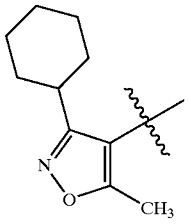 | 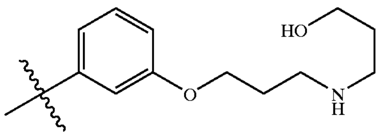 |
| IIIb-14 | $CH_3$ | 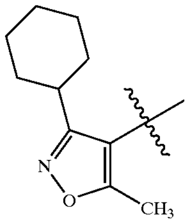 | 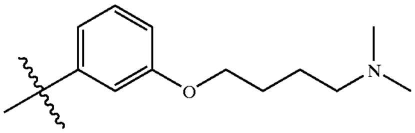 |
| IIIb-15 | $CH_3$ | 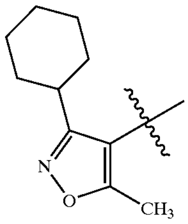 | 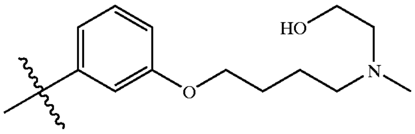 |
| IIIb-16 | $CH_3$ | 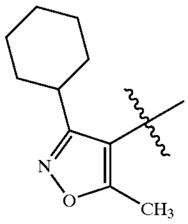 | 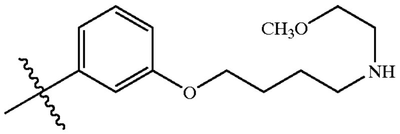 |

TABLE 3-continued
Compounds of Formula IIIb
IIIb
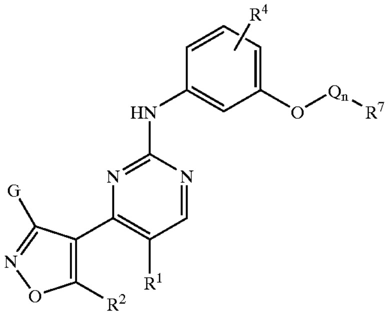
| No. | $R^1$ | 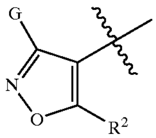 | 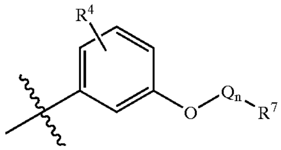 |
|---|---|---|---|
| IIIb-17 | $CH_3$ | 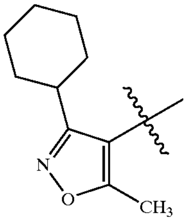 | 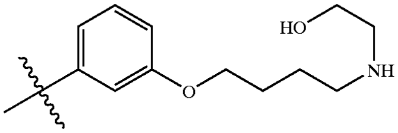 |
| IIIb-18 | $CH_2OH$ | 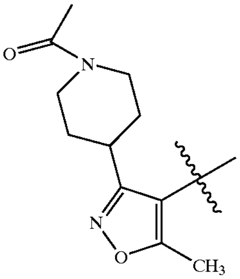 | 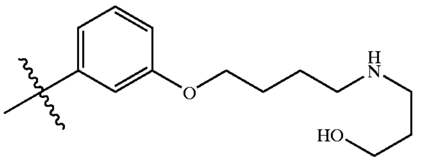 |
| IIIb-19 | $CH_2OH$ | 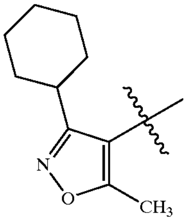 | 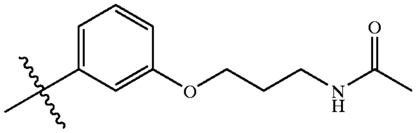 |
| IIIb-20 | $CH_2OH$ | 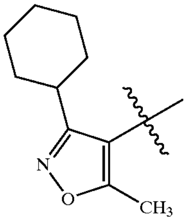 | 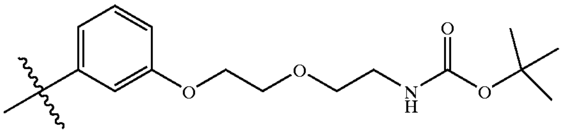 |

TABLE 3-continued
Compounds of Formula IIIb
IIIb
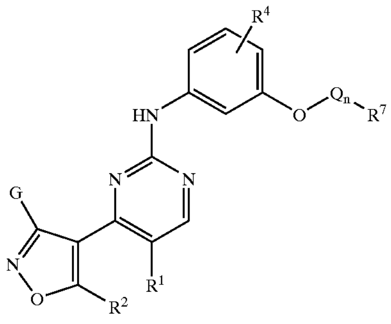
| No. | $R^1$ | 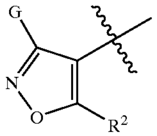 | 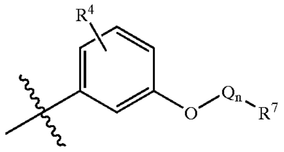 |
|---|---|---|---|
| IIIb-21 | $CH_2OH$ | 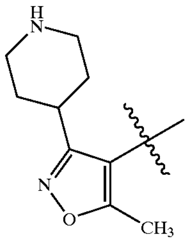 | 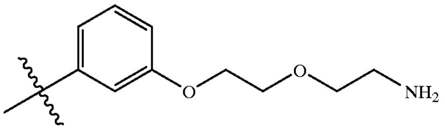 |
| IIIb-22 | $CH_3$ | 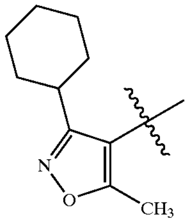 | 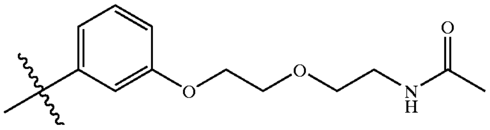 |
| IIIb-23 | $CO_2CH_3$ | 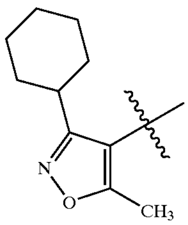 | 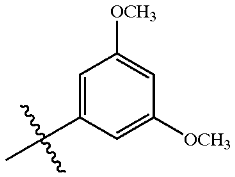 |
| IIIb-24 | $CO_2H$ | 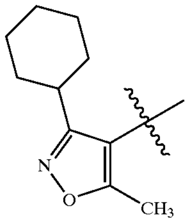 | 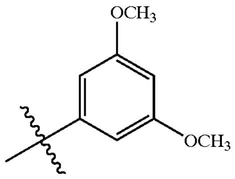 |

TABLE 3-continued
Compounds of Formula IIIb
IIIb
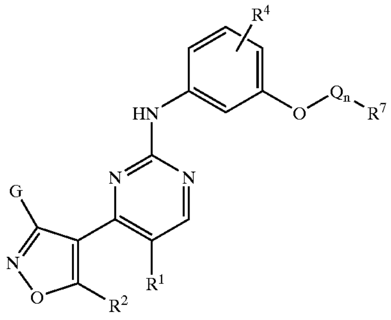
| No. | $R^1$ | 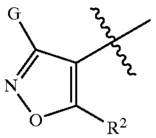 | 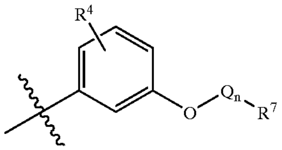 |
|---|---|---|---|
| IIIb-25 | $CH_2OH$ | 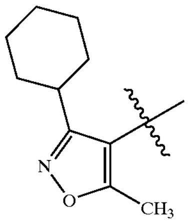 | 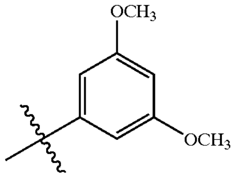 |
| IIIb-26 | $C(O)NH_2$ | 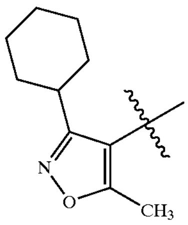 | 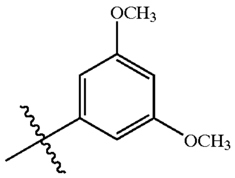 |
| IIIb-27 | CN | 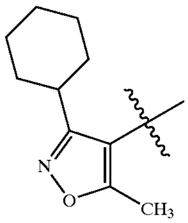 | 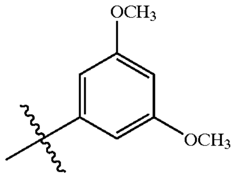 |

TABLE 3-continued

Compounds of Formula IIIb

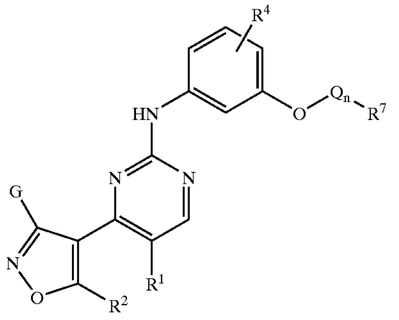

IIIb

| No. | $R^1$ | 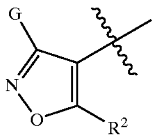 | 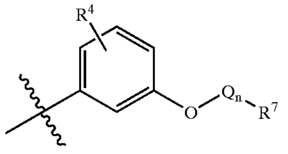 |
|---|---|---|---|
| IIIb-28 | $CH_3$ | 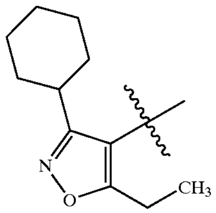 | 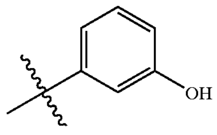 |
| IIIb-29 | $CH_2OCH_2CH_2CH_3$ | 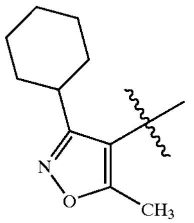 | 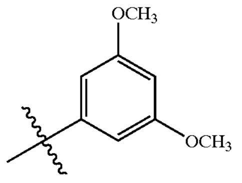 |

According to another preferred embodiment, the present invention relates to a compound of formula IVa or IVb:

IVa

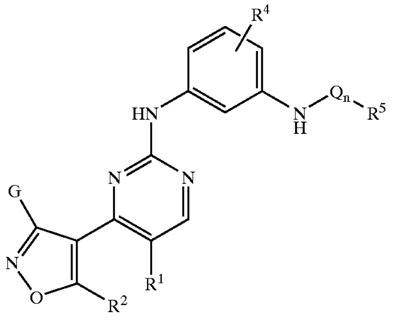

-continued

IVb

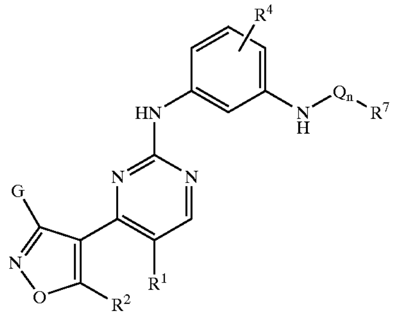

or a pharmaceutically acceptable derivative thereof, wherein G, Q, n, $R^1$, $R^2$, $R^4$, $R^5$, and $R^7$ are as described above.

Preferred G, Q, n, $R^1$, $R^2$, $R^4$, $R^5$, and $R^7$ groups of formulae IVa and IVb are those described for compounds of formulae Ia and Ib above.

Exemplary structures of formula IVa are set forth in Table 4 below.
TABLE 4
Compounds of Formula IVa
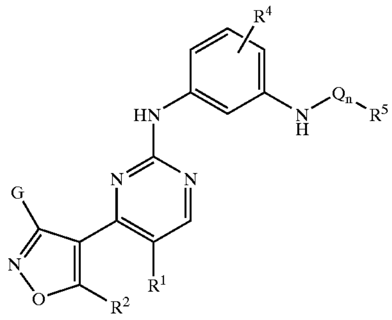
IVa
| No. | $R^1$ | 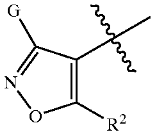 | 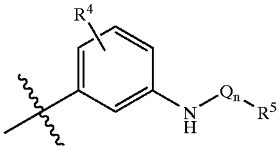 |
|---|---|---|---|
| IVa-1 | H | 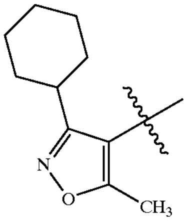 | 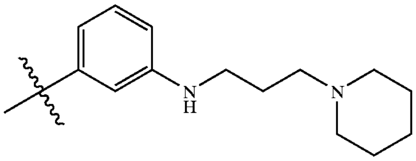 |
| IVa-2 | H | 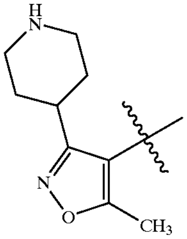 | 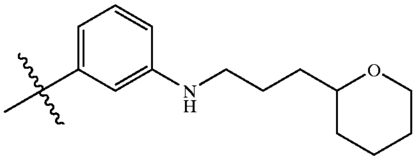 |
| IVa-3 | H | 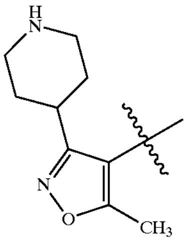 | 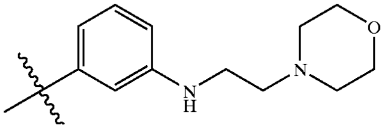 |
| IVa-4 | H | 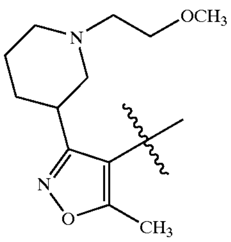 | 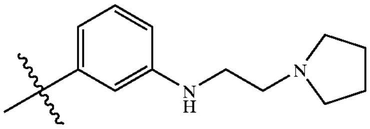 |

TABLE 4-continued
Compounds of Formula IVa
IVa
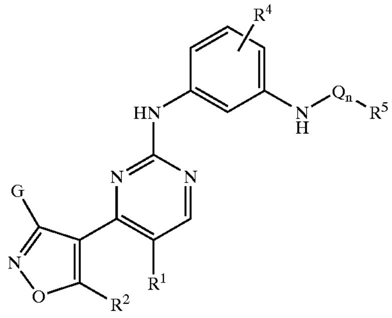
| No. | $R^1$ | 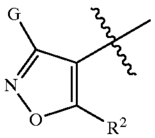 | 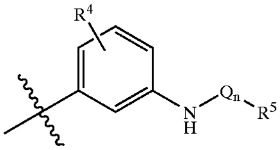 |
|---|---|---|---|
| IVa-5 | $CH_3$ | 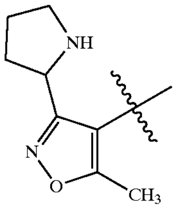 | 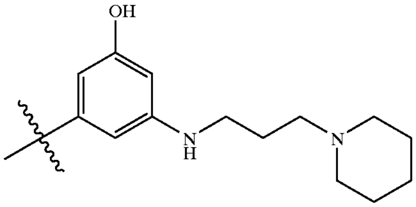 |
| IVa-6 | $CH_3$ | 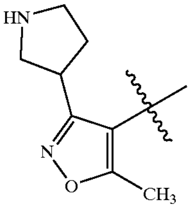 | 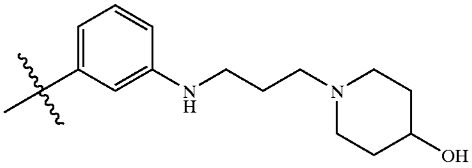 |
| IVa-7 | $CH_3$ | 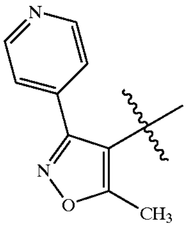 | 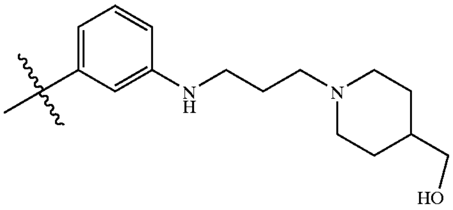 |
| IVa-8 | $CH_3$ | 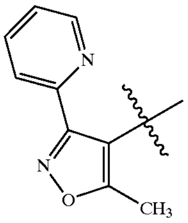 | 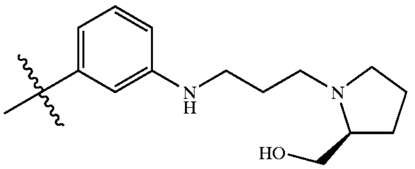 |

TABLE 4-continued
Compounds of Formula IVa
IVa
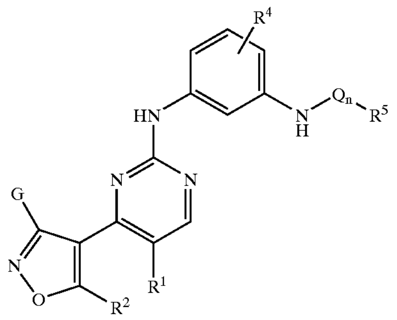
| No. | $R^1$ | 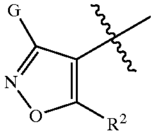 | 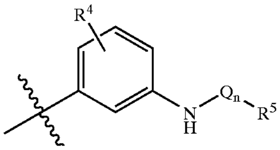 |
|---|---|---|---|
| IVa-9 | H | 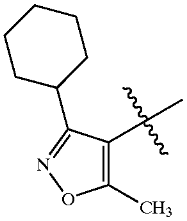 | 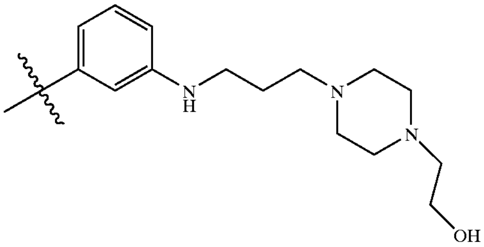 |
| IVa-10 | H | 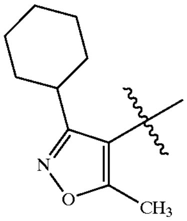 | 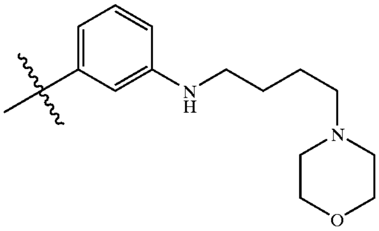 |
| IVa-11 | H | 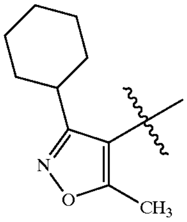 | 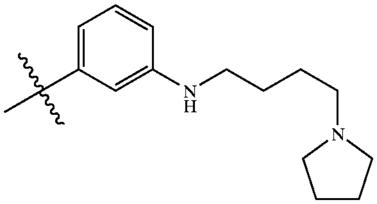 |
| IVa-12 | H | 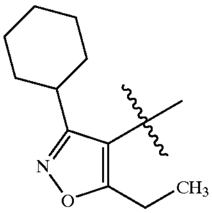 | 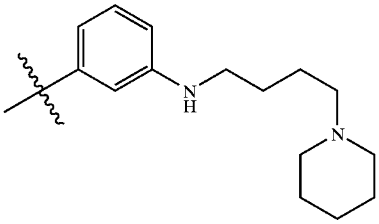 |

TABLE 4-continued
Compounds of Formula IVa
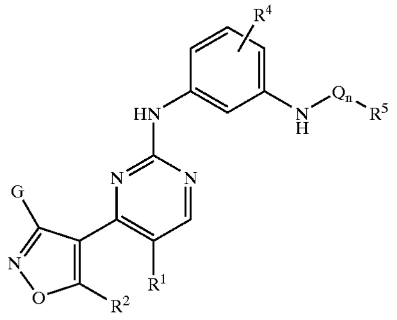
IVa
| No. | $R^1$ | 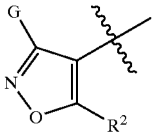 | 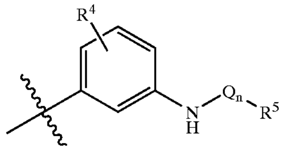 |
|---|---|---|---|
| IVa-13 | $CH_3$ | 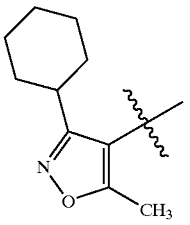 | 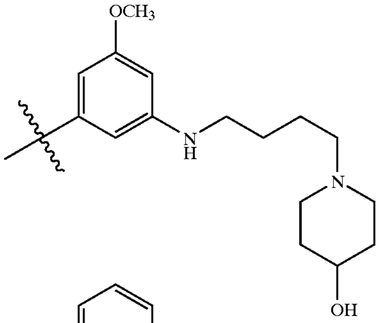 |
| IVa-14 | $CH_3$ | 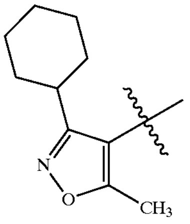 | 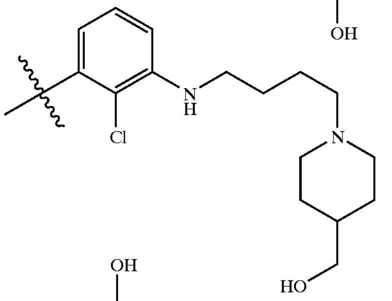 |
| IVa-15 | $CH_3$ | 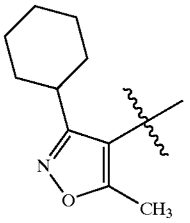 | 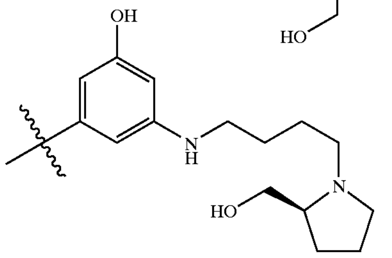 |
| IVa-16 | $CH_3$ | 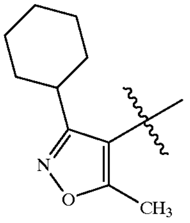 | 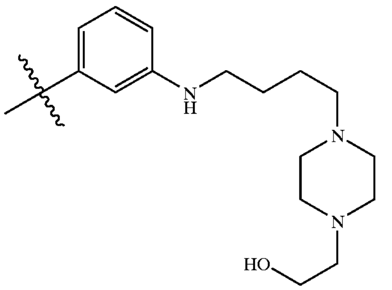 |

Exemplary structures of formula IVb are set forth in Table 5 below.
TABLE 5
Compounds of Formula IVb
IVb
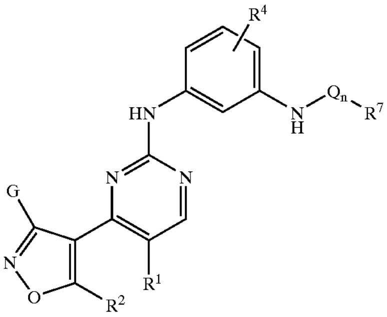
| No. | $R^1$ | 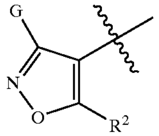 | 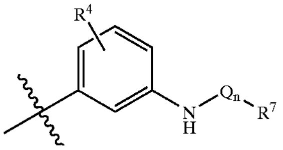 |
|---|---|---|---|
| IVb-1 | $CH_3$ | 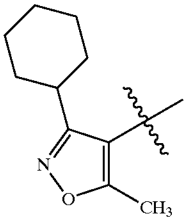 | 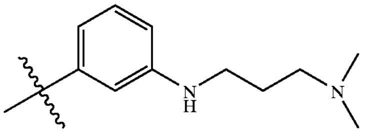 |
| IVb-2 | $CH_2CH_3$ | 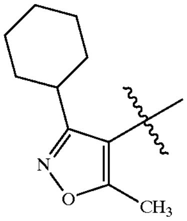 | 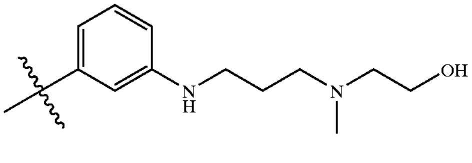 |
| IVb-3 | $CH_3$ | 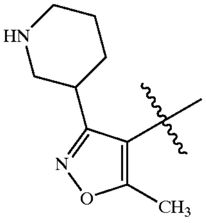 | 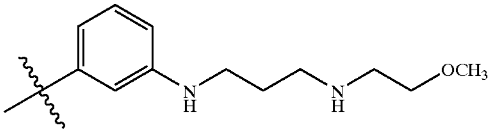 |
| IVb-4 | $CH_2OH$ | 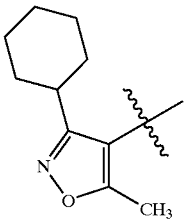 | 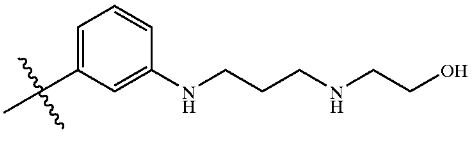 |

TABLE 5-continued
Compounds of Formula IVb
IVb
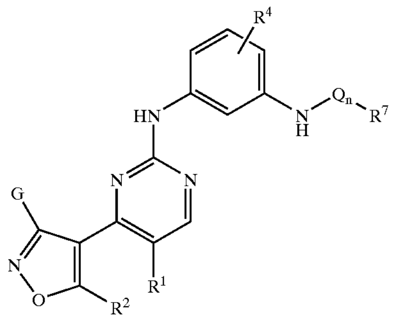
| No. | $R^1$ | 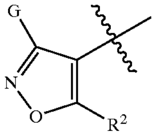 | 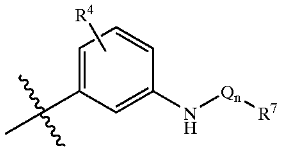 |
|---|---|---|---|
| IVb-5 | OH | 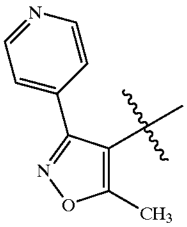 | 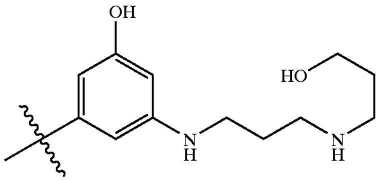 |
| IVb-6 | $CH_2CH_3$ | 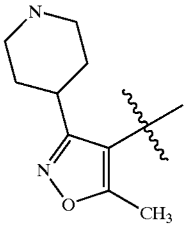 | 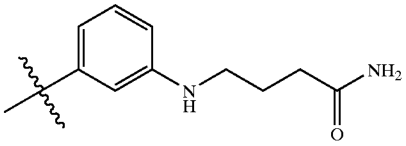 |
| IVb-7 | $CH_2CN$ | 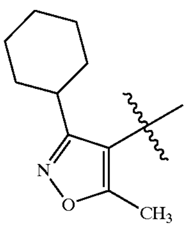 | 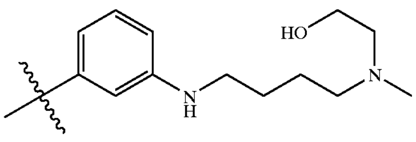 |

TABLE 5-continued

Compounds of Formula IVb

IVb

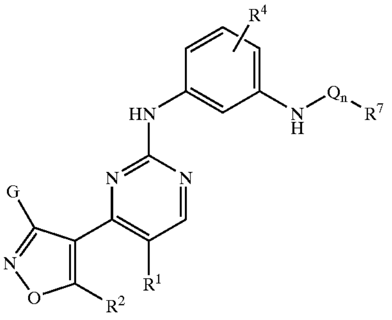

| No. | $R^1$ | 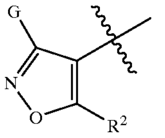 | 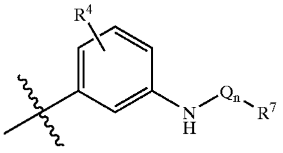 |
|---|---|---|---|
| IVb-8 | 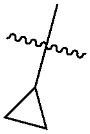 | 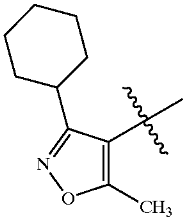 | 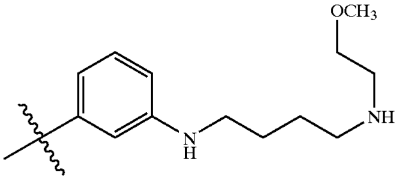 |
| IVb-9 | $NH_2$ | 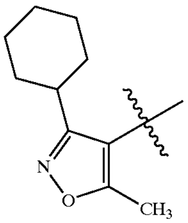 | 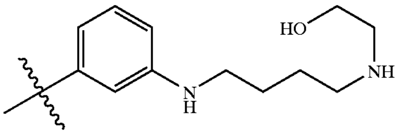 |

According to another preferred embodiment, the present invention relates to a compound of formula Va or Vb:

Va

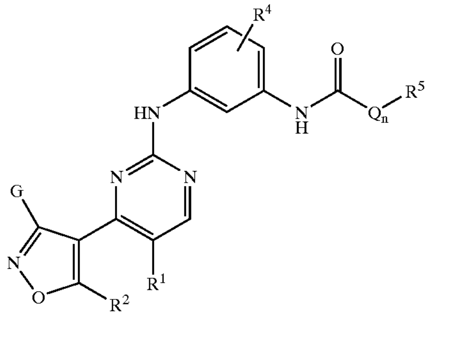

-continued

Vb

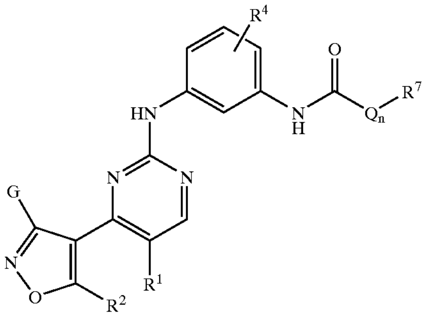

or a pharmaceutically acceptable derivative thereof, wherein G, Q, n, $R^1$, $R^2$, $R^4$, $R^5$, and $R^7$ are as described above.

Preferred G, Q, n, $R^1$, $R^2$, $R^4$, $R^5$, and $R^7$ groups of formulae Va and Vb are those described for compounds of formulae Ia and Ib above.

Exemplary structures of formula Va are set forth in Table 6 below.
TABLE 6
Compounds of Formula Va
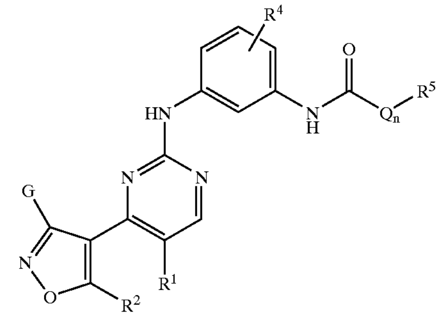
Va
| No. | $R^1$ | 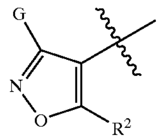 | 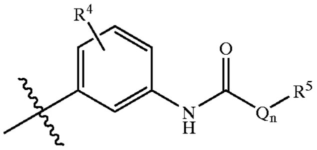 |
|---|---|---|---|
| Va-1 | H | 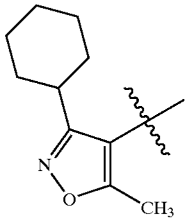 | 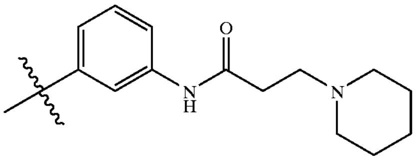 |
| Va-2 | H | 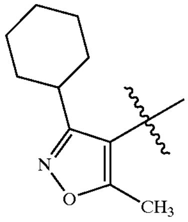 | 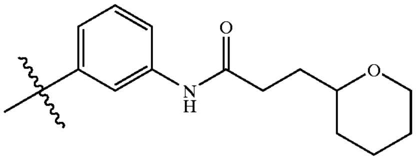 |
| Va-3 | H | 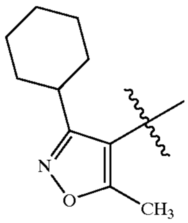 | 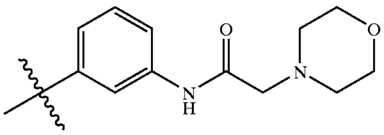 |
| Va-4 | $CH_3$ | 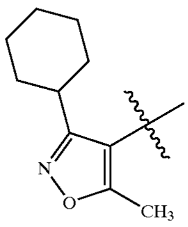 | 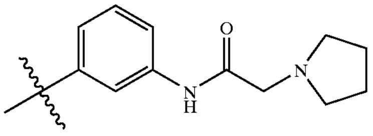 |

TABLE 6-continued
Compounds of Formula Va
Va
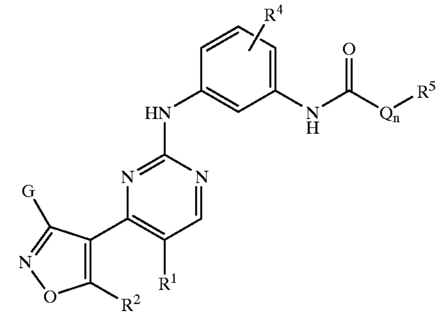
| No. | $R^1$ | 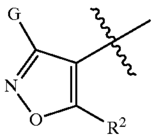 | 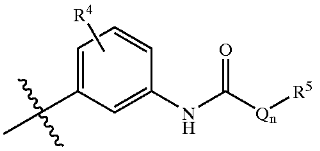 |
|---|---|---|---|
| Va-5 | H | 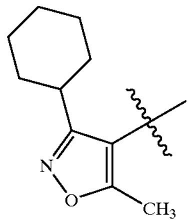 | 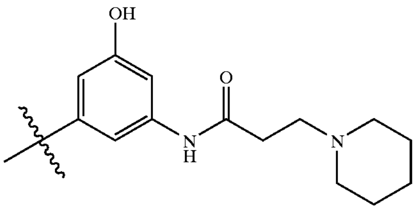 |
| Va-6 | H | 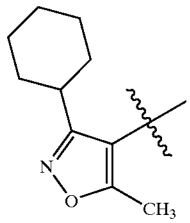 | 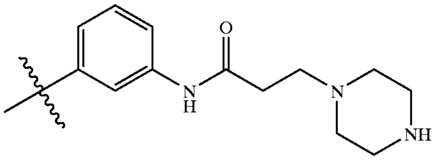 |
| Va-7 | $CH_2CH_3$ | 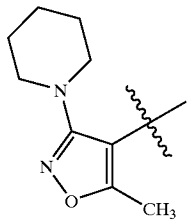 | 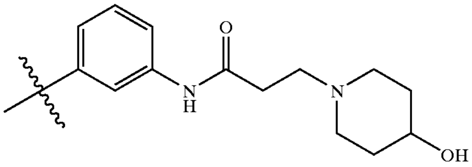 |
| Va-8 | $CH_2CN$ | 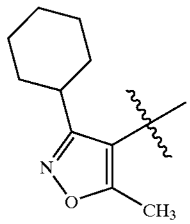 | 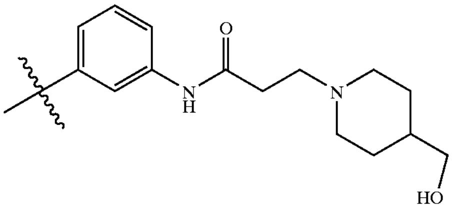 |

TABLE 6-continued
Compounds of Formula Va
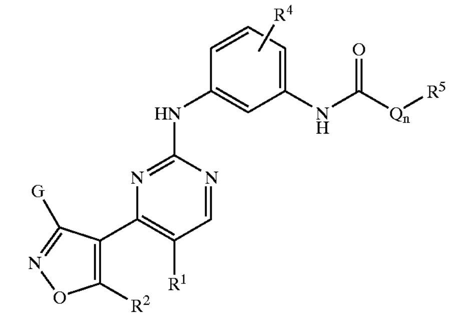
Va
| No. | $R^1$ | 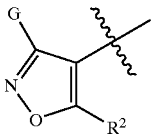 | 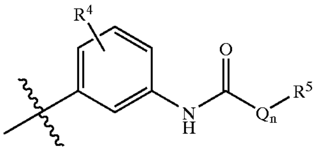 |
|---|---|---|---|
| Va-9 | $CH_2OH$ | 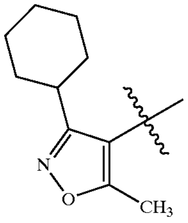 | 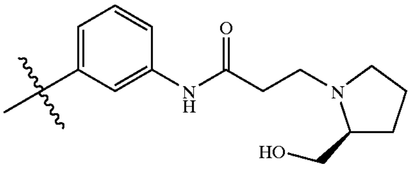 |
| Va-10 | H | 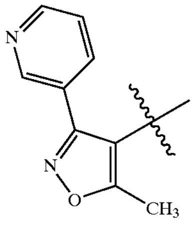 | 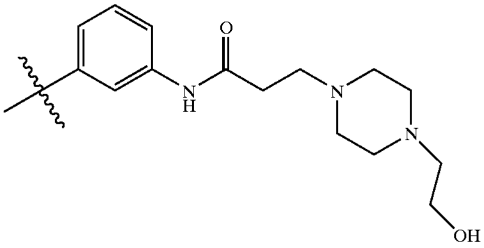 |
| Va-11 | H | 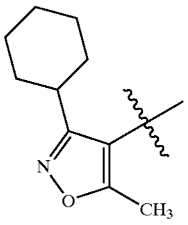 | 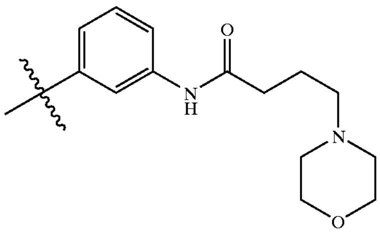 |

TABLE 6-continued
Compounds of Formula Va
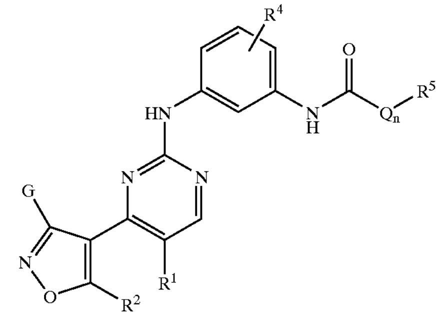
Va
| No. | $R^1$ | 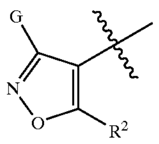 | 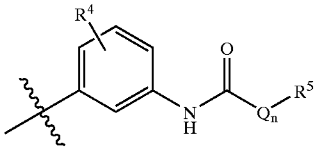 |
|---|---|---|---|
| Va-12 | H | 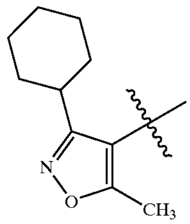 | 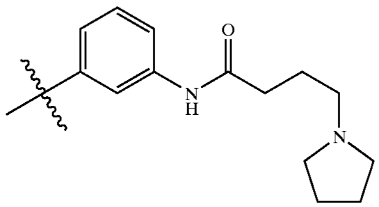 |
| Va-13 | $CH_3$ | 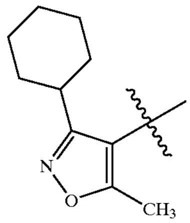 | 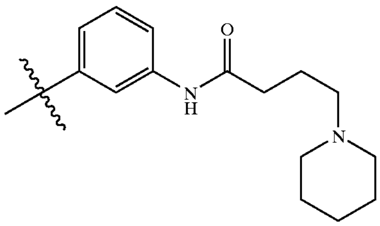 |
| Va-14 | OH | 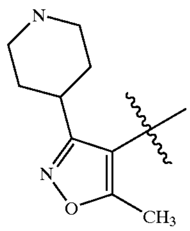 | 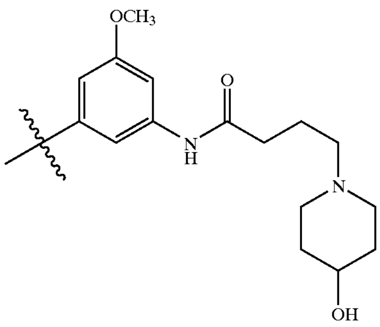 |

TABLE 6-continued
Compounds of Formula Va
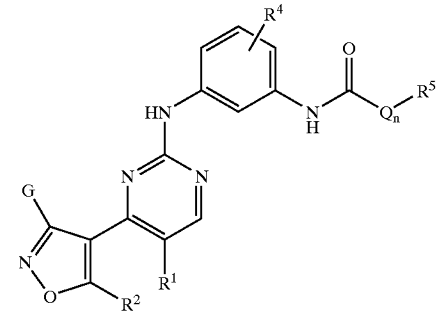
Va
| No. | $R^1$ | 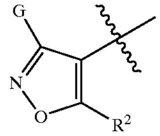 | 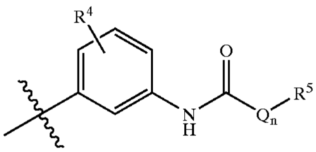 |
|---|---|---|---|
| Va-15 | H | 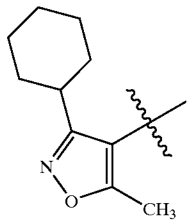 | 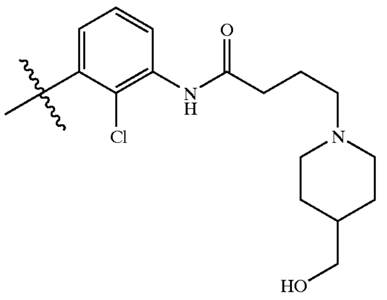 |
| Va-16 | $NH_2$ | 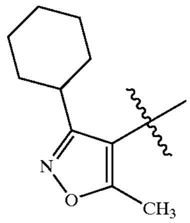 | 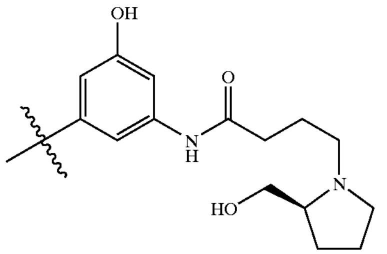 |
| Va-17 | H | 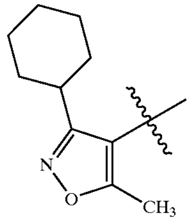 | 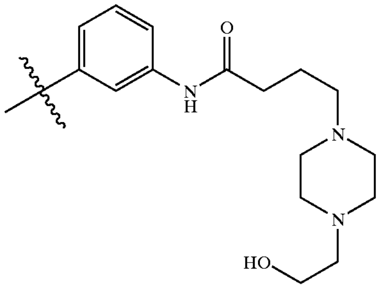 |

Exemplary structures of formula Vb are set forth in Table 7 below.
TABLE 7
Compounds of Formula Vb
Vb
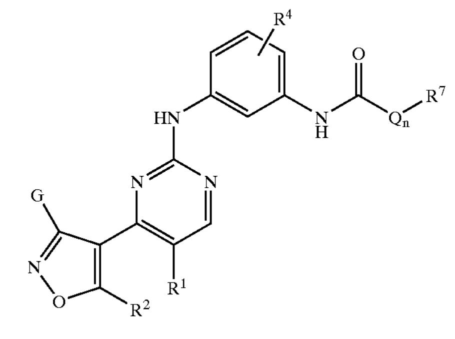
| No. | $R^1$ | 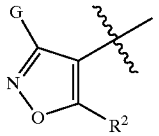 | 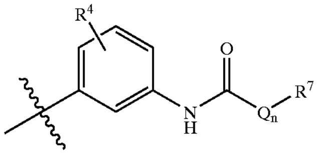 |
|---|---|---|---|
| Vb-1 | $CH_3$ | 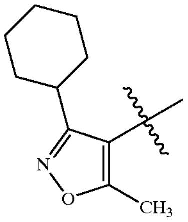 | 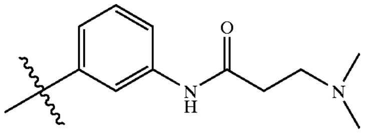 |
| Vb-2 | $CH_2CH_3$ | 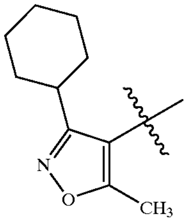 | 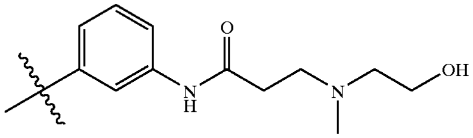 |
| Vb-3 | $CH_3$ | 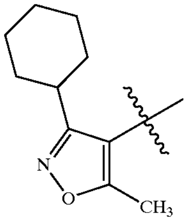 | 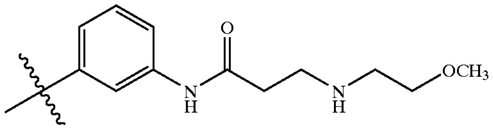 |
| Vb-4 | $CH_2OH$ | 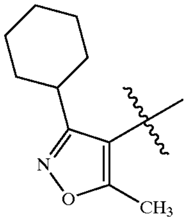 | 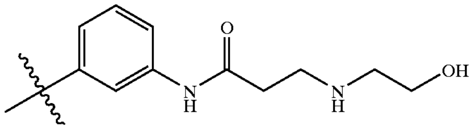 |

TABLE 7-continued
Compounds of Formula Vb
Vb
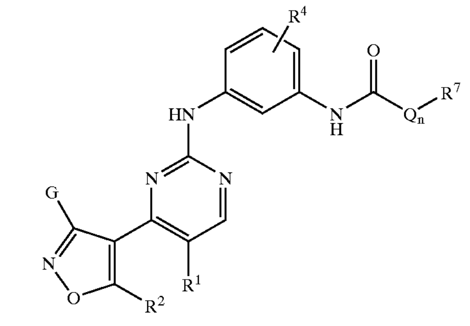
| No. | $R^1$ | 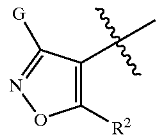 | 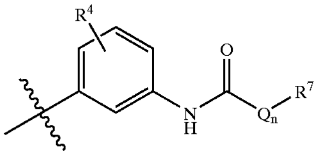 |
|---|---|---|---|
| Vb-5 | OH | 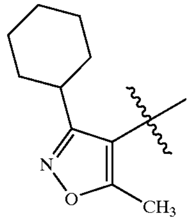 | 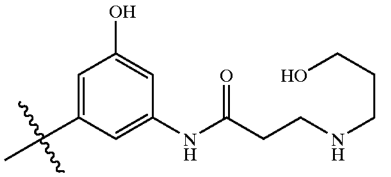 |
| Vb-6 | $CH_2CH_3$ | 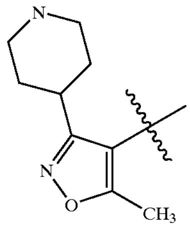 | 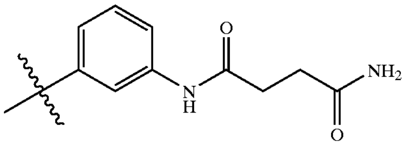 |
| Vb-7 | $CH_2CN$ | 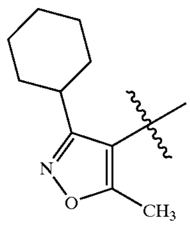 | 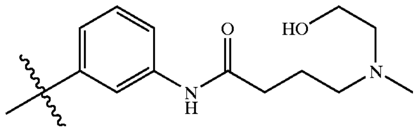 |
| Vb-8 | $CH_2OH$ | 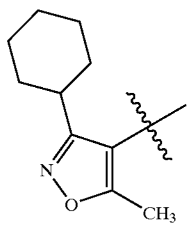 | 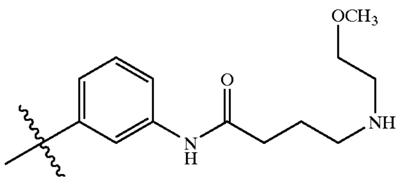 |

TABLE 7-continued
Compounds of Formula Vb
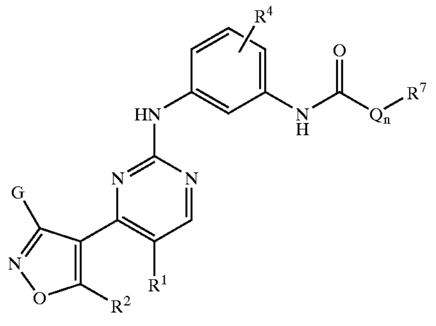
Vb
| No. | $R^1$ | 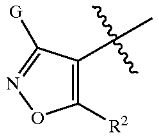 | 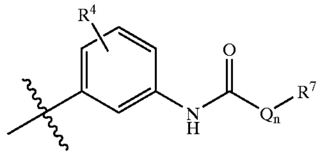 |
|---|---|---|---|
| Vb-9 | $NH_2$ | 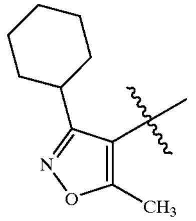 | 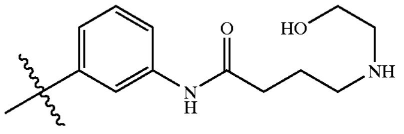 |
| Vb-10 | $CH_2CN$ | 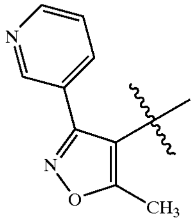 | 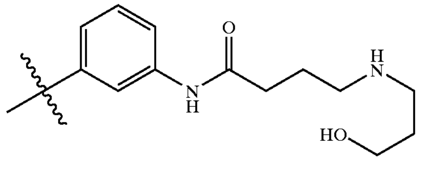 |
| Vb-11 | $CH_2OH$ | 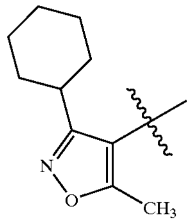 | 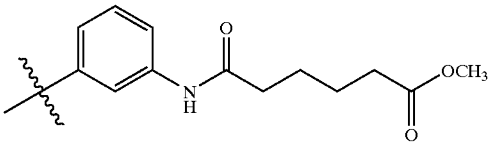 |
| Vb-12 | $NH_2$ | 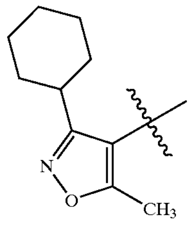 | 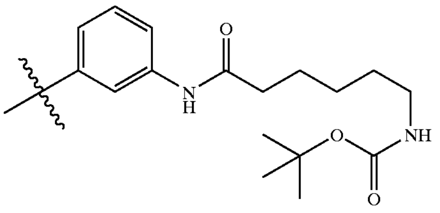 |

TABLE 7-continued
Compounds of Formula Vb
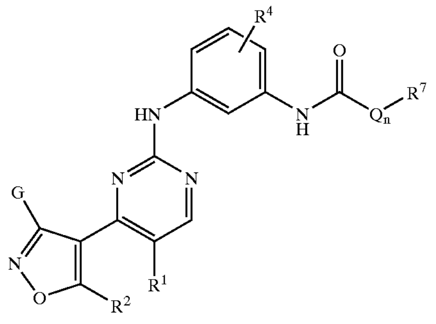
Vb
| No. | $R^1$ | 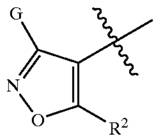 | 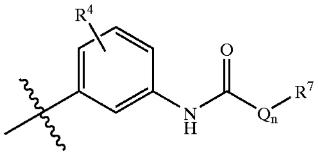 |
| --- | --- | --- | --- |
| Vb-13 | $CH_2OH$ | 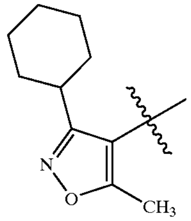 | 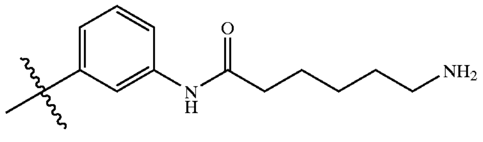 |
| Vb-14 | $CH_3$ | 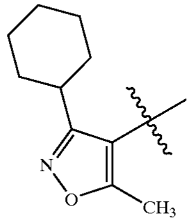 | 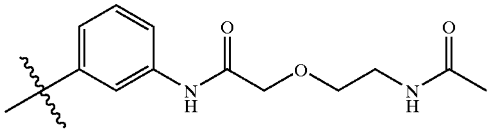 |
| Vb-15 | $CH_2CH_3$ | 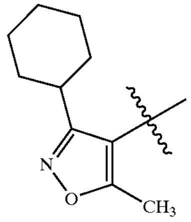 | 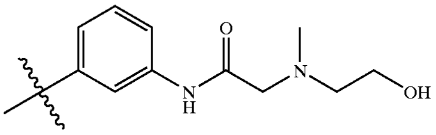 |
| Vb-16 | $CH_3$ | 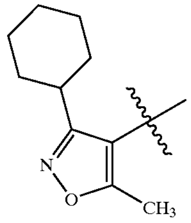 | 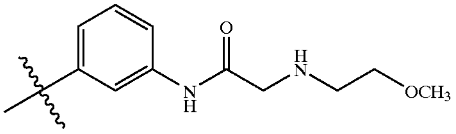 |

TABLE 7-continued
Compounds of Formula Vb
Vb
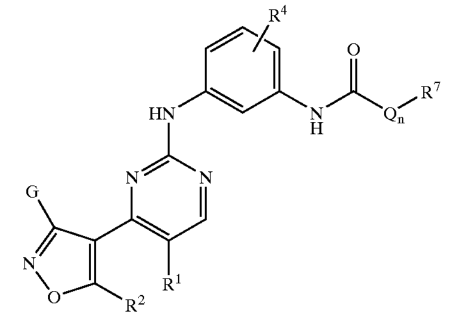
| No. | $R^1$ | 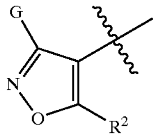 | 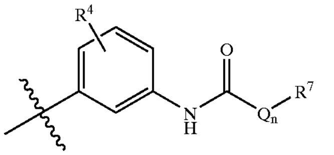 |
|---|---|---|---|
| Vb-17 | $CH_2OH$ | 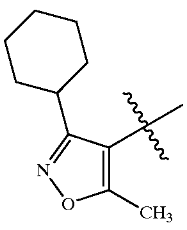 | 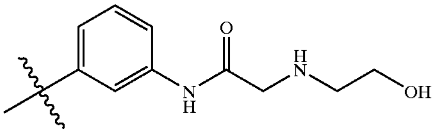 |
| Vb-18 | $OCH_3$ | 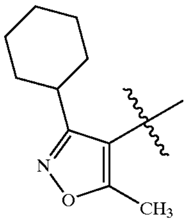 | 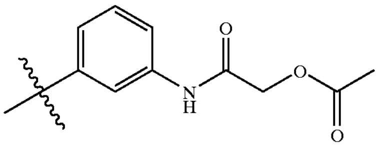 |
| Vb-19 | $CH_2OCH_3$ | 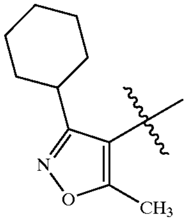 | 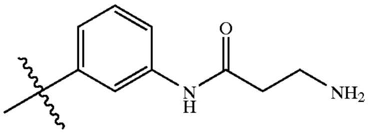 |

TABLE 7-continued
Compounds of Formula Vb
Vb
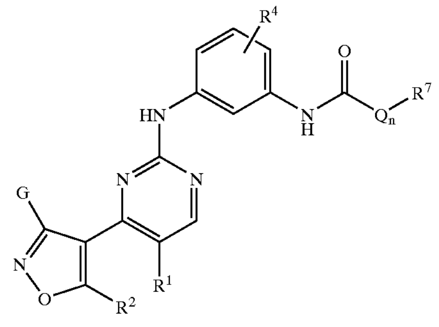
| No. | $R^1$ | 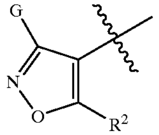 | 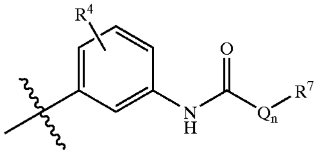 |
|---|---|---|---|
| Vb-20 | $CH_3$ | 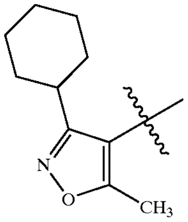 | 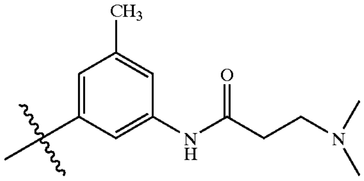 |
| Vb-21 | $CH_2CH_3$ | 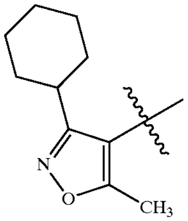 | 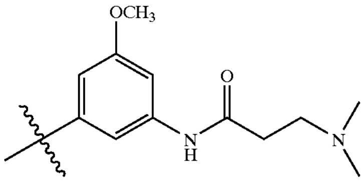 |
| Vb-22 | $CH_2OH$ | 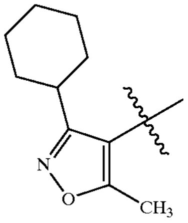 | 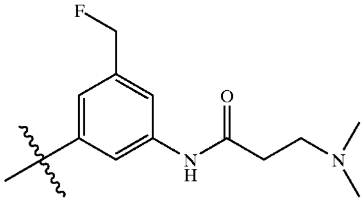 |

The present compounds may be prepared in general by methods known to those skilled in the art for analogous compounds, as illustrated by the general Schemes I, II, III, IV, V, and VI and the synthetic examples shown below.

Scheme I

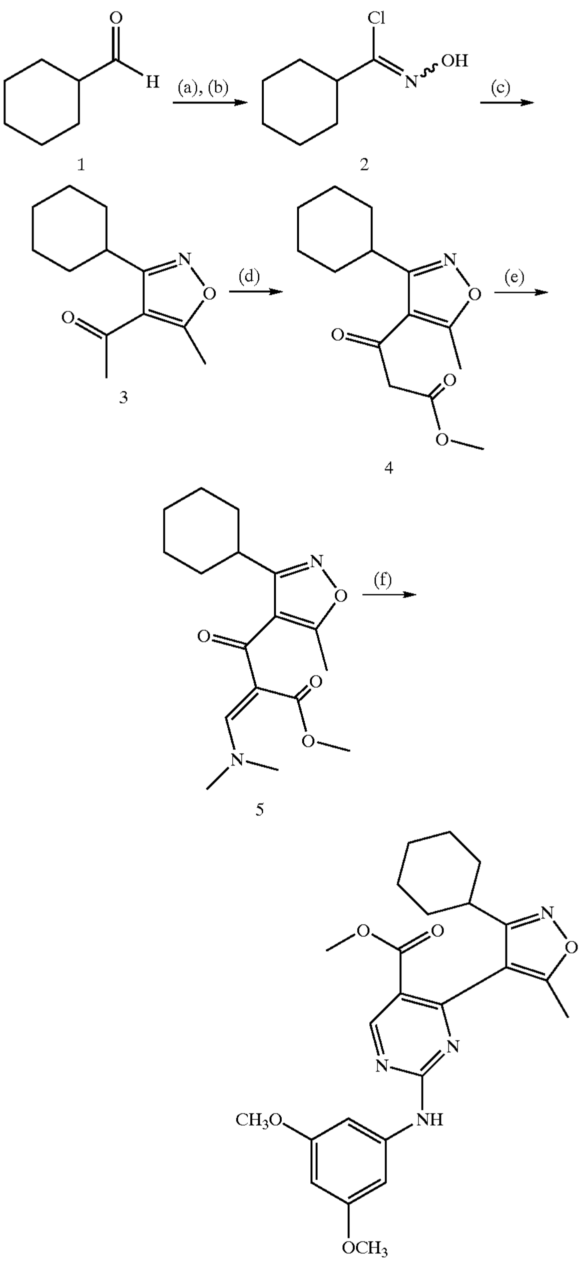

1
2
3
4
5
IIIb-23

Reagents and conditions: (a) $H_2NOH•HCl$, $Et_3N$, $CH_2Cl_2$; (b) HCl, oxone, 1,4-dioxane, DMF; (c) 2,4-pentanedione, $Et_3N$, EtOH; (d) methylcarbonate; (e)DMF-DMA (f) 3,5-dimethoxyphenylguanidine, NaOMe, MeOH.

Using compound IIIb-23 as an example, Scheme I above shows a general synthetic route that may be used for preparing compounds of formula I wherein $R^1$ is other than hydrogen. In step (a), cyclohexanecarbaldehyde (1) is treated with $H_2NOH$, .HCl, and $Et_3N$ in $CH_2Cl_2$ at ambient temperature for 2 hours. The resulting intermediate is further treated with HCl and oxone in 1,4-dioxane and DMF at ambient temperature for 5 hours to afford 2. Isoxazole 3 is formed by treating 2 with 2,4-pentanedione and $Et_3N$ in EtOH at 70° C. for 12–18 hours. The resulting isoxazole compound 3 is treated with methylcarbonate to afford compound 4 which is then treated with dimethylformamide-dimethylacetal 70° C. for 12–18 hours to afford the enamine derivative 5. In step (f), the enamine derivative 5 is combined with dimethoxyphenyl guanidine and NaOMe in MeOH at 85° C. for 12–18 hours to afford the desired compound IIIb-23.

Using the ester compound IIIb-23 as a starting material, compounds with a variety of $R^1$ groups are obtained as depicted in Scheme II below.

Scheme II

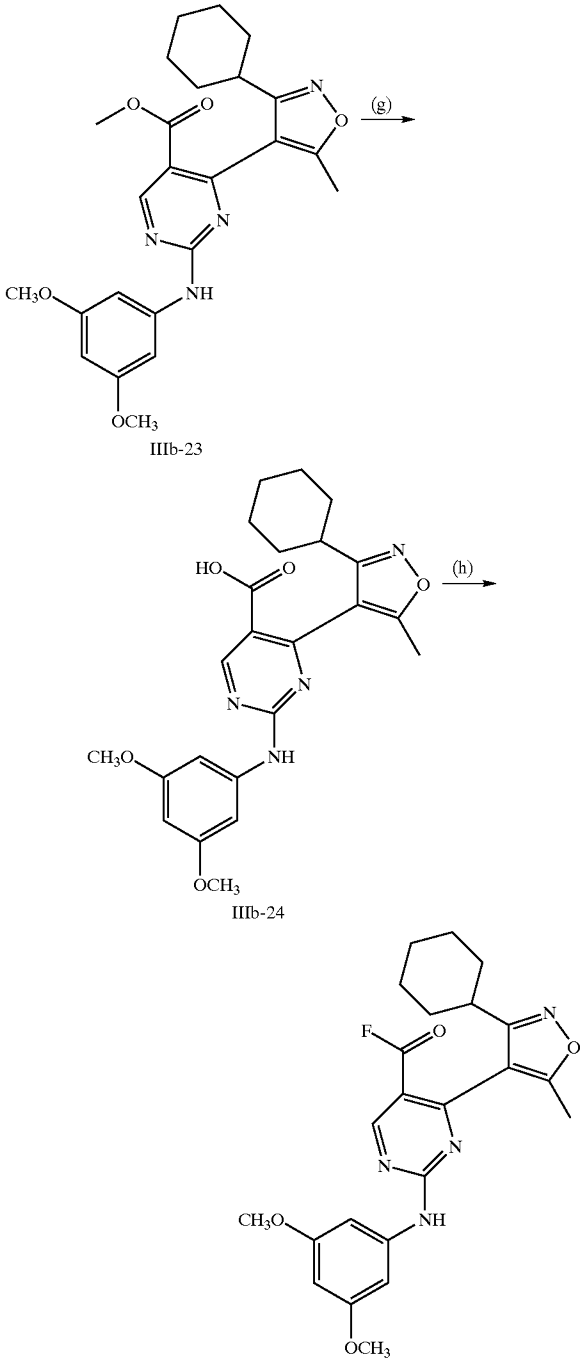

IIIb-23
IIIb-24
6

-continued

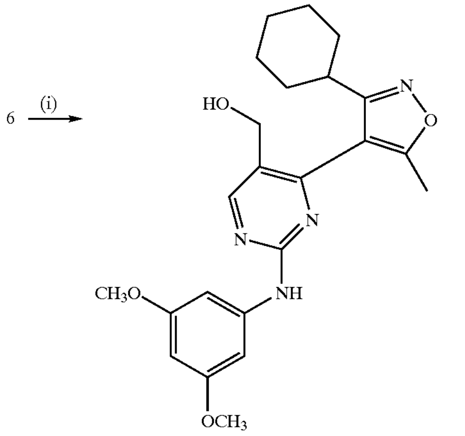

IIIb-25

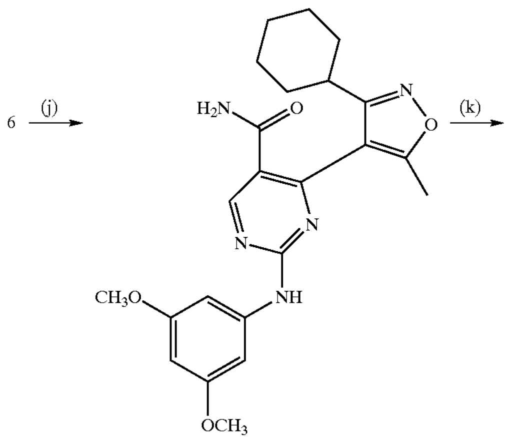

IIIb-26

-continued

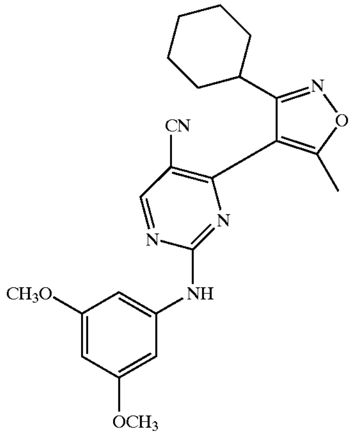

IIIb-27

Reagents and conditions: (g) NaOH, MeOH, reflux, 30 minutes; (h) pyr idine, cyanuric fluoride, THF, -20° C.; (i) $NaBH_4$, MeOH, THF; (j) $NH_4OAc$, acetone; (k) $POCl_3$, benzene, reflux, 15 hours.

Scheme II above shows how compounds with a variety of $R^1$ substituents are prepared from ester compound IIIb-23. In step (g), the $R^1$ ester group is hydrolyzed with sodium hydroxide in methanol to form the free acid compound IIIb-24. By treating compound IIIb-24 with cyanuric fluoride, the acyl fluoride intermediate 6 is prepared then utilized to prepare the hydroxy methyl compound IIIb-25 by reduction of 6 with sodium borohydride. Compound 6 is also utilized to prepare the amide compound IIIb-26 by treating 6 with ammonium acetate in acetone. Compound IIIb-26 is then treated with $POCl_3$ in benzene at reflux to form the cyano compound IIIb-27. Other compounds wherein $R^1$ is other than hydrogen may be prepared by methods substantially similar to those described above in Schemes I and II.

Scheme III

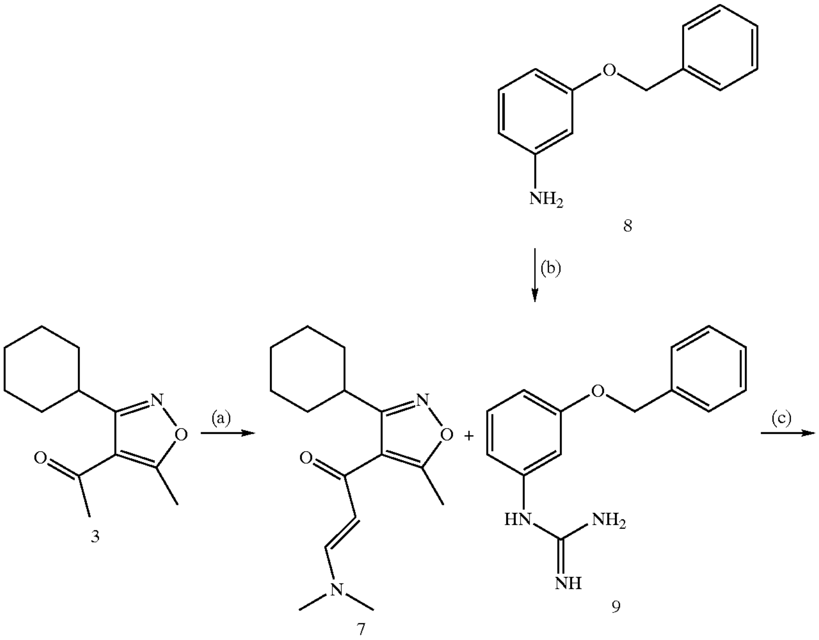

-continued

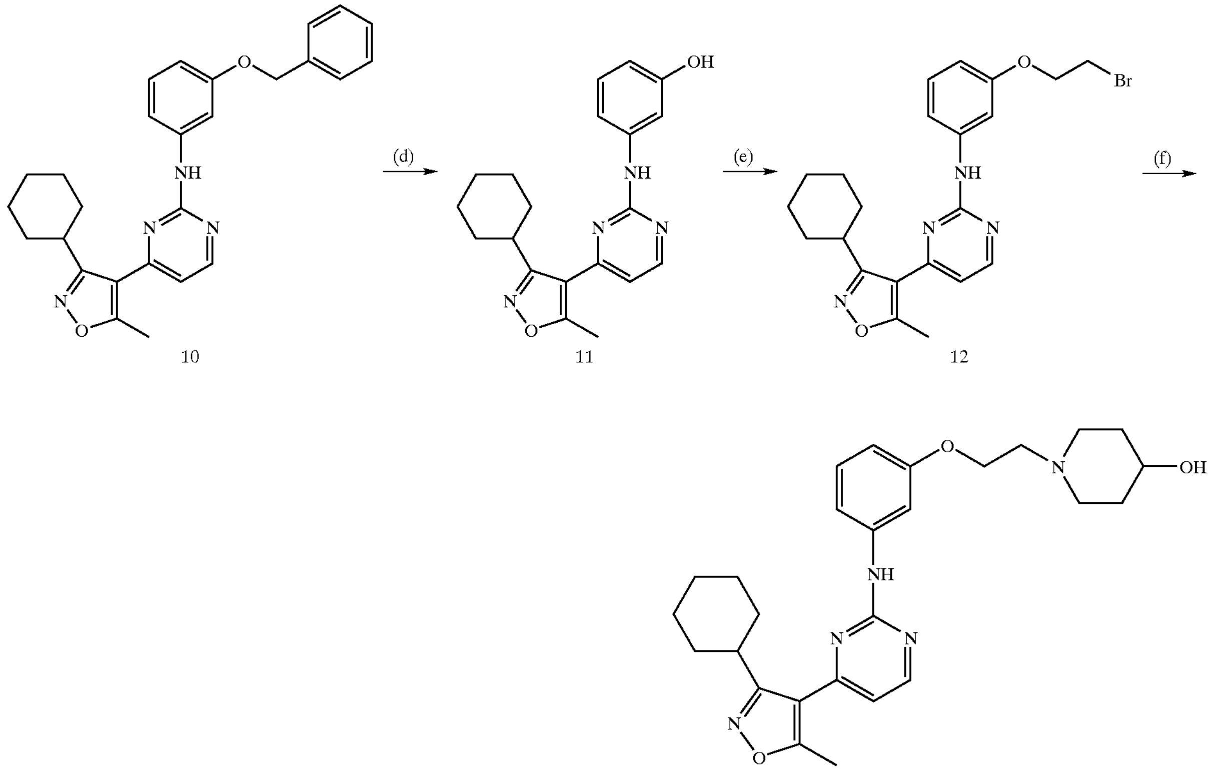

10 11 12

IIIa-5

Reagents and conditions: (a) DMF-DMA, THF, 70° C., 12–18 hours; (b) Dioxane, cyanamide, HCl, 80° C. , 12–18 hours; (c) MeOH, NaOMe, 85° C., 12–18 hours; (c) MeOH, NaOMe, 85° C., 12–18 hours; (d) Ethano l, ammonium formate, Pd/C, room temperature, 12–18 hous; (e) DEAD, THF , $PPh_3$, 2-bromoethanol, 0° C. → room temperature, 4 hours; (f) piperidin-4-ol, $CH_3CN$, 60° C., 5 hours.

Using compound IIIa-5 as an example, Scheme III above shows-a general synthetic route that may be used for preparing compounds of formula IIIa. The starting isoxazole 3 may be obtained by the methods illustrated in steps (a) through (c) of Scheme I as shown above. Isoxazole 3 is treated with dimethylformamide-dimethylacetal (DMF-DMA) in THF at 70° C. overnight. The reaction mixture is cooled then, after aqueous work-up, purified by column chromatography to afford the enaminone 7.

The aryl guanidine 9 is prepared from 3-benzyloxyphenylamine (8) by treating 8 with cyanamide in dioxane with HCl. The resulting aryl guanidine 9 is then combined with the enaminone 7 in methanol with sodium methoxide to afford the pyrimidine compound 10 after aqueous work-up and purification. The benzyl group on 10 is removed by transfer hydrogenation using ammonium formate in the presence of palladium on carbon to afford the phenol 11. The phenol 11 may be further derivatized, by methods well known to one of ordinary skill in the art, to afford a variety of compounds of formula IIIa. For example, as shown in Scheme III above, the phenol 11 is coupled with 2-bromoethanol under Mitsonobu conditions to afford the bromo derivative 12. The bromo derivative 12 may be used to alkylate a variety of groups to afford various compounds of formula IIIa, such as the piperidin-4-ol shown above to afford IIIa-5. The details of the conditions used to produce compound IIIa-5 as described above are set forth in the Examples below.

Scheme IV

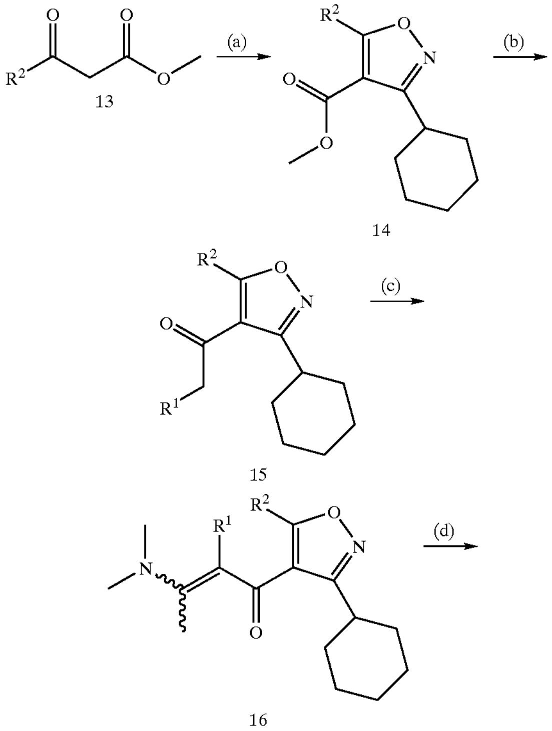

13 14 15 16

-continued

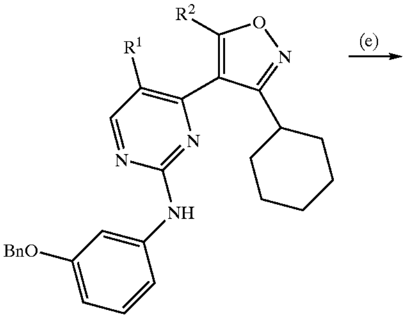

17

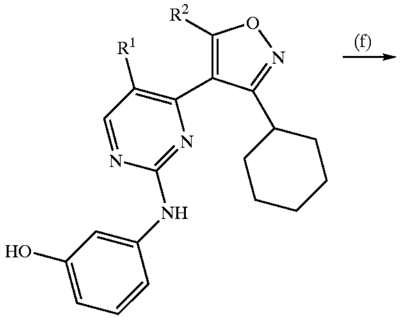

18

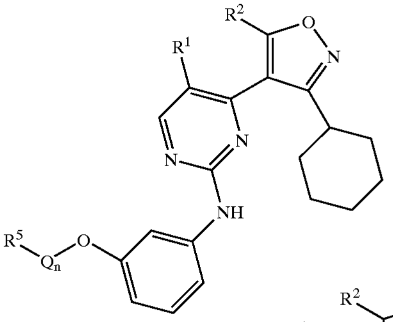

OR

19

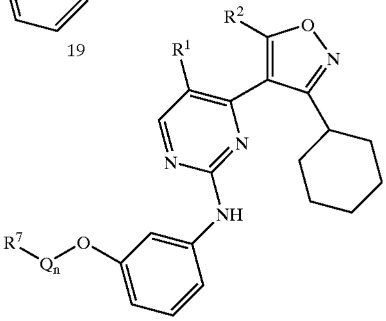

20

Reagents and conditions: (a) Compound 2, $Et_3N$, EtOH; (b) $R^1CH_2MgBr$, $Et_3N$, $Et_2O$; (c) DMF-DMA; (d) Compound 9, MeOH, NaOMe; (e) Pd/C, ammonium formate, Et OH; (f) DEAD, THF, $PPh_3$, $R^5Q_nOH$ or $R^7Q_nOH$.

Scheme IV above depicts a general method for preparing compounds of formula Ia wherein $R^1$ is other than hydrogen. As shown above, the isoxazole intermediate 14 is prepared by combining compound 2 with an ester of formula 13. The ester 14 is then treated with a Grignard reagent in ether to afford compound 15. Compound 15 is treated with dimethylformamide-dimethylacetal to form the enaminone 16 which is coupled with guanidine derivative 9 to afford the pyrimidine compound 17. The pyrimidine derivative 17 is then subjected to transfer hydrogenation conditions to remove the benzyl protecting group to afford the alcohol 18. Compound 18 may then coupled to a wide variety of $Q_nR^5$ or $Q_nR^7$ groups to afford compounds 19 and 20. Scheme IV is amenable to preparing compounds with a variety of $R^1$, $R^2$, $R^5$, and $R^7$ groups. Modifications to the method described by Scheme IV may be required to prepare certain compounds of formula Ia and are well known to those skilled in the art.

Scheme V

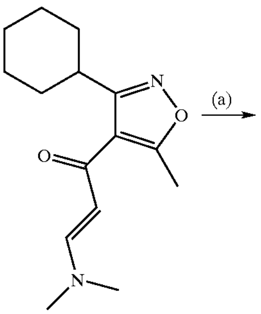

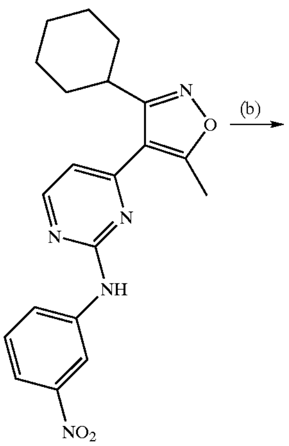

7 21

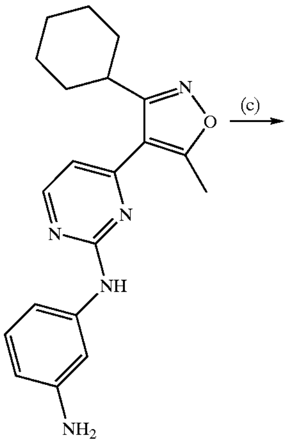

22

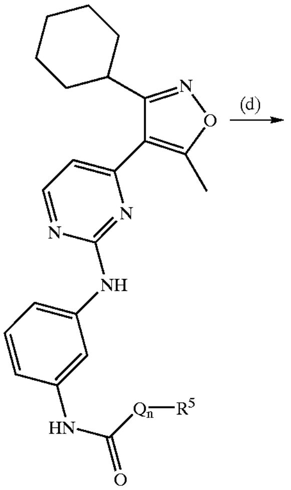

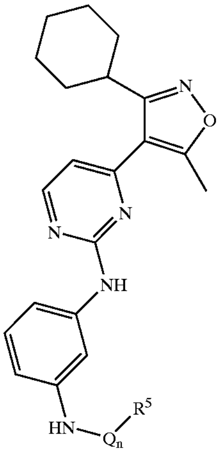

23 24

Reagents and conditions: (a) 3-$NO_2$-phenyl guanidine, $K_2CO_3$, DMF; (b) Pd/C, $H_2$, MeOH; (c) $R^5Q_nCO_2H$, EDC, HOBt, DIPEA, $CH_2Cl_2$; (d) R—C(O)H, $NaCNBH_3$, MeOH.

Scheme V above shows a general method that may be used to prepare compounds of formulae IVa and Va. In this method compound 7, as described in Scheme III above, is coupled with 3-nitrophenyl guanidine in the usual manner to afford pyrimidine compound 21. The nitro-group is then reduced using hydrogenation conditions to afford the amino compound 22. The amino compound 22 may then be coupled to an acid using standard coupling conditions known to those skilled in the art. The coupling conditions depicted above at step (c) are exemplified using 1-(3-dimethylaminopropyl)-3-ethylcarbodiimide hydrochloride (EDC) in the presence of hydroxybenztriazole (HOBt) and diisopropylethylamine (DIPEA) in $CH_2Cl_2$ to afford the amide compound 23 of formula Va. The amide 23 may then be subjected to the reductive amination conditions of step (d) to afford compound 24 of formula IVa.

Scheme VI

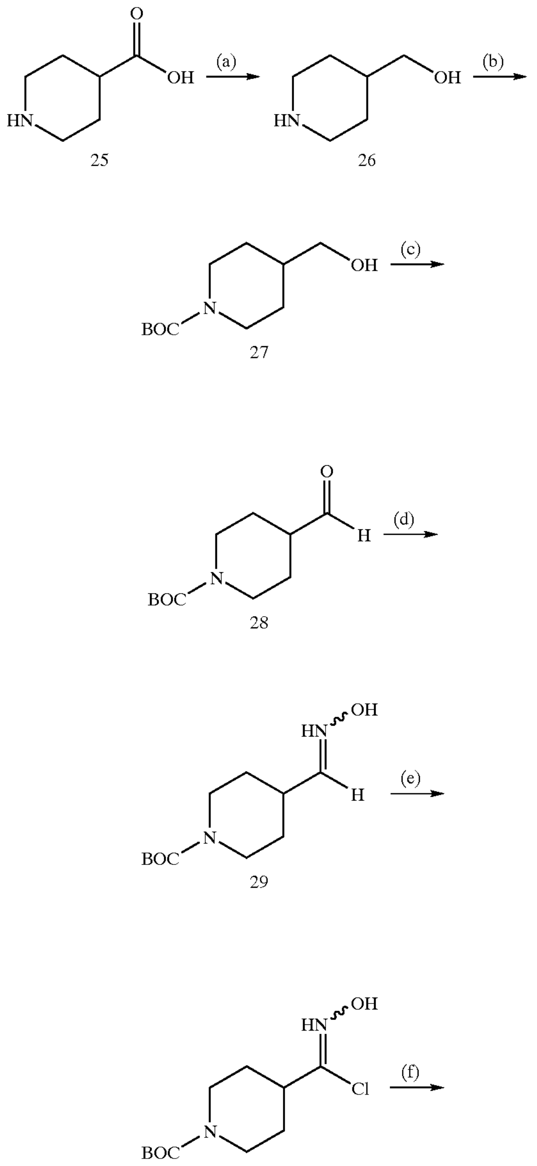

25, 26, 27, 28, 29, 30

-continued

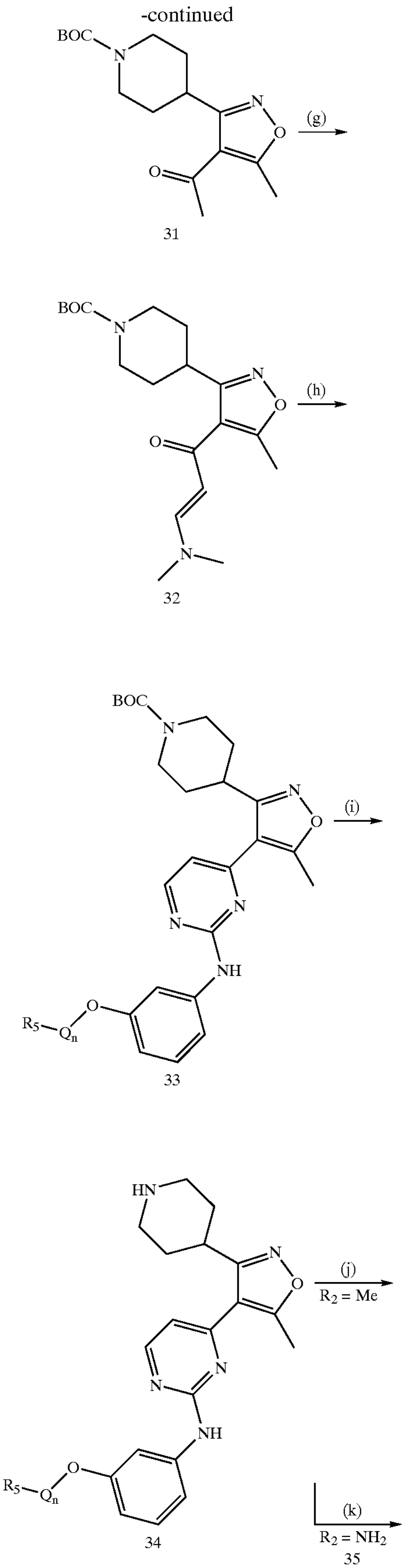

31, 32, 33, 34, 35

-continued

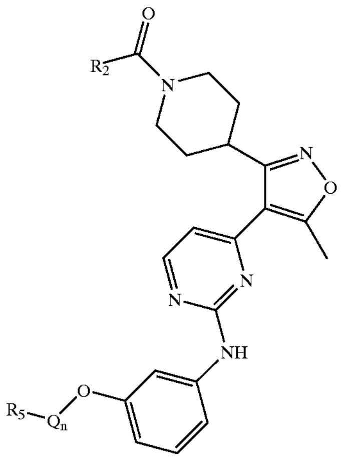

36

Reagents and conditions: (a) $LiBH_4$, TMS-Cl, THF; (b) BOC-anhydride, NaOH, t-BuOH, water; (c) oxalyl chloride, DMSO, $Et_3n$, $CH_2Cl_2$; (d) $H_2NOH$•HCl, $Et_3N$, $CH_2Cl_2$; (e) NCS, $CH_2Cl_2$; (f) 2,4-pentanedionone, $Et_3N$, EtOH; (g) DMF-DMA; (h) 3-OBn-phenyl guanidine, NaOMe, MeOH;
(i) HCl, dioxane; (j) acetic anhydride, pyridine; (k) phosgene, $NH_4OH$.

Scheme VI above depicts a general method for preparing compounds of formula IIIa wherein $R^2$ is a nitrogen-containing heterocyclic ring such as piperidine, as shown.

The activity of a compound utilized in this invention as an inhibitor of Lck or Src protein kinase may be assayed in vitro, in vivo or in a cell line according to methods known in the art. In vitro assays include assays that determine inhibition of either the phosphorylation activity or ATPase activity of activated Lck or Src. Alternate in vitro assays quantitate the ability of the inhibitor to bind to Lck or Src. Inhibitor binding may be measured by radiolabelling the inhibitor prior to binding, isolating the inhibitor/Lck or inhibitor/Src complex and determining the amount of radio-label bound. Alternatively, inhibitor binding may be determined by running a competition experiment where new inhibitors are incubated with Lck or Src bound to known radioligands. Detailed conditions for assaying a compound utilized in this invention as an inhibitor of Lck or Src kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly Lck or Src in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in Lck or Src activity between a sample comprising said composition and a Lck or Src kinase and an equivalent sample comprising Lck or Src kinase in the absence of said composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of Lck or Src kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+ (C_{1-4} alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition in a monotherapy, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting Lck or Src kinase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Lck or Src kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of a Lck- or Src-mediated disease or condition in a patient comprising the step of administering to said patient a composition according to the present invention.

The term "Src-mediated or Lck-mediated disease", as used herein means any disease or other deleterious condition in which Src or Lck is known to play a role. Accordingly, these compounds are useful for treating diseases or conditions that are known to be affected by the activity of one or more Src-family kinases. Such diseases or conditions include hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. Diseases that are affected by Lck activity, in particular, include autoimmune diseases, allergies, rheumatoid arthritis, and leukemia.

A preferred embodiment relates to the method used to treat or prevent a Src- or Lck-mediated disease selected from hypercalcemia, osteoperosis, osteoarthritis, or sympomatic treatment of bone metastasis.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLES

Example 1

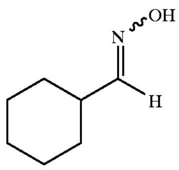

Cyclohexanecarbaldehyde oxime: To a solution of cyclohexanecarbaldehyde (4 ml, 33.02 mmol) in $CH_2Cl_2$ (100 ml) at room temperature was added hydroxylamine hydrochloride (2.76 g, 39.62 mmol) followed by $Et_3N$ (5.52 ml, 39.62 mmol) and the reaction was stirred overnight. The resulting mixture was partitioned between $CH_2Cl_2$ and $H_2O$ and the layers were separated. The organic layer was dried over $Na_2SO_4$, concentrated in vacuo and used directly for the next step. $^1H$ NMR ($CDCl_3$) δ 1.0–2.0 (m, 10H), 3.0 (m, 1H), 6.6 (d, 0.5H), 7.4 (d, 0.5H), 8.2 (bs, 1H).

Example 2

2

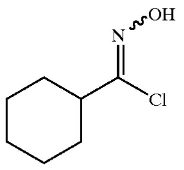

Cyclohexanecarbaldehyde chlorooxime (2): To a solution of the oxime formed in Example 1 (1 g, 8.25 mmol) in HCl (0.5 M in dioxane; 18.16 ml, 9.08 mmol) and DMF (40 ml) was added oxone (2.79 g, 4.54 mmol) and the resulting mixture was stirred overnight at room temperature. The reaction was partitioned between diethylether and water and the layers were separated. The organic layer was washed with saturated ammonium chloride, dried over sodium sulfate, then concentrates in vacuo using a room temperature water bath. The resulting low boiling liquid was carried on directly to the next step. $^1$H NMR ($CDCl_3$) δ 1.0–2.2 (m, 10H), 2.35 (m, 1H), 7.8 (bd, 1H).

Example 3

3

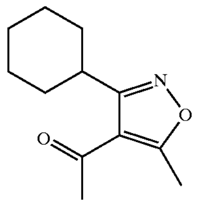

1-(3-Cyclohexyl-5-methyl-isoxazole-4-yl)-ethanone (3): To a solution of 2 and 2,4-pentanedione (0.932 ml, 9.08 mmol) in ethanol (10 ml) was added triethylamine (1.26 ml, 9.08 mmol). The resulting mixture was heated at 70° C. overnight. The reaction was partitioned between EtOAc and water and the layers were separated. The organic layer was dried over sodium sulfate then concentrated in vacuo. The crude product was purified by silica column chromatography (5% to 10% EtOAC:hexanes gradient elution) to afford compound 3 (0.633 g, 3.05 mmol) in 37% yield for 2 steps. $^1$H NMR ($CDCl_3$) δ 0.8–2.0 (m, 10H), 2.5 (s, 3H), 2.7 (s, 3H), 3.2 (m, 1H).

Example 4

7

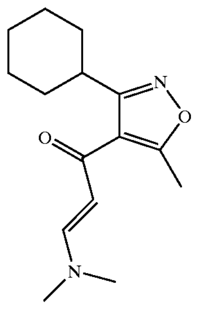

1-(3-cyclohexyl-5-methylisoxazole-4-yl)-3-dimethylamino propenone (7): To a solution of 3 (0.633 g, 3.05 mmol) in THF was added dimethylformamide-dimethylacetal (4.05 ml, 30.5 mmol) and the reaction was heated at 70° overnight. The reaction was partitioned between EtOAc and $H_2O$ and the layers were separated. The crude product was purified by silica column chromatography (10% to 20% EtOAc:hexanes, gradient elution) to afford the enaminone compound 7 (0.35 g, 1.3 mmol) in 44% yield.

Example 5

9

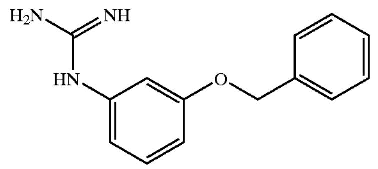

N-(3-Benzyloxy-phenyl)guanidine (9): To a suspension of 3-benzyloxy-phenylamine (20.0 g, 100.35 mmol) in 150 ml 1,4-dioxane in a 500 ml round bottom flask was added cyanamide (7.39 g, 175.95 mmol) followed by HCl in 1,4-dioxane (4M, 44 ml, 176.00 mmol). The resulting suspension was stirred and heated at 80° C. overnight. The reaction mixture was cooled to ambient temperature then NaOH (6N, 35 ml, 210.00 mmol) was added. The volume of solution was reduced to 50 ml, in vacuo, and the resulting precipitate was collected by filtration. The solid product was dried in vacuo overnight to afford the aryl guanidine 9 (23.8 g) in 98.4% yield. $^1$H NMR (MeOH-d4) δ 6.4–7.5 (m, 9H), 5.1 (s, 2H).

Example 6

10

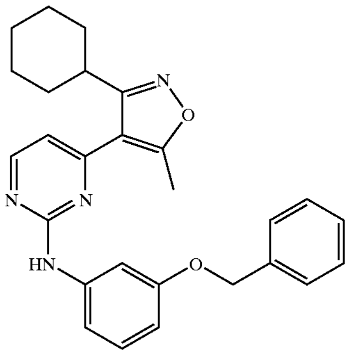

(3-Benzyloxy-phenyl)-[4-(3-cyclohexyl-5-methyl-isoxazol-4-yl)-pyrimidin-2-yl]-amime (10): To a solution of the enaminone 7 (3.5 g, 13.36 mmol) in MeOH (5 ml anhydrous), in a sealed tube, was added the aryl guanidine 9 (3.88 g, 16.03 mmol) following by sodium methoxide in methanol (0.5M, 32.06 ml, 17.03 mmol). The resulting mixture was stirred and heated at 85° C. overnight. The reaction was cooled to ambient temperature, and the solvent was removed in vacuo. The crude product was partitioned between $CH_2Cl_2$ and water and the layers were separated. The organic layer was dried over $Na_2SO_4$ and the solvent was removed in vacuo. The crude product was purified by silica chromatography (20% to 40% EtOAC:hexanes, gradient elution) to afford the pyrimidine compound 10 (3.25 g) in 55% yield. $^1$H NMR ($CDCl_3$) δ 1.2–2.0 (m, 10H), 2.5 (s, 3H), 3.1 (m, 1H), 5.1 (s, 2H), 6.6 (d, 1H), 6.7 (d, 1H), 7.1–7.6 (m, 9H), 8.4 (d, 1H).

Example 7

11

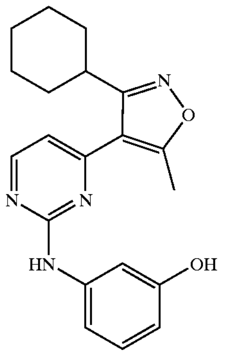

3-[4-(3-cyclohexyl-5-methyl-isoxazol-4-yl)-pyrimidin-2-ylamino]-phenol (11): To a solution of the pyrimidine 10 (1.25 g, 2.84 mmol) in ethanol (20 mL) was added ammonium formate (2.5 g, 39.64 mmol) in water (3 mL) followed by Pd/C (10 mol %, 10% weight, wet). The resulting mixture was stirred at room temperature overnight. The reaction mixture was filtered through a plug of celite and the filtrate was concentrated in vacuo. The concentrate was suspended in $CH_2Cl_2$ and the excess ammonium formate was removed by filtration. The filtrate was dried over $Na_2SO_4$ and the solvent was removed in vacuo. The crude product was purified by flashing through a short plug of silica gel using 50% EtOAC:hexanes to afford the desired phenol 11 (0.88 g) in 89% yield. $^1H$ NMR ($CDCl_3$) δ 1.2–2.0 (m, 10H), 2.5 (s, 3H), 3.1 (m, 1H), 6.5 (d, 1H), 6.7 (d, 1H), 7.0 (d, 1H), 7.2 (dd, 1H), 7.3 (bs, 1H), 7.4 (s, 1H), 8.4 (d, 1H).

Example 8

12

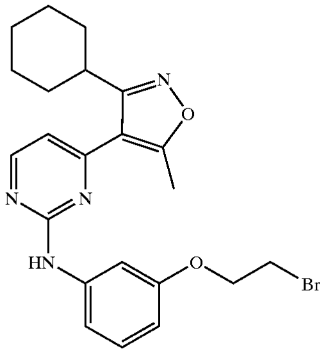

[3-(2-Bromo-ethoxy)-phenyl]-[4-(3-cyclohexyl-5-methyl-isoxazol-4-yl)-pyrimidin-2-yl]-amine (12): To a solution of phenol 11 (880 mg, 2.51 mmol) in THF (anhydrous, 5 ml) was added diethyl azodicarboxylate (0.52 ml, 3.27 mmol) and triphenylphosphine (857 mg, 3.27 mmol) followed by 2-bromoethanol (0.23 ml, 3.27 mmol) at 0° C. The resulting mixture was stirred at room temperature for 4 hours and the solvent was removed in vacuo. The crude product was purified by silica gel chromatography (30% EtOAC:hexanes) to afford the desired bromo derivative 12 (745 mg) as a white solid in 65% yield. $^1H$ NMR ($CDCl_3$) δ 1.2–2.0 (m, 10H), 2.5 (s, 3H), 3.1 (m, 1H), 3.6 (t, 2H), 4.3 (t, 2H), 6.6 (d, 1H), 6.7 (d, 1H), 7.1 (d, 1H), 7.1(s, 1H), 7.3 (dd, 1H), 7.4 (s, 1H), 8.4 (d, 1H)

Example 9

IIIa-5

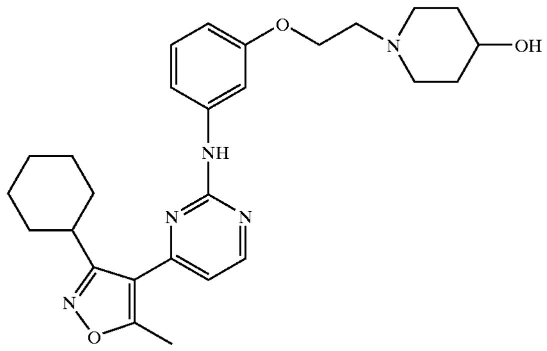

4-(2-{3-[4-(3-Cyclohexyl-5-methyl-isoxazol-4-yl-pyrimidin-2-ylamino]-phenoxy}-ethyl)-piperidin-4-ol (IIIa-5): To a solution of the bromo compound 12 (30 mg, 0.066 mmol) in acetonitrile (anhydrous, 1 mL) in a sealed tube was added piperidin-4-ol (66.3 mg, 0.66 mmol) followed by a drop of triethylamine. The reaction was heated at 60° C. for 5 hours. The reaction was cooled to room temperature and the solvent was removed in vacuo. The concentrate was partitioned between $CH_2Cl_2$ and water and the layers were separated. The organic layer was dried over $Na_2SO_4$ and the solvent was removed in vacuo. The crude product was purified by silica gel chromatography (5% MeOH:$CH_2Cl_2$) to afford IIIa-5 (24 mg) in 76% yield. $^1H$ NMR ($CDCl_3$) δ 1.2–2.0 (m, 14H), 2.3 (m, 2H), 2.5 (s, 3H), 2.8 (t, 2H), 2.9 (m, 2H), 3.1 (m, 1H), 3.7 (m, 1H), 4.1 (t, 2H), 6.6 (d, 1H), 6.7 (d, 1H), 7.1 (d, 1H), 7.2(s, 1H), 7.2 (dd, 1H), 7.3 (s, 1H), 8.4 (d, 1H)

Example 10

We have prepared other compounds of formula Ia by methods substantially similar to those described in the above Examples 1–9 and those illustrated in Schemes I–VI. The characterization data for these compounds is summarized in Table 8 below and includes M+1 (observed), HPLC, and $^1$HNMR data, wherein the term "Y" designates that the $^1$HNMR data was obtained and found to be consistent with the assigned structure. The term "$R_t$" refers to the retention time, in minutes, obtained for the compound using either HPLC method A or B as shown, wherein HPLC methods A and B are as described below:

HPLC Method A:

Column: YMC ODS-AQ, 3×100 mm

Gradient: 10% *90% $CH_3CN$/water (0.1% TFA) over 5 minutes; 90% $CH_3CN$/water (0.1% TFA) for 0.7 minutes; 90% *10% $CH_3CN$/water (0.1% TFA) over 0.1 minutes; and then 10% $CH_3CN$/water (0.1% TFA) for 1.2 minutes Flow rate: 1.0 ml/min Method B:

Column: YMC ODS-AQ, 3×150 mm

Gradient: 10% *90% $CH_3CN$/water (0.1% TFA) over 7 minutes; 90% $CH_3CN$/water (0.1% TFA) for 2.0 minutes; 90% *10% $CH_3CN$/water (0.1% TFA) over 1.0 minutes; and then 10% $CH_3CN$/water (0.1% TFA) for 2.0 minutes Flow rate: 1.0 mL/minute.

Compound numbers correspond to the compound numbers listed in Tables 1–7.

TABLE 8

| Characterization Data for Selected Compounds of Formula Ia | | | |
|---|---|---|---|
| Compound No | M + H (obs) | $R_t$/Method | $^1$H NMR |
| IIa-2 | 464 | 6.08/B | Y |
| Va-1 | 489 | 2.48/A | Y |
| IIIa-1 | 479 | 7.90/B | Y |
| IIIa-2 | 464 | 6.027/B | Y |
| IIIa-3 | 448 | 6.08/B | Y |
| IIIa-4 | 462 | 6.28/B | Y |
| IIIa-5 | 478 | 5.90/B | Y |
| IIIa-6 | 492 | 6.02/B | Y |
| IIIa-7 | 478 | 6.08/B | Y |
| IIIa-8 | 507 | 5.60/B | Y |
| IIIa-9 | 492 | 6.01/B | Y |
| IIIa-10 | 506 | 6.09/B | Y |
| IIIa-11 | 492 | 6.13/B | Y |
| IIIa-12 | 521 | 2.23/A | Y |
| IIIa-13 | 492 | 2.52/A | Y |
| IIIa-14 | 505 | 2.25/A | Y |
| IIIa-15 | 478 | 2.53/A | Y |
| IIIa-16 | 462 | 2.62/A | Y |
| IIIa-17 | 476 | 2.70/A | Y |
| IIIa-18 | 477 | 4.96/B | Y |
| IIIa-20 | 506 | 2.52/A | Y |
| IIIa-21 | 520 | 2.55/A | Y |
| IIIa-27 | 466 | 5.12/B | Y |
| IIIa-32 | 469 | 5.32/A | Y |
| IIIa-34 | 435.3 | 4.32/B | Y |
| IIIa-35 | 449.3 | 4.46/B | Y |

The following examples demonstrate how the compounds of this invention were tested as inhibitors of Src and Lck kinases.

Example 11

The compounds were evaluated as inhibitors of human Src kinase using either a radioactivity-based assay or spectrophotometric assay.

Src Inhibition Assay A: Radioactivity-Based Assay

The compounds were assayed as inhibitors of full length recombinant human Src kinase (from Upstate Biotechnology, cat. no. 14-117) expressed and purified from baculo viral cells. Src kinase activity was monitored by following the incorporation of $^{33}$P from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 $\mu$M ATP (1–2 $\mu$Ci $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with $^{33}$P-ATP. After 20 minutes of reaction, the reactions were quenched with 150 $\mu$l of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 $\mu$l of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the Ki for the compound.

Src Inhibition Assay B: Spectrophotometric Assay

The ADP produced from ATP by the human recombinant Src kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM MgCl2, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 $\mu$M NADH, 30 $\mu$g/ml pyruvate kinase and 10 $\mu$g/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with 100 $\mu$M ATP. The absorbance change at 340 nm with time, the rate of the reaction, was monitored on a molecular devices plate reader. The data of rate as a function of the inhibitor concentration was fitted to compettive inhibition kinetics model to get the Ki for the compound.

The following compounds provided a $K_i$ of less than 0.1 micromolar in the Src inhibition assay: IIIa-1, IIIa-2, IIIa-3, IIIa-4, IIIa-5, IIIa-6, IIIa-7, IIIa-8, IIIb-28, and Va-1. The compound numbers correspond to the compound numbers in Tables 1–7.

Example 12

The compounds were evaluated as inhibitors of human Lck kinase using either a radioactivity-based assay or spectrophotometric assay.

Lck Inhibition Assay A: Radioactivity-Based Assay

The compounds were assayed as inhibitors of full length bovine thymus Lck kinase (from Upstate Biotechnology, cat. no. 14-106) expressed and purified from baculo viral cells. Lck kinase activity was monitored by following the incorporation of $^{33}$P from ATP into the tyrosine of a random poly Glu-Tyr polymer substrate of composition, Glu:Tyr=4:1 (Sigma, cat. no. P-0275). The following were the final concentrations of the assay components: 0.025 M HEPES, pH 7.6, 10 mM $MgCl_2$, 2 mM DTT, 0.25 mg/ml BSA, 10 $\mu$M ATP (1–2 $\mu$Ci $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with $^{33}$P-ATP. After 20 min of reaction, the reactions were quenched with 150 $\mu$l of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the Ki for the compound.

Lck Inhibition Assay B: Spectrophotometric Assay

The ADP produced from ATP by the human recombinant Lck kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM $MgCl_2$, 2 mM DTT, 5 mg/ml poly Glu-Tyr, and 50 nM of recombinant human Lck kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 minutes before initiating the reaction with 150 μM ATP. The absorbance change at 340 nm with time, the rate of the reaction, was monitored on a molecular devices plate reader. The data of rate as a function of the inhibitor concentration was fitted to competitive inhibition kinetics model to get the Ki for the compound.

Table 10 shows the results of the activity of selected compounds of this invention in the Lck inhibition assay. The compound numbers correspond to the compound numbers in Tables 1–7. Compounds having a $K_i$ less than 0.1 micromolar (μM) are rated "A", compounds having a $K_i$ between 0.1 and 1 μM are rated "B" and compounds having a $K_i$ greater than 1 μM are rated "C".

TABLE 10

Lck Activity of Selected Compounds

| No. | Activity | No. | Activity | No. | Activity |
|---|---|---|---|---|---|
| IIIa-1 | A | IIIa-2 | A | IIIa-3 | A |
| IIIa-4 | A | IIIa-5 | A | IIIa-6 | A |
| IIIa-7 | A | IIIa-8 | A | IIIa-9 | A |
| IIIa-10 | A | IIIa-11 | A | IIIa-12 | A |
| IIIa-13 | A | IIIa-14 | A | IIIa-15 | A |
| IIIa-16 | A | IIIa-17 | A | IIIa-18 | A |
| IIIa-19 | A | IIIa-20 | A | IIIa-21 | A |
| IIIa-22 | A | IIIa-23 | A | IIIa-24 | A |
| IIIa-25 | A | IIIa-26 | A | IIIa-27 | A |
| IIIa-28 | C | IIIa-29 | A | IIIa-30 | C |
| IIIa-31 | A | — | — | — | — |
| IIIb-24 | C | IIIb-25 | C | IIIb-26 | C |
| IIIb-27 | B | IIIb-28 | A | IIIb-29 | A |
| Va-1 | A | — | — | — | — |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula IIIa:

IIIa

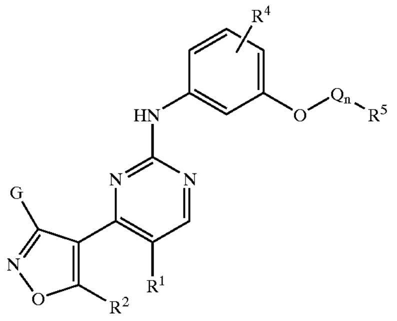

or a pharmaceutically acceptable salt thereof, wherein:

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), C(O)$CH_2$C(O), C(O)C(O), C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

Q is an optionally substituted $C_1$–$C_6$ alkylidene chain wherein:

one or two non-adjacent methylene units of Q are optionally and independently replaced by O, NR, NRC(O), C(O)NR, C(O), S, SO, $SO_2$, or $SO_2NR$;

each n is independently selected from zero or one;

$R^4$ is independently selected from R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, $R^5$ is $Ar^1$, wherein $R^5$ is optionally substituted with up to three $R^6$;

each $R^6$ is independently selected from R, halogen, $NO_2$, CN, OR, SR, $N(R)_2$, NRC(O)R, $NRC(O)N(R)_2$, $NRCO_2R$, C(O)R, $CO_2R$, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, or:

two $R^6$ on adjacent positions of $R^5$ are taken together to form a saturated, partially unsaturated, or fully unsaturated 5–7 membered ring having 0–3 heteroatoms independently selected from nitrogen, oxygen, or sulfur; and provided that when $R^1$ is hydrogen, $R^5$ is other than phenyl.

2. The compound according to claim 1, wherein:

n is one;

Q is a $C_{1-6}$ alkylidene chain wherein one or two non-adjacent methylene units of Q are optionally and independently replaced by O, NR, S, or C(O); and $R^5$ is a 5–6 membered saturated or aryl ring having 0–2 heteroatoms independently selected from nitrogen, oxygen, or sulfur, wherein said ring is optionally substituted with up to two $R^6$ groups.

3. A compound of formula IIIb:

IIIb

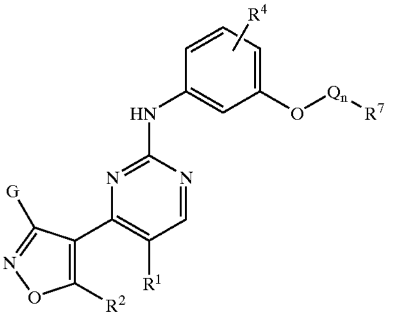

or a pharmaceutically acceptable salt thereof, wherein:

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), C(O)$CH_2$C(O), C(O)C(O), C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

Q is a $C_{1-6}$ alkylidene chain wherein one or two non-adjacent methylene units of Q are optionally and independently replaced by O, NR, S, or C(O);

n is one;

each $R^4$ is independently selected from R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, $R^7$ is selected from OR, $N(R)_2$, OC(O)R, $CO_2R$, $C(O)N(R)_2$, NRC(O)OR, or NRC(O)R.

4. A compound of formula IVa:

IVa

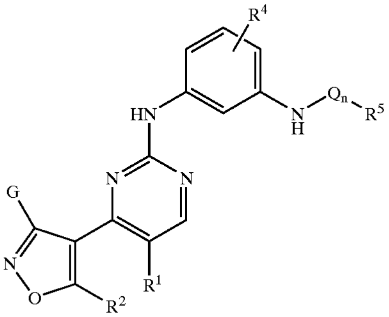

or a pharmaceutically acceptable salt thereof, wherein:

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), C(O)$CH_2$C(O), C(O)C(O), C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

Q is an optionally substituted $C_1$–$C_6$ alkylidene chain wherein:

one or two non-adjacent methylene units of Q are optionally and independently replaced by O, NR, NRC(O), C(O)NR, C(O), S, SO, $SO_2$, or $SO_2NR$;

each n is independently selected from zero or one;

each $R^4$ is independently selected from R, halogen, $NO_2$, CN, OR, SR, $N(R)_2$, NRC(O)R, NRC(O)N(R)$_2$, $NRCO_2R$, C(O)R, $CO_2R$, OC(O)R, C(O)N(R)$_2$, OC(O)N(R)$_2$, SOR, $SO_2R$, $SO_2N(R)_2$, $NRSO_2R$, $NRSO_2N(R)_2$, C(O)C(O)R, or C(O)$CH_2$C(O)R, $R^5$ is $Ar^1$, wherein $R^5$ is optionally substituted with up to three $R^6$;

each $R^6$ is independently selected from R, halogen, $NO_2$, CN, OR, SR, $N(R)_2$, NRC(O)R, NRC(O)N(R)$_2$, $NRCO_2R$, C(O)R, $CO_2R$, C(O)N(R)$_2$, OC(O)N(R)$_2$, SOR, $SO_2R$, $SO_2N(R)_2$, $NRSO_2R$, $NRSO_2N(R)_2$, C(O)C(O)R, or C(O)$CH_2$C(O)R, or:

two $R^6$ on adjacent positions of $R^5$ are taken together to form a saturated, partially unsaturated, or fully unsaturated 5–7 membered ring having 0–3 heteroatoms independently selected from nitrogen, oxygen, or sulfur; and provided that when $R^1$ is hydrogen, $R^5$ is other than phenyl.

5. The compound according to claim 4, wherein:

n is one;

Q is a $C_{1-6}$ alkylidene chain wherein one or two non-adjacent methylene units of Q are optionally and independently replaced by O, NR, S, or C(O); and $R^5$ is a 5–6 membered saturated or aryl ring having 0–2 heteroatoms independently selected from nitrogen, oxygen, or sulfur, wherein said ring is optionally substituted with up to two $R^6$ groups.

6. A compound of formula IVb:

IVb

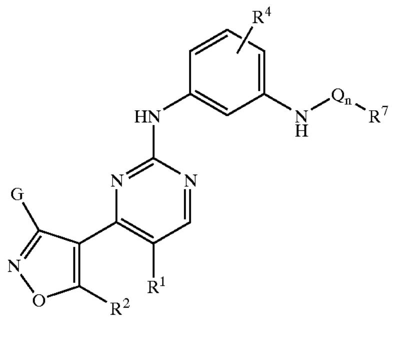

or a pharmaceutically acceptable salt thereof, wherein:

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), C(O)$CH_2$C(O), C(O)C(O), C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

Q is a $C_{1-6}$ alkylidene chain wherein one or two non-adjacent methylene units of Q are optionally and independently replaced by O, NR, S, or C(O);

n is one;

$R^4$ is independently selected from R, halogen, $NO_2$, CN, OR, SR, $N(R)_2$, NRC(O)R, NRC(O)N(R)$_2$, $NRCO_2R$, C(O)R, $CO_2R$, OC(O)R, C(O)N(R)$_2$, OC(O)N(R)$_2$, SOR, $SO_2R$, $SO_2N(R)_2$, $NRSO_2R$, $NRSO_2N(R)_2$, C(O)C(O)R, or C(O)$CH_2$C(O)R, $R^7$ is selected from OR, $N(R)_2$, OC(O)R, $CO_2R$, C(O)N(R)$_2$, NRC(O)OR, or NRC(O)R.

7. A compound of formula Va:

Va

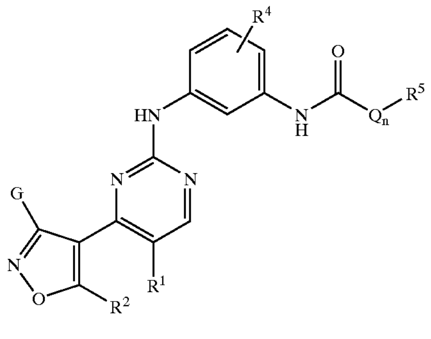

or a pharmaceutically acceptable salt thereof, wherein:

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), C(O)$CH_2$C(O), C(O)C(O), C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

Q is an optionally substituted $C_1$–$C_6$ alkylidene chain wherein:

one or two non-adjacent methylene units of Q are optionally and independently replaced by O, NR, NRC(O), C(O)NR, C(O), S, SO, $SO_2$, or $SO_2NR$;

each n is independently selected from zero or one;

$R^4$ is independently selected from R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, $R^5$ is $Ar^1$, wherein $R^5$ is optionally substituted with up to three $R^6$;

each $R^6$ is independently selected from R, halogen, $NO_2$, CN, OR, SR, $N(R)_2$, NRC(O)R, $NRC(O)N(R)_2$, $NRCO_2R$, C(O)R, $CO_2R$, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, or:

two $R^6$ on adjacent positions of $R^5$ are taken together to form a saturated, partially unsaturated, or fully unsaturated 5–7 membered ring having 0–3 heteroatoms independently selected from nitrogen, oxygen, or sulfur; and provided that when $R^1$ is hydrogen, $R^5$ is other than phenyl.

8. The compound according to claim 7, wherein:

n is one;

Q is a $C_{1-6}$ alkylidene chain wherein one or two non-adjacent methylene units of Q are optionally and independently replaced by O, NR, S, or C(O); and $R^5$ is a 5–6 membered saturated or aryl ring having 0–2 heteroatoms independently selected from nitrogen, oxygen, or sulfur, wherein said ring is optionally substituted with up to two $R^6$ groups.

9. A compound of formula Vb:

Vb

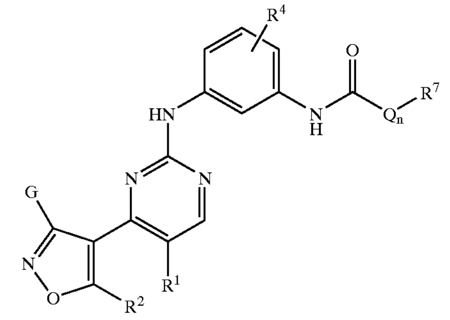

or a pharmaceutically acceptable salt thereof, wherein:

$R^1$ is selected from halogen, $NO_2$, $T_yR$, or TCN;

each T is independently selected from an optionally substituted $C_1$–$C_6$ alkylidene chain, wherein:

one methylene unit of T is optionally replaced by O, NR, NRC(O), C(O)NR, NRC(O)NR, C(O), $C(O)CH_2C(O)$, C(O)C(O), C(O)O, OC(O), $NRSO_2$, S, SO, $SO_2NR$, or $SO_2$;

y is zero or one;

each R is independently selected from hydrogen or an optionally substituted $C_1$–$C_6$ aliphatic group, or:

two R on the same nitrogen are taken together with the nitrogen to form a 3–7 membered saturated, partially unsaturated, or fully unsaturated ring having 1–2 heteroatoms, in addition to the nitrogen bound thereto, independently selected from nitrogen, oxygen, or sulfur;

$R^2$ is R or $Ar^1$;

G is selected from $X_mR$ or $X_mAr^1$;

each m is independently selected from zero or one;

X is selected from O, S, SO, $SO_2$, NH, C(O), C(O)NH, NHC(O), NHC(O)NH, $SO_2NH$, $NHSO_2$, or $NHSO_2NH$;

each $Ar^1$ is independently selected from an optionally substituted ring selected from a 5–7 membered saturated, partially unsaturated, or fully unsaturated monocyclic ring having 0–3 heteroatoms independently selected from nitrogen, oxygen, or sulfur, or an 8–10 membered saturated, partially unsaturated, or fully unsaturated bicyclic ring having 0–4 heteroatoms independently selected from nitrogen, oxygen, or sulfur;

Q is a $C_{1-6}$ alkylidene chain wherein one or two non-adjacent methylene units of Q are optionally and independently replaced by O, NR, S, or C(O);

n is one;

$R^4$ is independently selected from R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$, $R^7$ selected from OR, $N(R)_2$, OC(O)R, $CO_2R$, $C(O)N(R)_2$, NRC(O)OR, or NRC(O)R.

10. The compound according to any of claims 2, 3, 5, 6, 8, or 9, wherein:

G is $X_mR$ or $X_mAr^1$;

each m is independently zero or one;

each X is independently selected from O, S, or NH;

R is $C_{1-4}$ aliphatic; and $Ar^1$ is an optionally substituted 5–6 membered saturated or aryl ring having 0–2 heteroaroms independently selected from nitrogen, oxygen, or sulfur.

11. A compound selected from the following Table 1 compounds:
TABLE 1
Compounds of Formula II
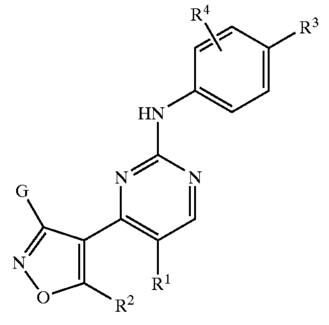
II
| No. | $R^1$ | 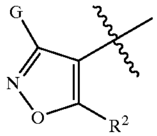 | 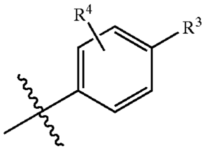 |
|---|---|---|---|
| II-1 | $CH_3$ | 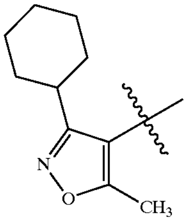 | 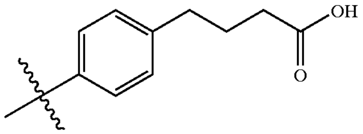 |
| II-2 | $CH_3$ | 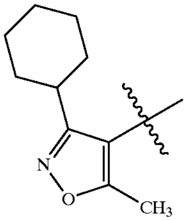 | 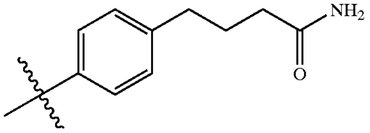 |
| II-3 | $CH_3$ | 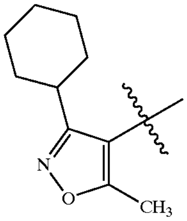 | 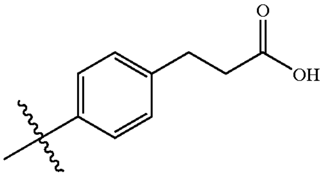 |
| II-4 | $CH_3$ | 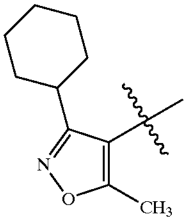 | 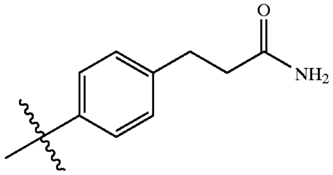 |

TABLE 1-continued
Compounds of Formula II
II
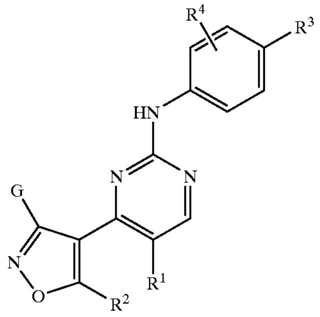
| No. | $R^1$ | 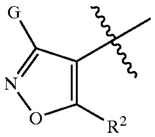 | 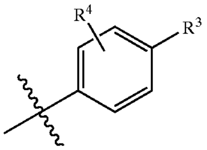 |
|---|---|---|---|
| II-5 | $CH_3$ | 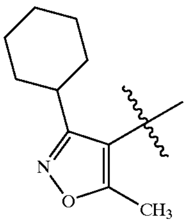 | 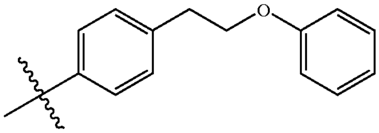 |
| II-6 | $CH_2CN$ | 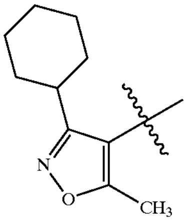 | 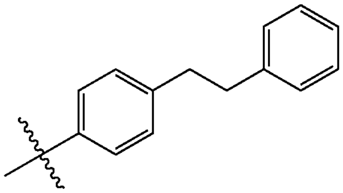 |
| II-7 | COOH | 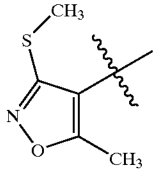 | 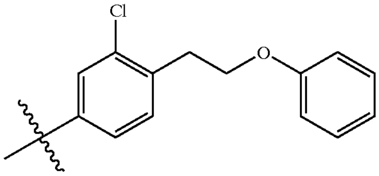 |

TABLE 1-continued
Compounds of Formula II
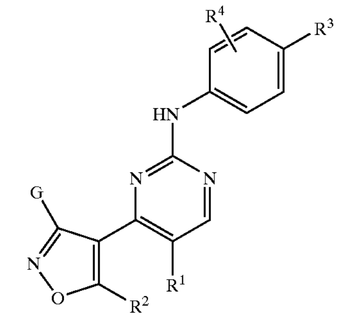
II
| No. | $R^1$ | 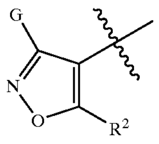 | 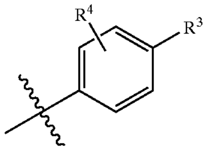 |
|---|---|---|---|
| II-8 | H | 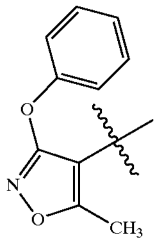 | 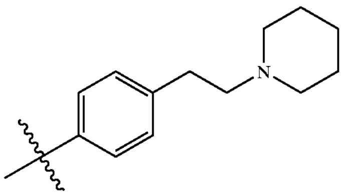 |
| II-9 | $CH_2CH_3$ | 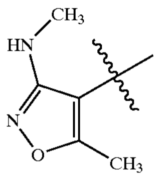 | 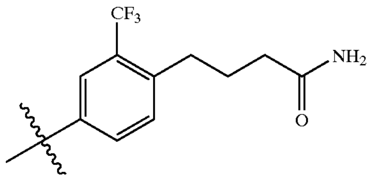 |
| II-10 | $C(O)NH_2$ | 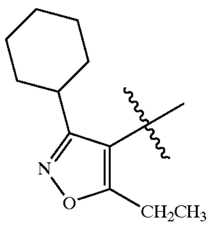 | 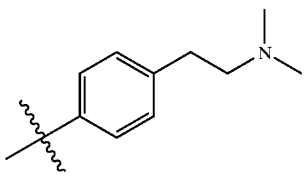 |

12. A compound selected from the following Table 2 compounds:
TABLE 2
Compounds of Formula IIIa
IIIa
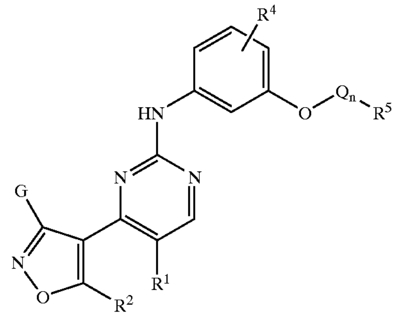
| No. | $R^1$ | 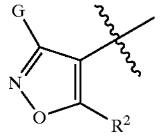 | 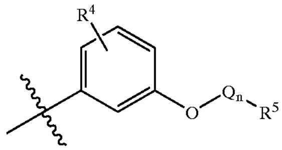 |
|---|---|---|---|
| IIIa-1 | H | 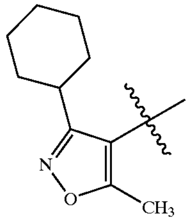 | 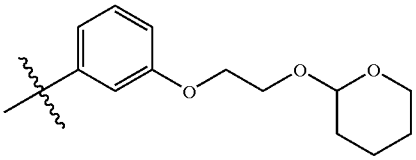 |
| IIIa-2 | H | 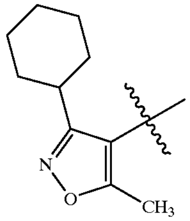 | 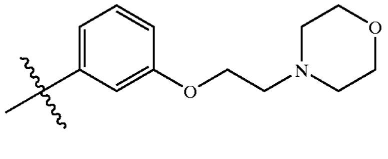 |
| IIIa-3 | H | 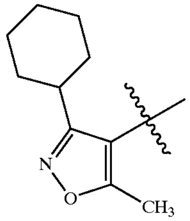 | 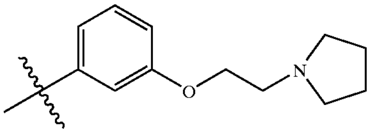 |
| IIIa-4 | H | 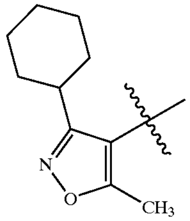 | 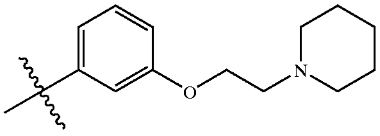 |

TABLE 2-continued
Compounds of Formula IIIa
IIIa
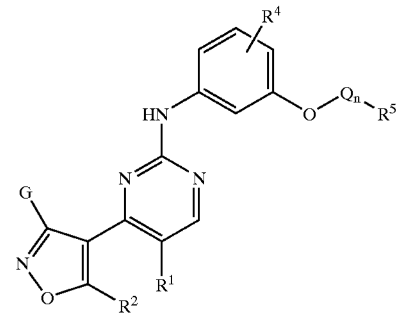
| No. | $R^1$ | 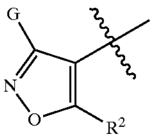 | 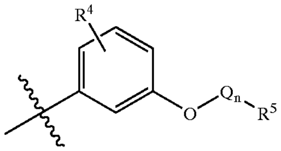 |
|---|---|---|---|
| IIIa-5 | H | 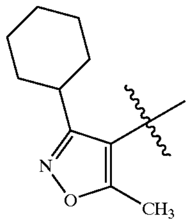 | 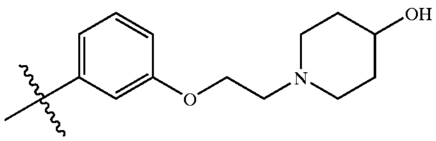 |
| IIIa-6 | H | 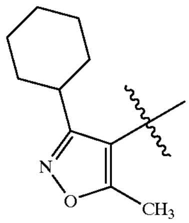 | 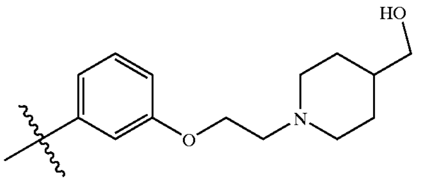 |
| IIIa-7 | H | 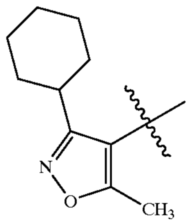 | 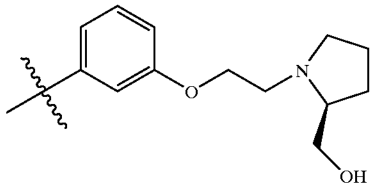 |
| IIIa-8 | H | 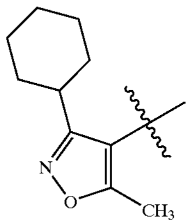 | 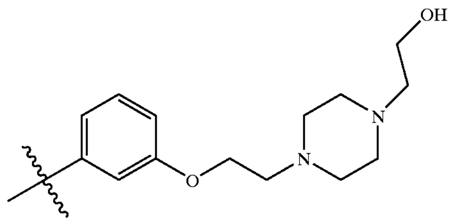 |

TABLE 2-continued
Compounds of Formula IIIa
IIIa
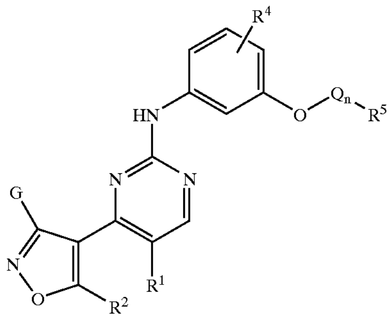
| No. | $R^1$ | 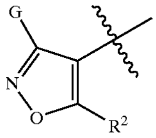 | 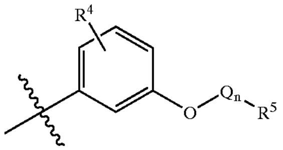 |
|---|---|---|---|
| IIIa-9 | H | 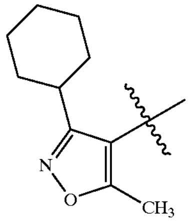 | 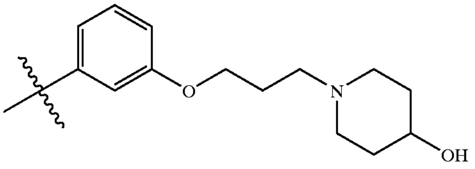 |
| IIIa-10 | H | 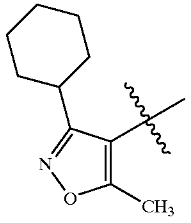 | 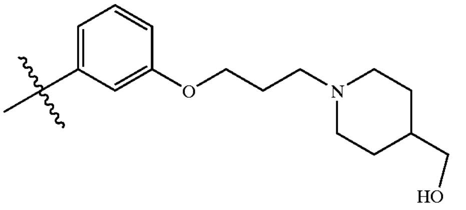 |
| IIIa-11 | H | 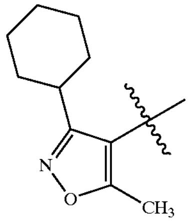 | 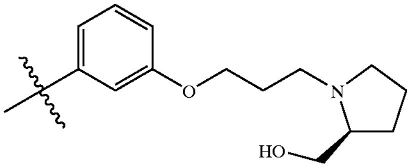 |
| IIIa-12 | H | 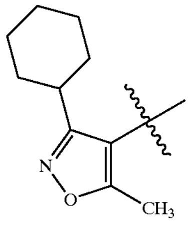 | 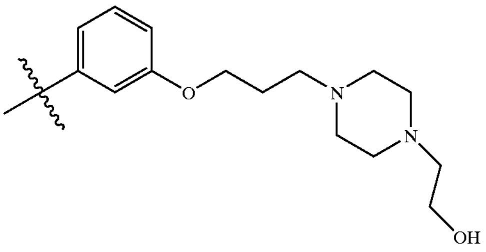 |

TABLE 2-continued
Compounds of Formula IIIa
IIIa
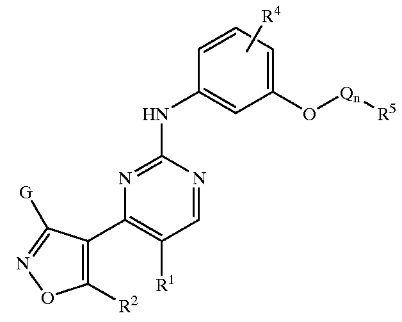
| No. | $R^1$ | 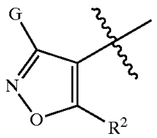 | 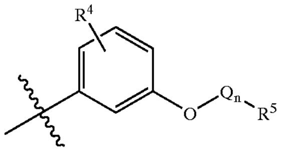 |
| --- | --- | --- | --- |
| IIIa-13 | H | 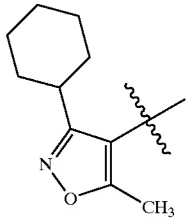 | 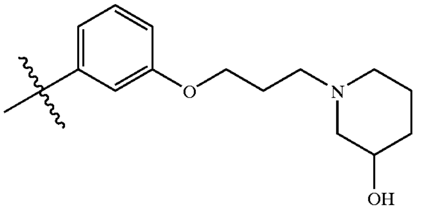 |
| IIIa-14 | H | 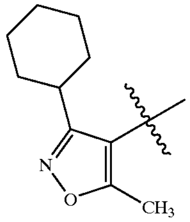 | 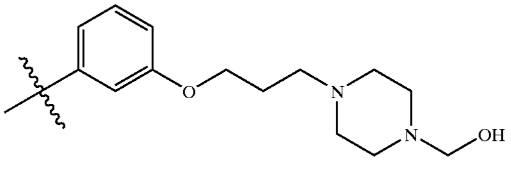 |
| IIIa-15 | H | 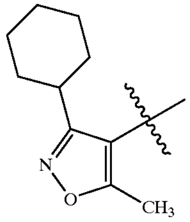 | 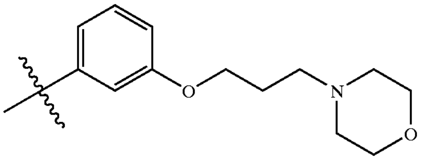 |
| IIIa-16 | H | 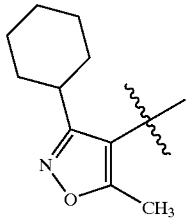 | 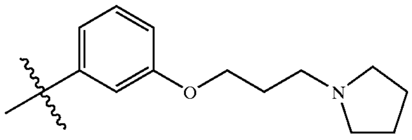 |

TABLE 2-continued
Compounds of Formula IIIa
IIIa
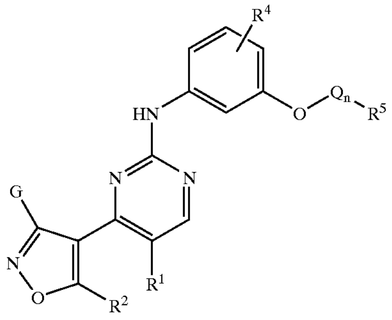
| No. | $R^1$ | 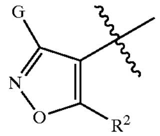 | 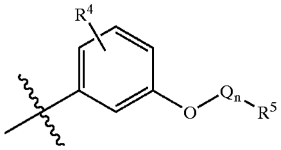 |
|---|---|---|---|
| IIIa-17 | H | 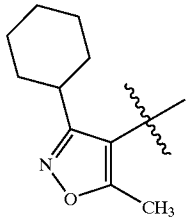 | 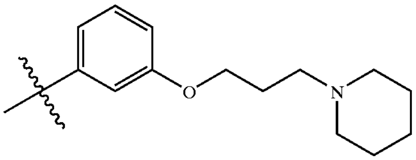 |
| IIIa-18 | H | 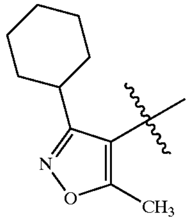 | 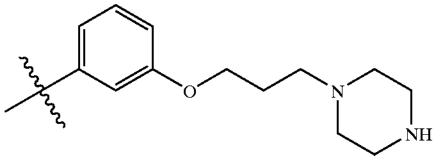 |
| IIIa-19 | H | 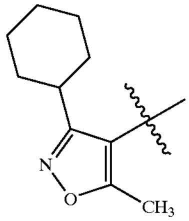 | 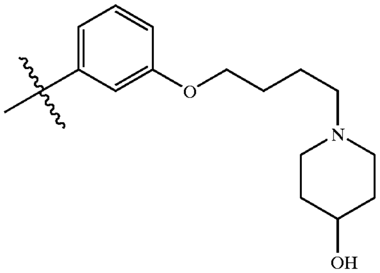 |
| IIIa-20 | H | 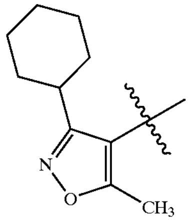 | 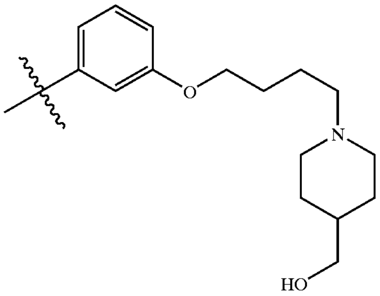 |

TABLE 2-continued
Compounds of Formula IIIa
IIIa
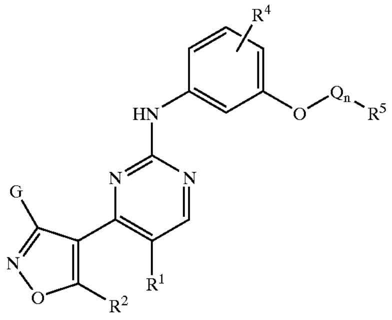
| No. | $R^1$ | 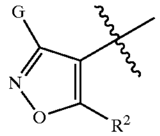 | 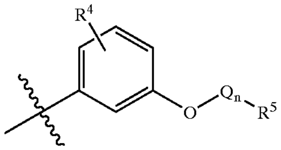 |
| --- | --- | --- | --- |
| IIIa-21 | H | 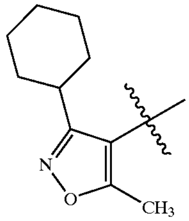 | 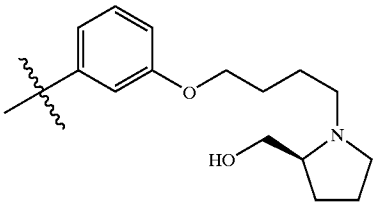 |
| IIIa-22 | H | 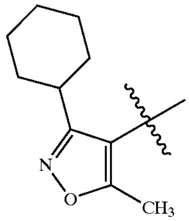 | 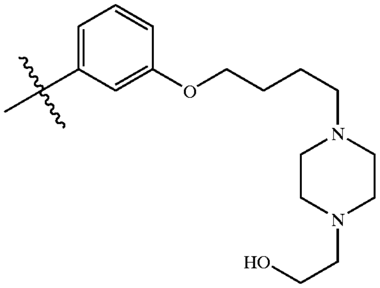 |
| IIIa-23 | H | 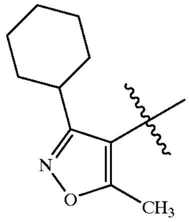 | 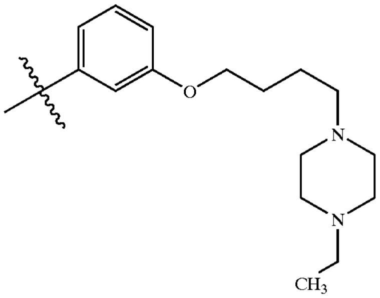 |
| IIIa-24 | H | 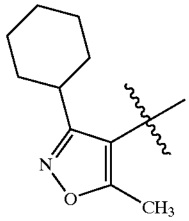 | 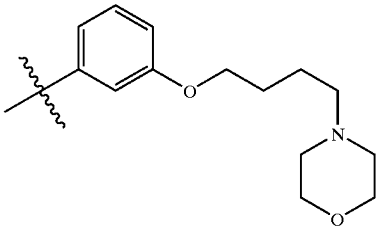 |

TABLE 2-continued
Compounds of Formula IIIa
IIIa
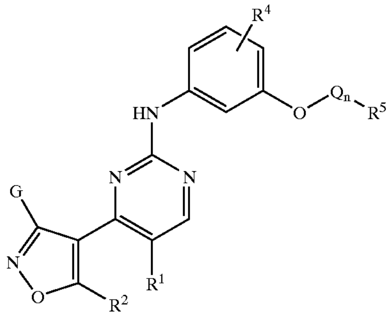
| No. | $R^1$ | 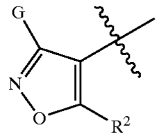 | 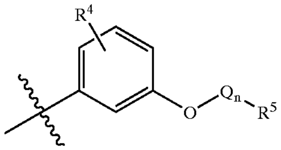 |
|---|---|---|---|
| IIIa-25 | H | 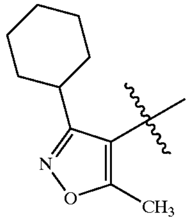 | 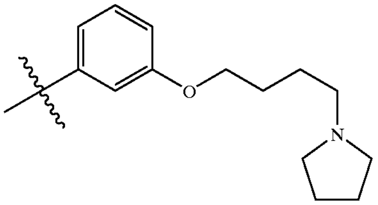 |
| IIIa-26 | H | 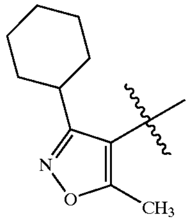 | 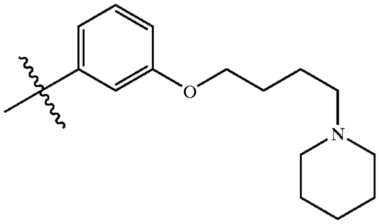 |
| IIIa-27 | H | 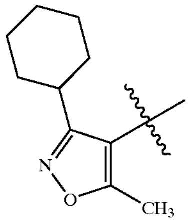 | 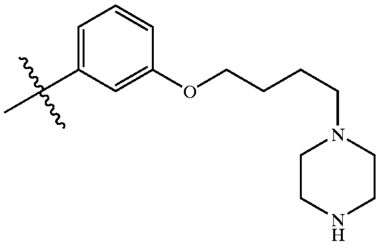 |
| IIIa-28 | H | 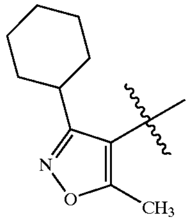 | 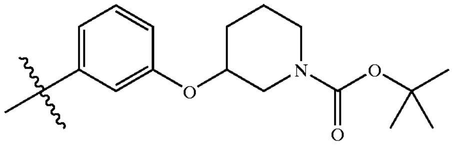 |

TABLE 2-continued
Compounds of Formula IIIa
IIIa
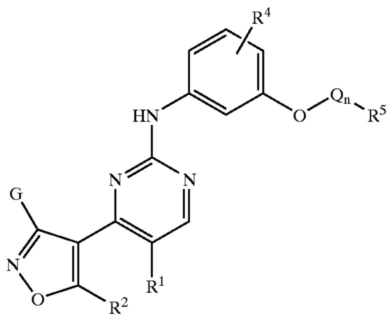
| No. | $R^1$ | 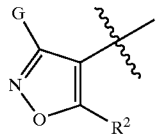 | 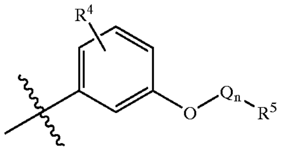 |
|---|---|---|---|
| IIIa-29 | H | 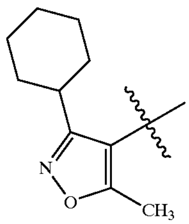 | 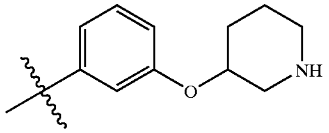 |
| IIIa-30 | H | 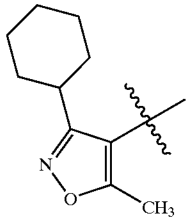 | 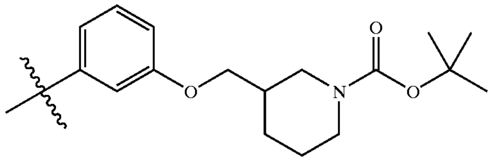 |
| IIIa-31 | H | 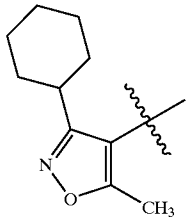 | 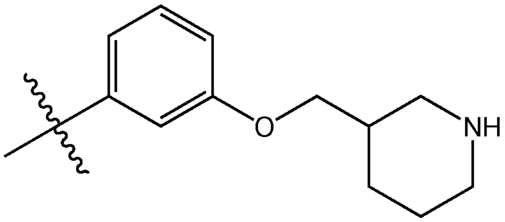 |
| IIIa-32 | $CH_3$ | 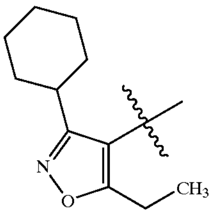 | 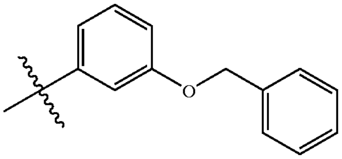 |

TABLE 2-continued
Compounds of Formula IIIa
IIIa
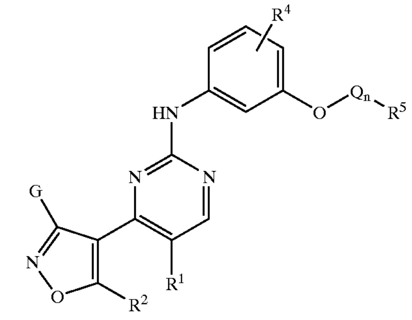
| No. | $R^1$ | 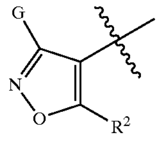 | 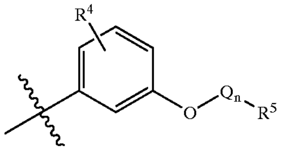 |
|---|---|---|---|
| IIIa-33 | CN | 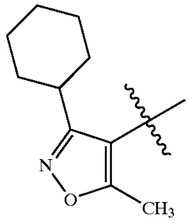 | 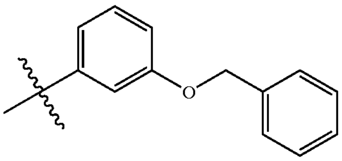 |
| IIIa-34 | H | 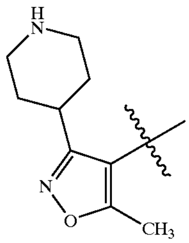 | 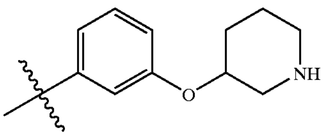 |
| IIIa-35 | H | 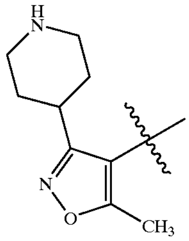 | 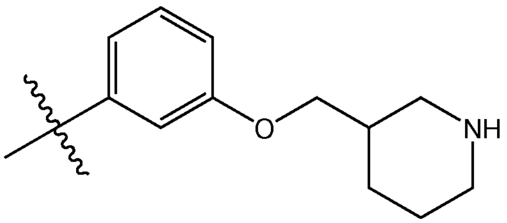 |
| IIIa-36 | $CH_3$ | 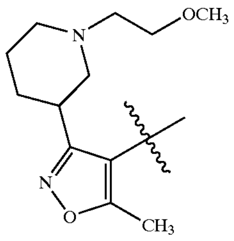 | 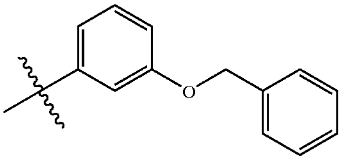 |

TABLE 2-continued
Compounds of Formula IIIa
IIIa
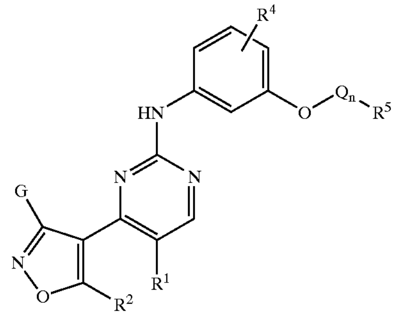
| No. | $R^1$ | 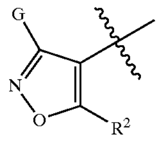 | 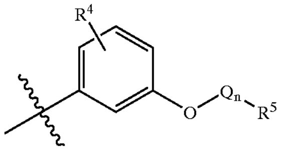 |
|---|---|---|---|
| IIIa-37 | $CH_3$ | 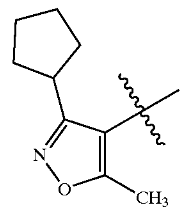 | 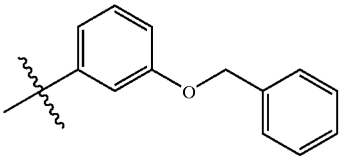 |
| IIIa-38 | $CH_3$ | 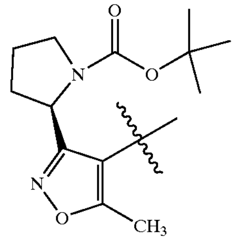 | 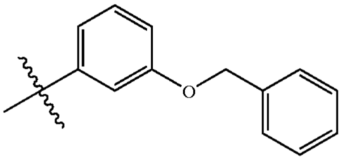 |
| IIIa-39 | $CH_3$ | 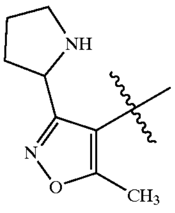 | 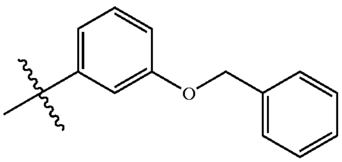 |
| IIIa-40 | 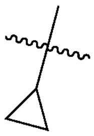 | 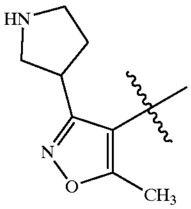 | 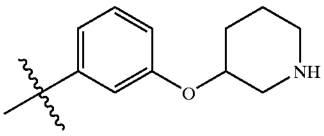 |

TABLE 2-continued
Compounds of Formula IIIa
IIIa
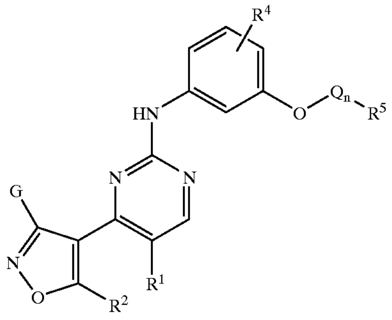
| No. | $R^1$ | 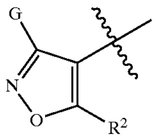 | 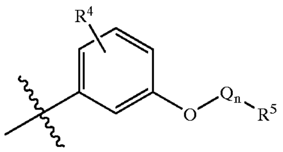 |
|---|---|---|---|
| IIIa-41 | OH | 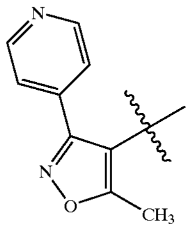 | 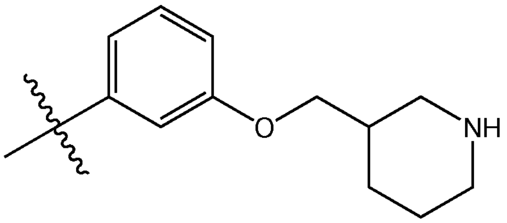 |
| IIIa-42 | $CH_3$ | 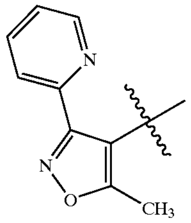 | 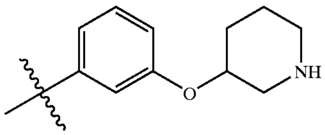 |
| IIIa-43 | H | 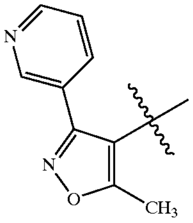 | 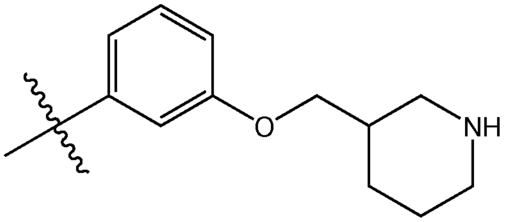 |

TABLE 2-continued
Compounds of Formula IIIa
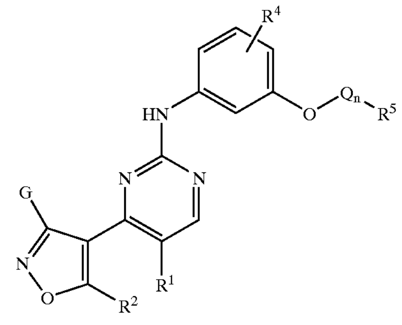
IIIa
| No. | $R^1$ | 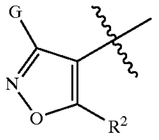 | 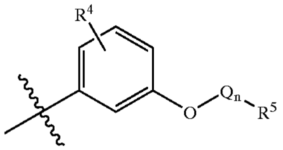 |
|---|---|---|---|
| IIIa-44 | H | 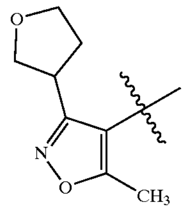 | 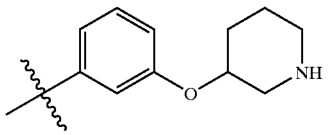 |
| IIIa-45 | H | 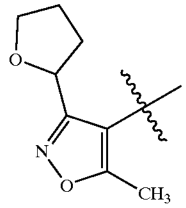 | 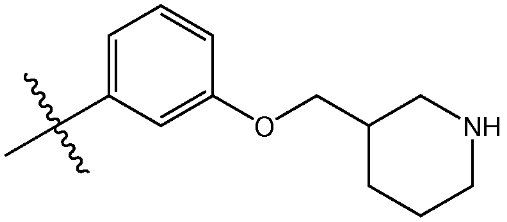 |
| IIIa-46 | H | 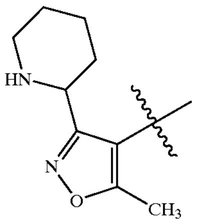 | 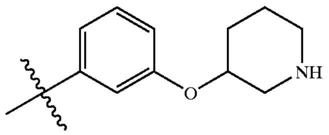 |

13. A compound selected from the following Table 3 compounds:
TABLE 3
Compounds of Formula IIIb
IIIb
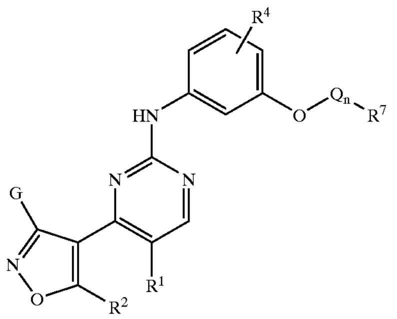
| No. | $R^1$ | 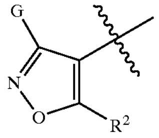 | 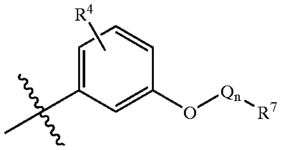 |
|---|---|---|---|
| IIIb-1 | $CH_3$ | 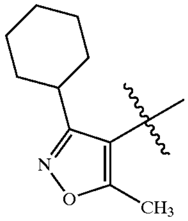 | 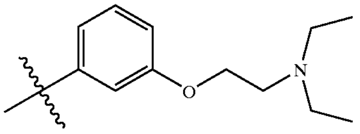 |
| IIIb-2 | $CH_3$ | 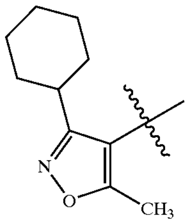 | 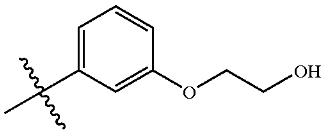 |
| IIIb-3 | $CH_2CH_3$ | 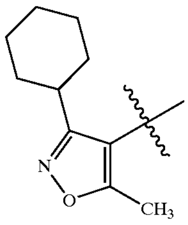 | 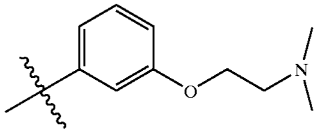 |
| IIIb-4 | $CH_2OH$ | 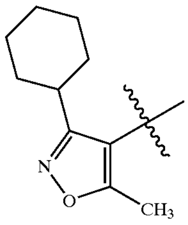 | 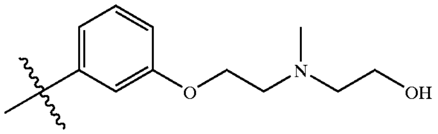 |

TABLE 3-continued
Compounds of Formula IIIb
IIIb
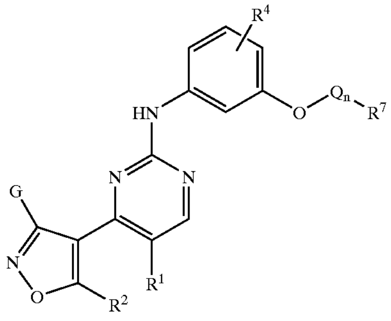
| No. | $R^1$ | 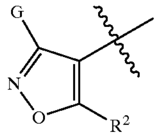 | 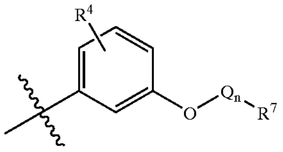 |
|---|---|---|---|
| IIIb-5 | $CH_3$ | 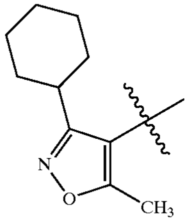 | 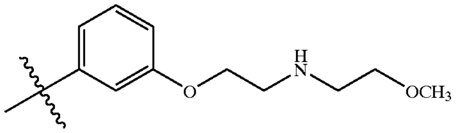 |
| IIIb-6 | $CH_2CN$ | 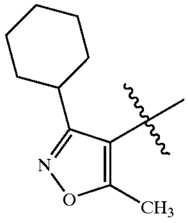 | 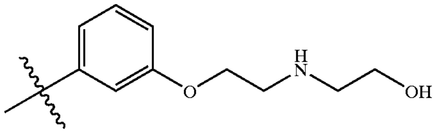 |
| IIIb-7 | $CH_2OH$ | 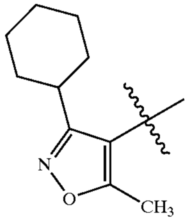 | 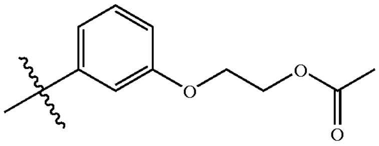 |
| IIIb-8 | $CH_3$ | 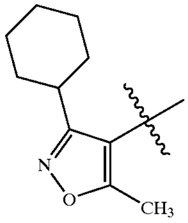 | 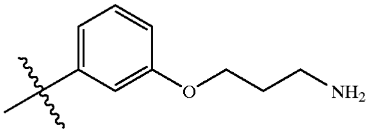 |

TABLE 3-continued
Compounds of Formula IIIb
IIIb
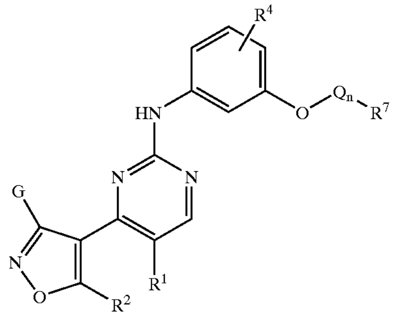
| No. | $R^1$ | 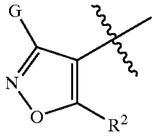 | 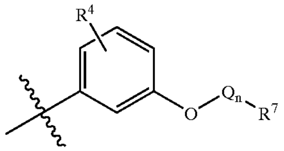 |
|---|---|---|---|
| IIIb-9 | $CH_3$ | 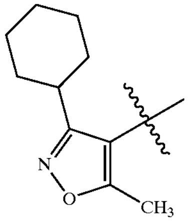 | 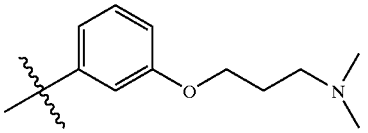 |
| IIIb-10 | $CH_2OH$ | 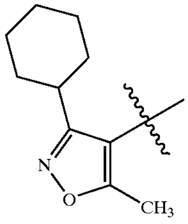 | 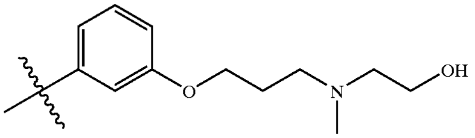 |
| IIIb-11 | $CH_3$ | 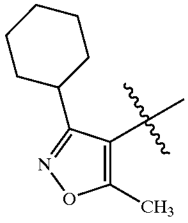 | 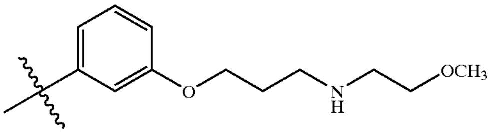 |
| IIIb-12 | $CH_2CH_3$ | 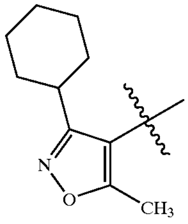 | 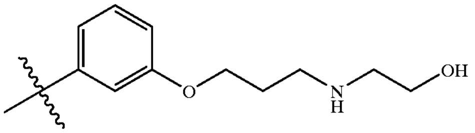 |

TABLE 3-continued
Compounds of Formula IIIb
IIIb
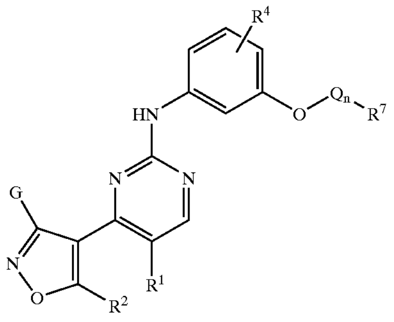
| No. | $R^1$ | 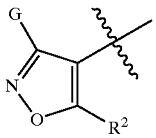 | 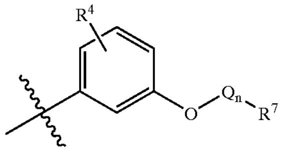 |
|---|---|---|---|
| IIIb-13 | $CH_3$ | 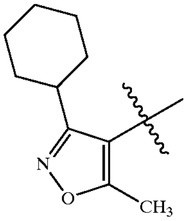 | 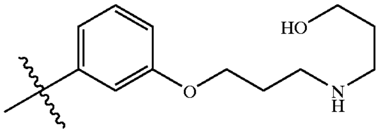 |
| IIIb-14 | $CH_3$ | 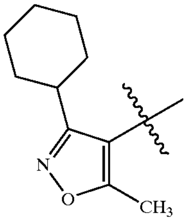 | 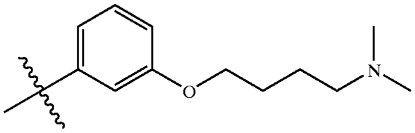 |
| IIIb-15 | $CH_3$ | 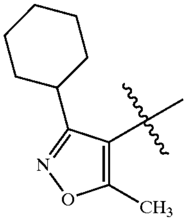 | 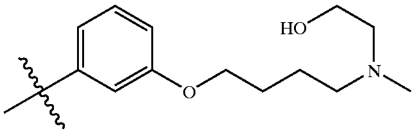 |
| IIIb-16 | $CH_3$ | 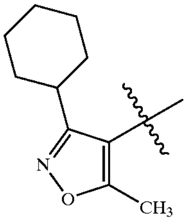 | 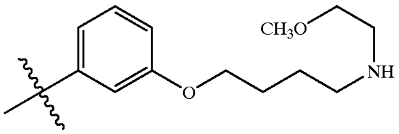 |

TABLE 3-continued
Compounds of Formula IIIb
IIIb
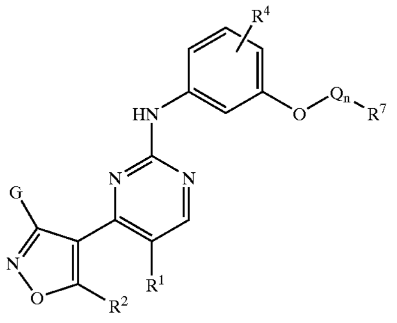
| No. | $R^1$ | 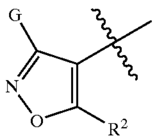 | 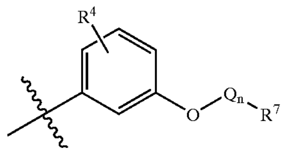 |
|---|---|---|---|
| IIIb-17 | $CH_3$ | 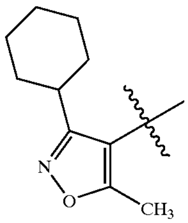 | 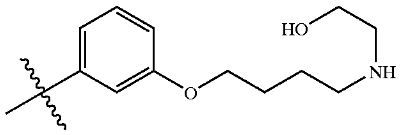 |
| IIIb-18 | $CH_2OH$ | 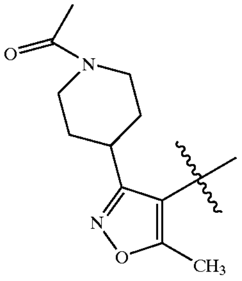 | 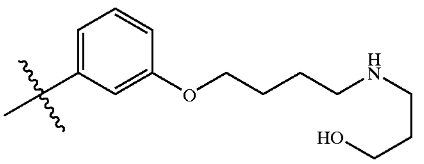 |
| IIIb-19 | $CH_2OH$ | 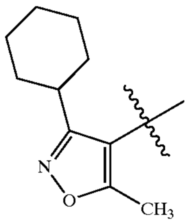 | 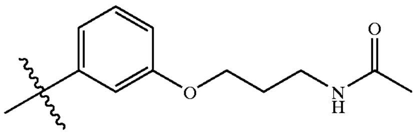 |
| IIIb-20 | $CH_2OH$ | 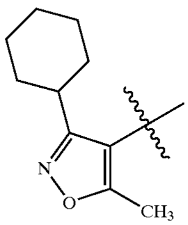 | 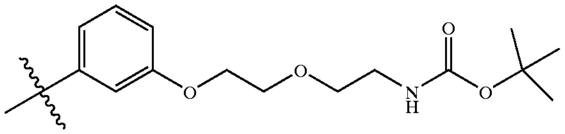 |

TABLE 3-continued
Compounds of Formula IIIb
IIIb
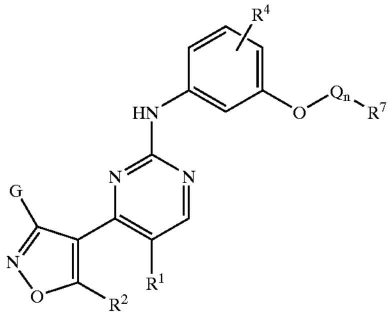
| No. | $R^1$ | 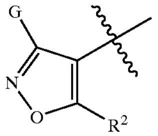 | 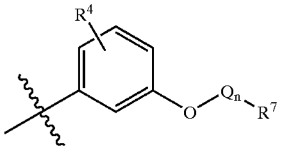 |
|---|---|---|---|
| IIIb-21 | $CH_2OH$ | 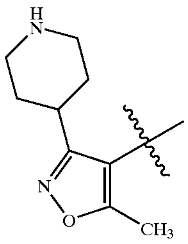 | 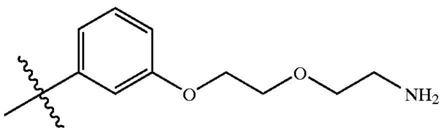 |
| IIIb-22 | $CH_3$ | 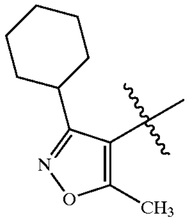 | 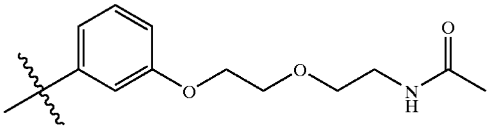 |
| IIIb-23 | $CO_2CH_3$ | 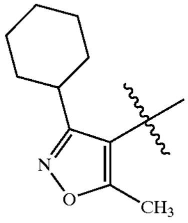 | 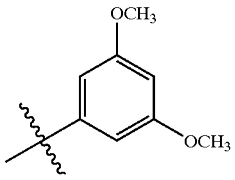 |

TABLE 3-continued
Compounds of Formula IIIb
IIIb
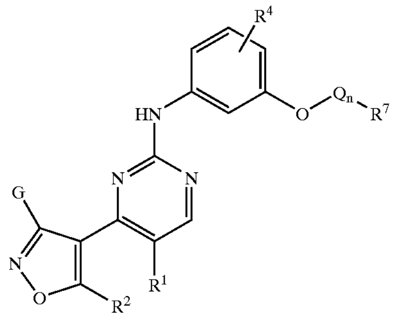
| No. | $R^1$ | 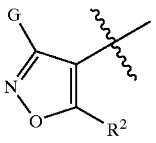 | 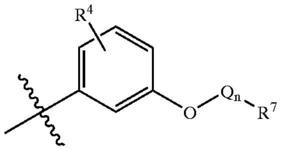 |
|---|---|---|---|
| IIIb-24 | $CO_2H$ | 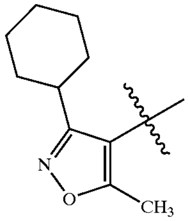 | 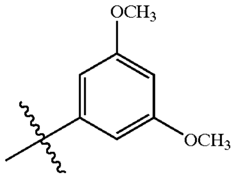 |
| IIIb-25 | $CH_2OH$ | 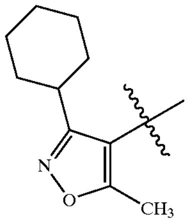 | 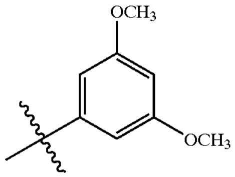 |
| IIIb-26 | $C(O)NH_2$ | 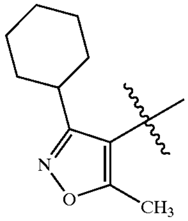 | 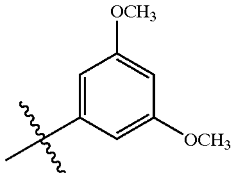 |

TABLE 3-continued
Compounds of Formula IIIb
IIIb
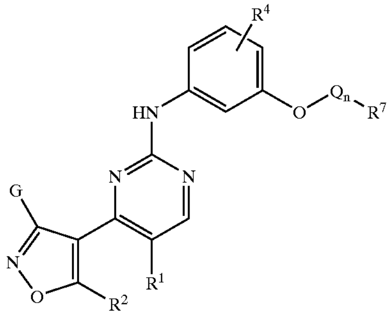
| No. | $R^1$ | 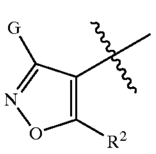 | 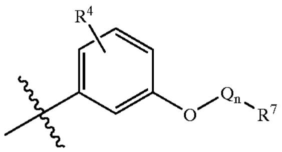 |
|---|---|---|---|
| IIIb-27 | CN | 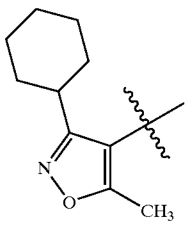 | 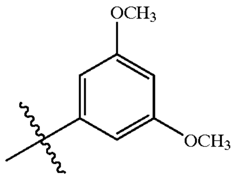 |
| IIIb-28 | $CH_3$ | 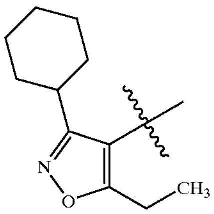 | 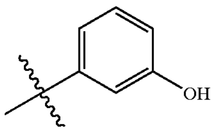 |
| IIIb-29 | $CH_2OCH_2CH_2CH_3$ | 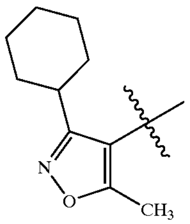 | 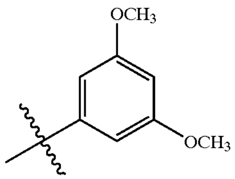 |

14. A compound selected from the following Table 4 compounds:
TABLE 4
Compounds of Formula IVa
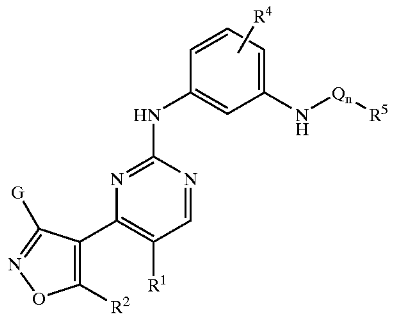
IVa
| No. | $R^1$ | 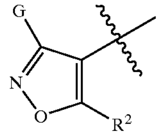 | 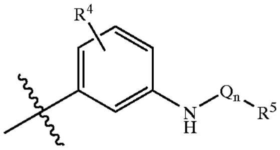 |
|---|---|---|---|
| IVa-1 | H | 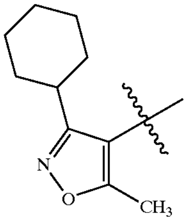 | 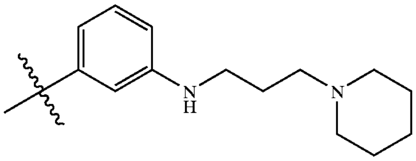 |
| IVa-2 | H | 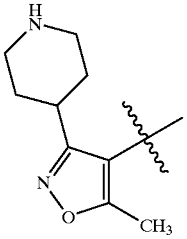 | 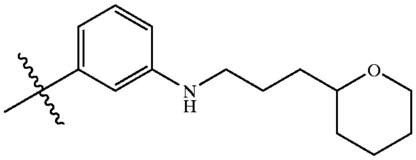 |
| IVa-3 | H | 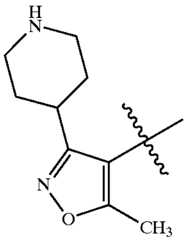 | 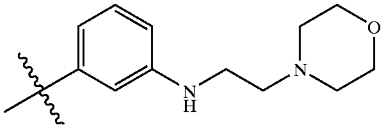 |
| IVa-4 | H | 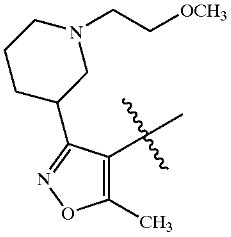 | 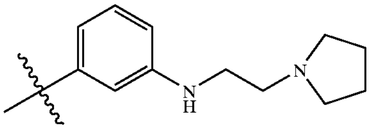 |

TABLE 4-continued
Compounds of Formula IVa
IVa
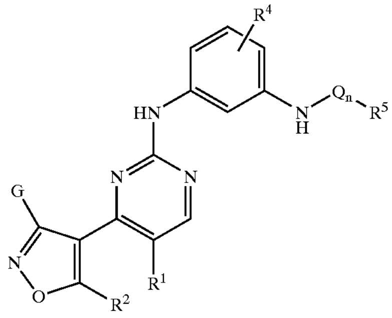
| No. | $R^1$ | 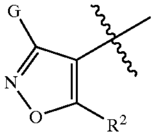 | 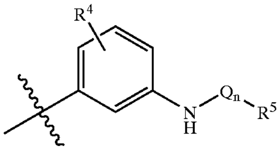 |
|---|---|---|---|
| IVa-5 | $CH_3$ | 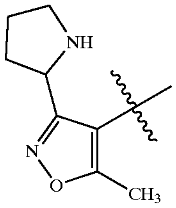 | 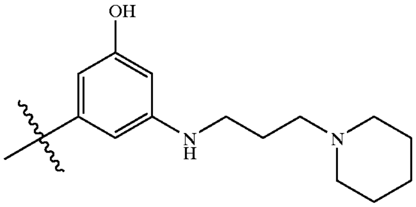 |
| IVa-6 | $CH_3$ | 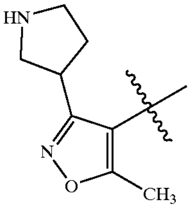 | 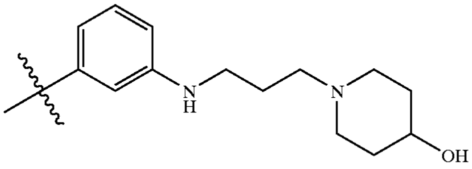 |
| IVa-7 | $CH_3$ | 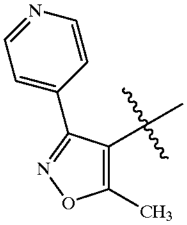 | 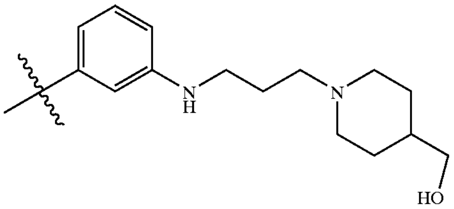 |
| IVa-8 | $CH_3$ | 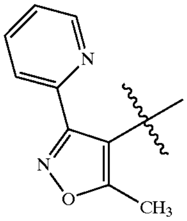 | 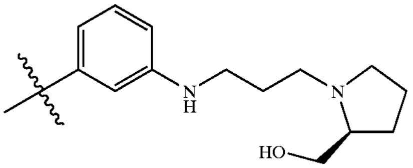 |

TABLE 4-continued
Compounds of Formula IVa
IVa
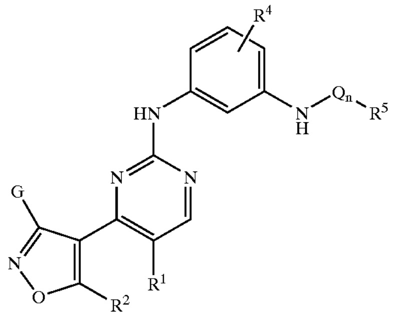
| No. | $R^1$ | 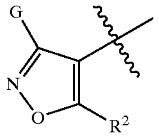 | 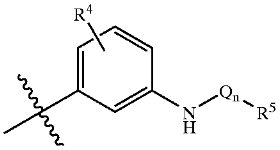 |
|---|---|---|---|
| IVa-9 | H | 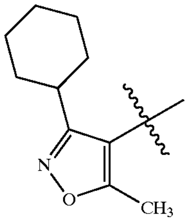 | 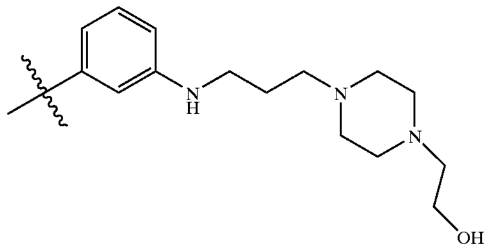 |
| IVa-10 | H | 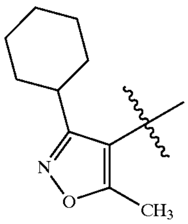 | 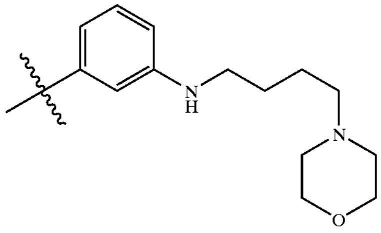 |
| IVa-11 | H | 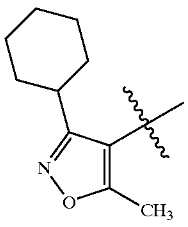 | 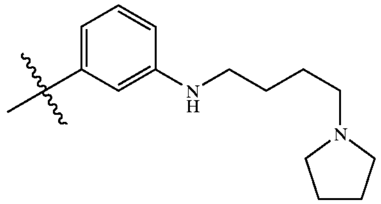 |
| IVa-12 | H | 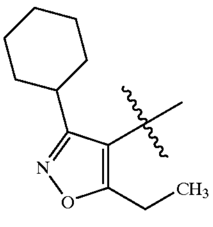 | 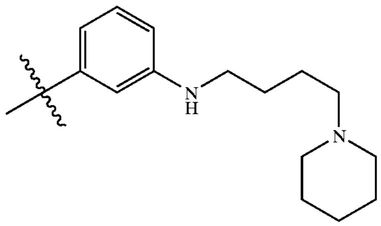 |

TABLE 4-continued
Compounds of Formula IVa
IVa
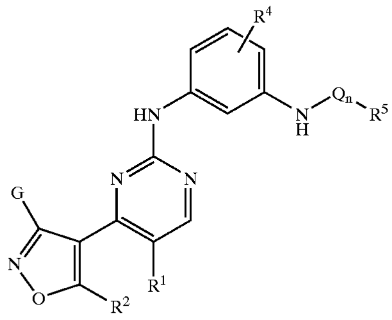
| No. | $R^1$ | 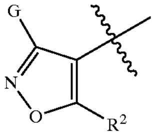 | 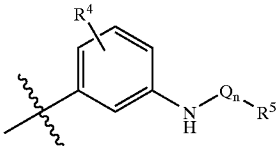 |
|---|---|---|---|
| IVa-13 | $CH_3$ | 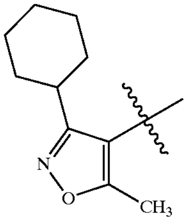 | 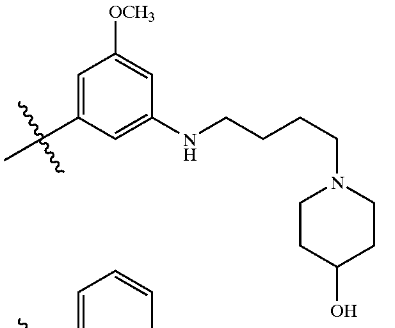 |
| IVa-14 | $CH_3$ | 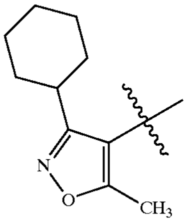 | 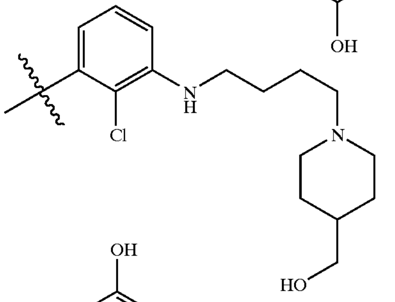 |
| IVa-15 | $CH_3$ | 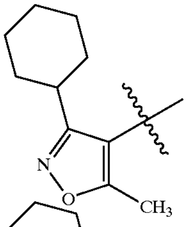 | 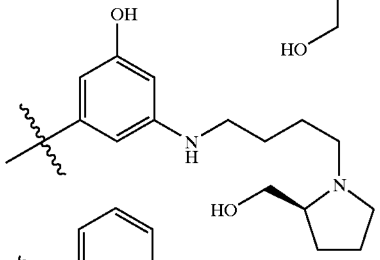 |
| IVa-16 | $CH_3$ | 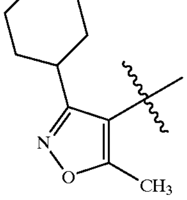 | 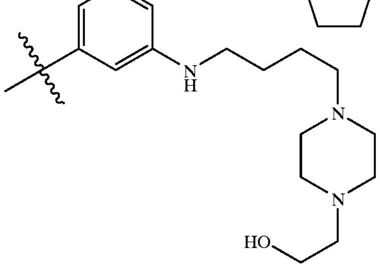 |

15. A compound selected from the following Table 5 compounds:
TABLE 5
Compounds of Formula IVb
IVb
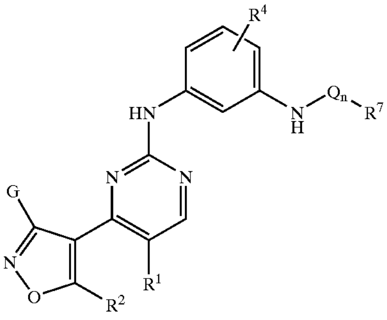
| No. | $R^1$ | 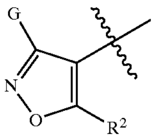 | 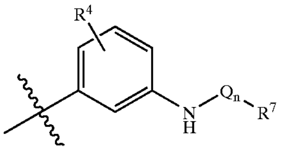 |
|---|---|---|---|
| IVb-1 | $CH_3$ | 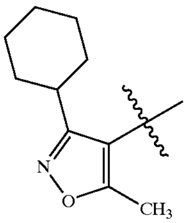 | 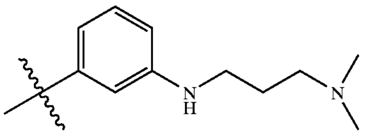 |
| IVb-2 | $CH_2CH_3$ | 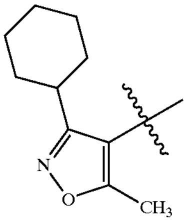 | 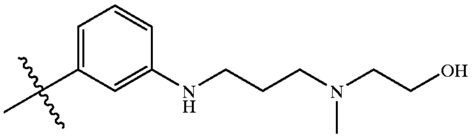 |
| IVb-3 | $CH_3$ | 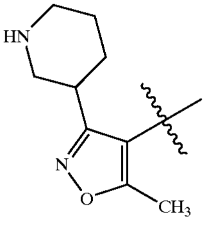 | 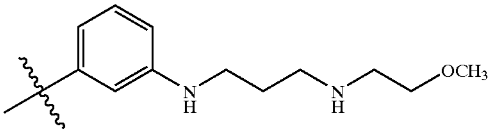 |

TABLE 5-continued
Compounds of Formula IVb
IVb
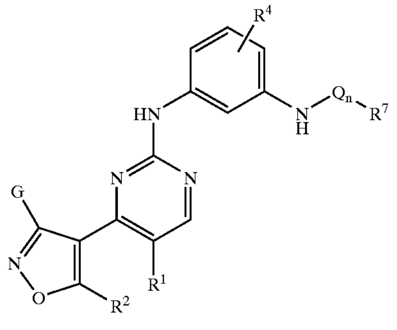
| No. | $R^1$ | 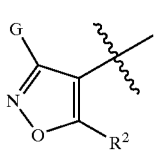 | 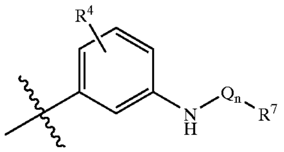 |
|---|---|---|---|
| IVb-4 | $CH_2OH$ | 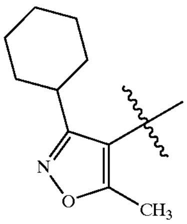 | 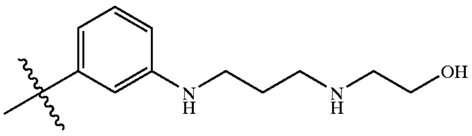 |
| IVb-5 | OH | 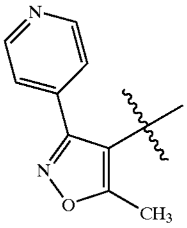 | 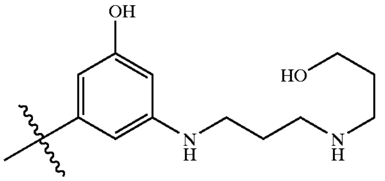 |
| IVb-6 | $CH_2CH_3$ | 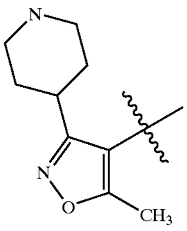 | 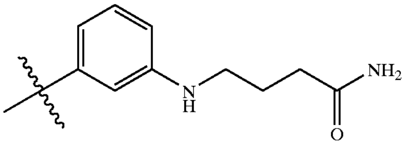 |

TABLE 5-continued
Compounds of Formula IVb
IVb
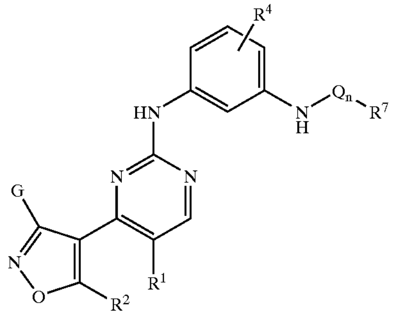
| No. | $R^1$ | 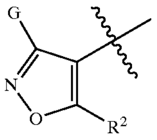 | 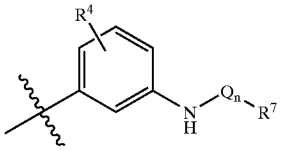 |
|---|---|---|---|
| IVb-7 | $CH_2CN$ | 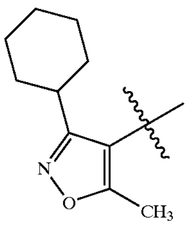 | 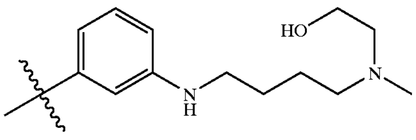 |
| IVb-8 | 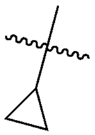 | 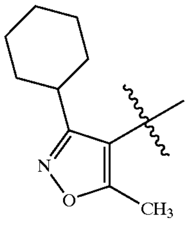 | 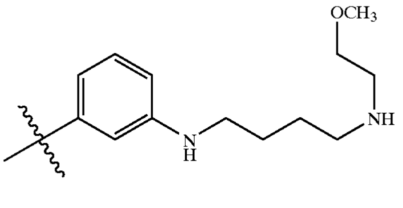 |
| IVb-9 | $NH_2$ | 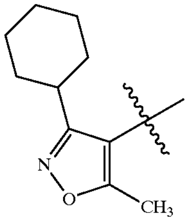 | 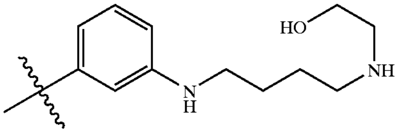 |

16. A compound selected from the following Table 6 compounds:
TABLE 6
Compounds of Formula Va
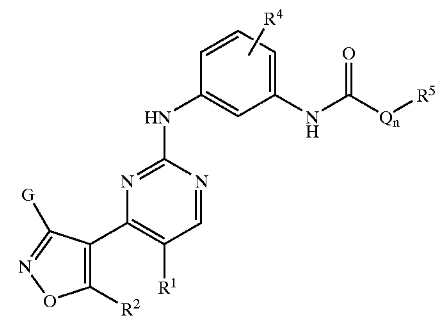
Va
| No. | $R^1$ | 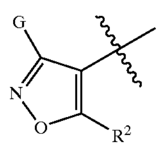 | 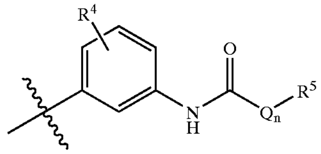 |
|---|---|---|---|
| Va-1 | H | 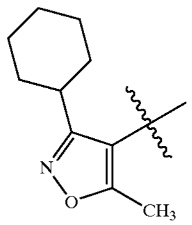 | 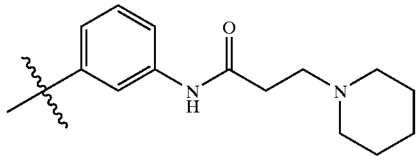 |
| Va-2 | H | 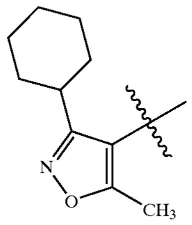 | 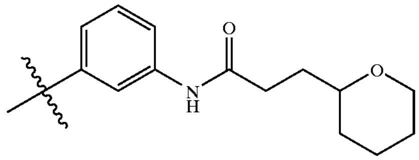 |
| Va-3 | H | 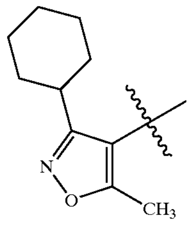 | 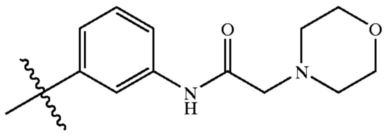 |
| Va-4 | $CH_3$ | 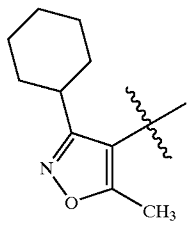 | 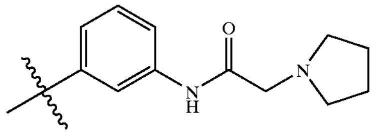 |

TABLE 6-continued
Compounds of Formula Va
Va
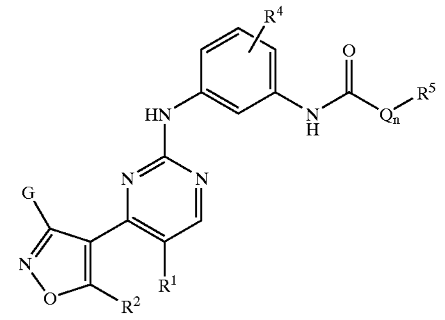
| No. | $R^1$ | 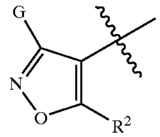 | 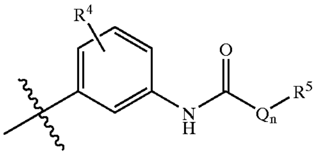 |
|---|---|---|---|
| Va-5 | H | 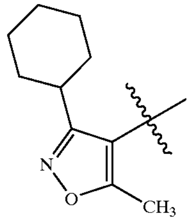 | 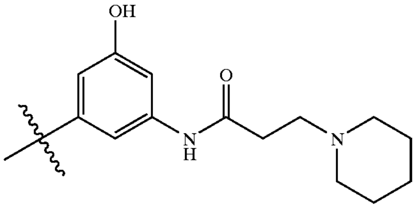 |
| Va-6 | H | 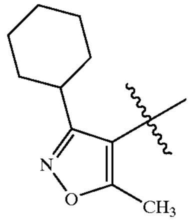 | 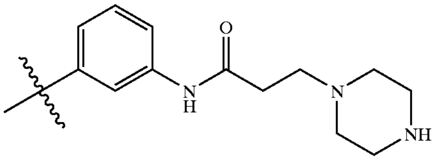 |
| Va-7 | $CH_2CH_3$ | 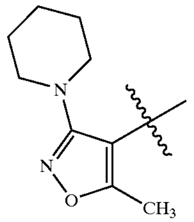 | 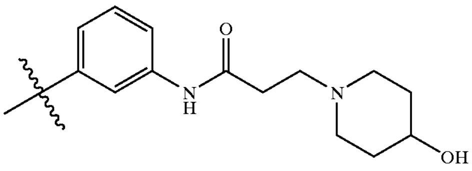 |
| Va-8 | $CH_2CN$ | 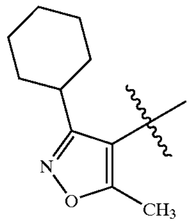 | 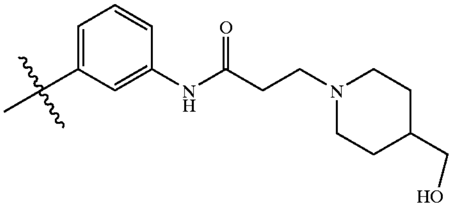 |

TABLE 6-continued
Compounds of Formula Va
Va
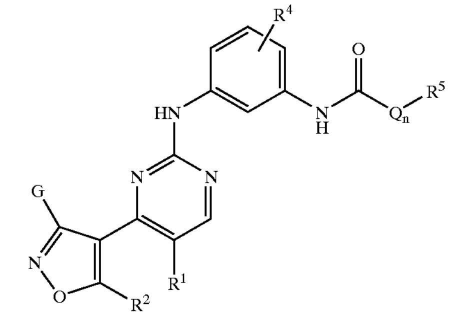
| No. | $R^1$ | 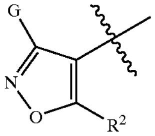 | 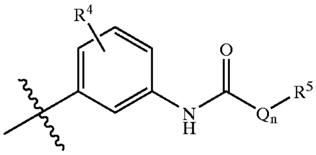 |
|---|---|---|---|
| Va-9 | $CH_2OH$ | 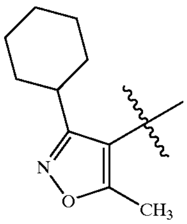 | 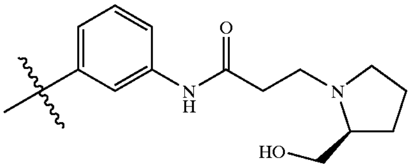 |
| Va-10 | H | 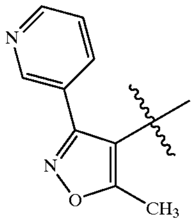 | 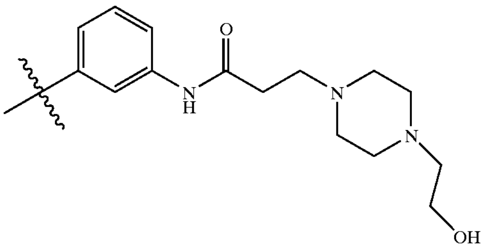 |
| Va-11 | H | 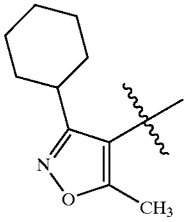 | 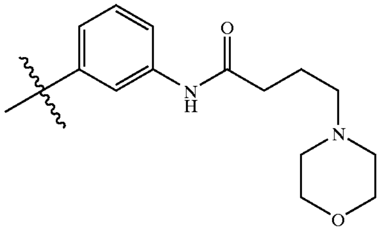 |

TABLE 6-continued
Compounds of Formula Va
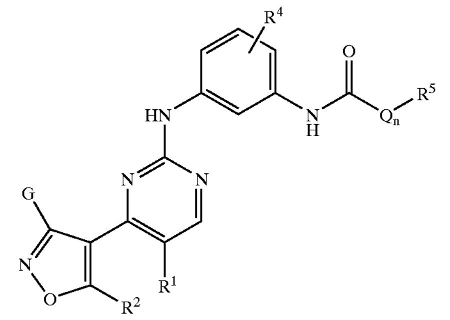
Va
| No. | $R^1$ | 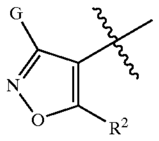 | 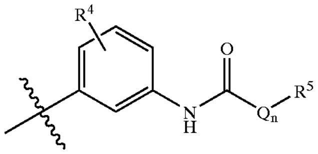 |
|---|---|---|---|
| Va-12 | H | 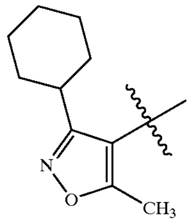 | 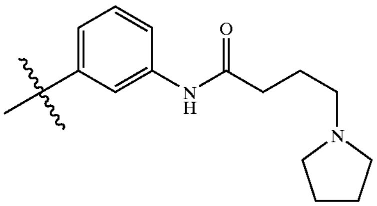 |
| Va-13 | $CH_3$ | 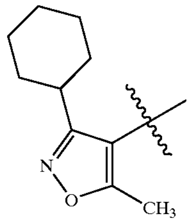 | 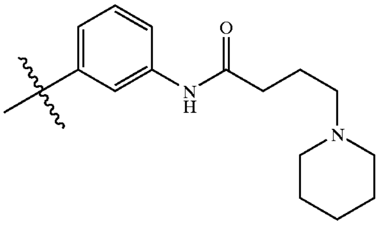 |
| Va-14 | OH | 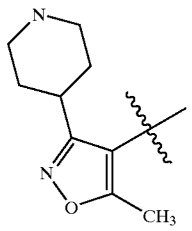 | 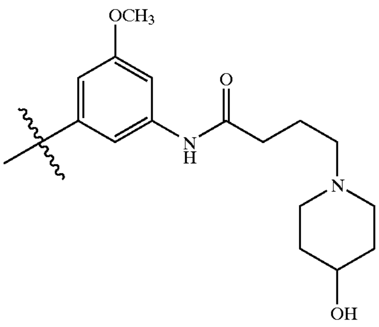 |

TABLE 6-continued
Compounds of Formula Va
Va
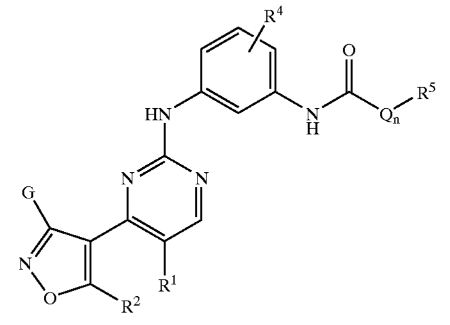
| No. | $R^1$ | 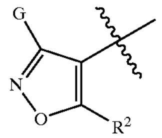 | 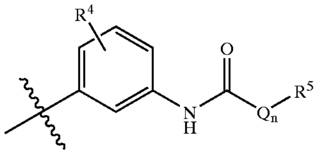 |
|---|---|---|---|
| Va-15 | H | 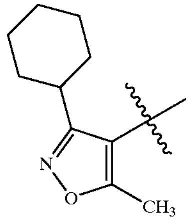 | 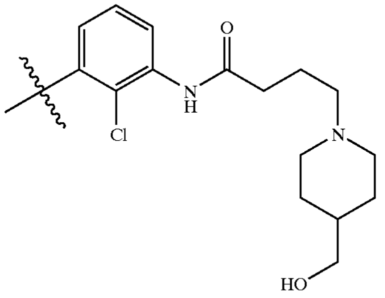 |
| Va-16 | $NH_2$ | 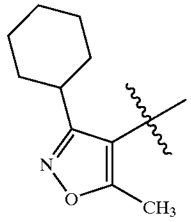 | 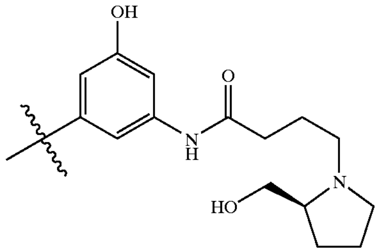 |
| Va-17 | H | 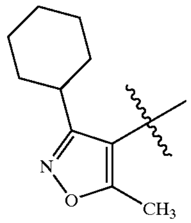 | 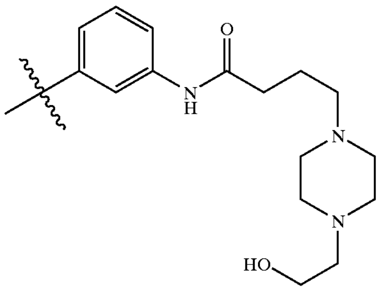 |

17. A compound selected from the following Table 7 compounds:
TABLE 7
Compounds of Formula Vb
Vb
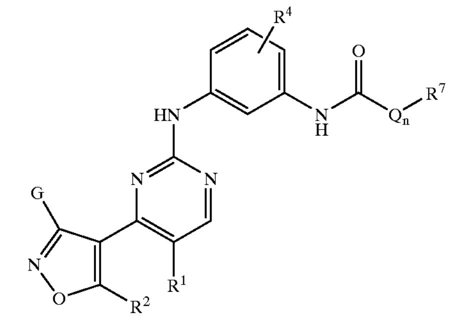
| No. | $R^1$ | 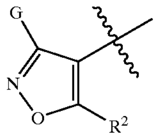 | 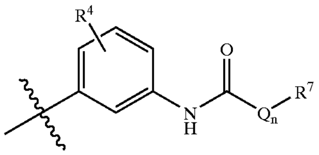 |
|---|---|---|---|
| Vb-1 | $CH_3$ | 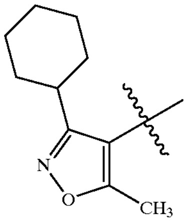 | 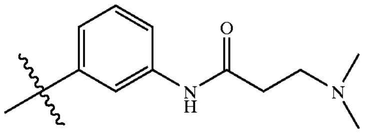 |
| Vb-2 | $CH_2CH_3$ | 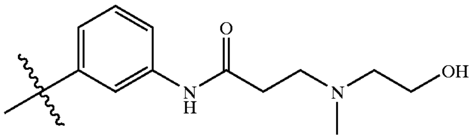 | |
| Vb-3 | $CH_3$ | 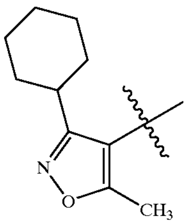 | 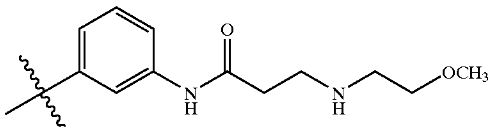 |
| Vb-4 | $CH_2OH$ | 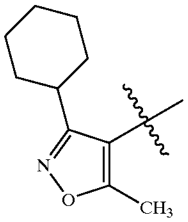 | 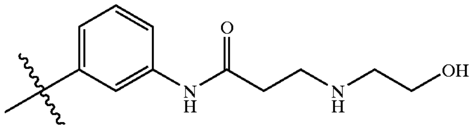 |

TABLE 7-continued
Compounds of Formula Vb
Vb
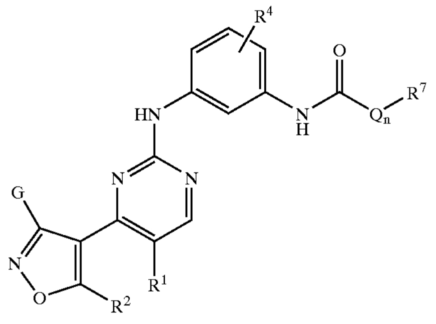
| No. | $R^1$ | 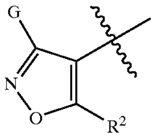 | 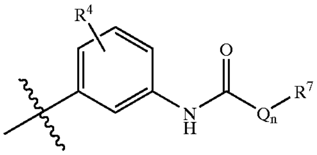 |
|---|---|---|---|
| Vb-5 | OH | 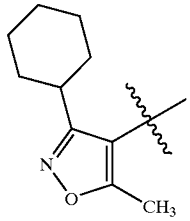 | 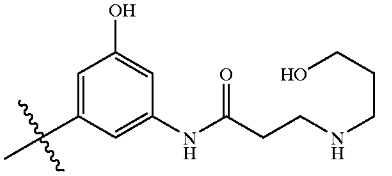 |
| Vb-6 | $CH_2CH_3$ | 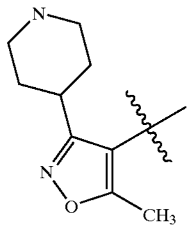 | 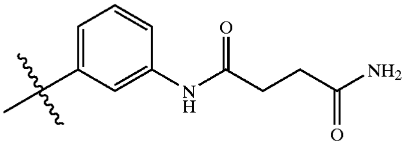 |
| Vb-7 | $CH_2CN$ | 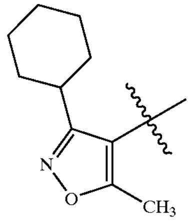 | 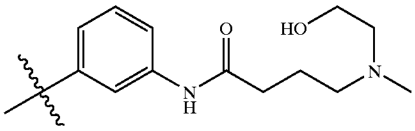 |
| Vb-8 | $CH_2OH$ | 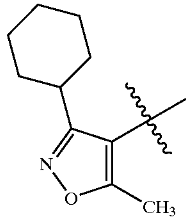 | 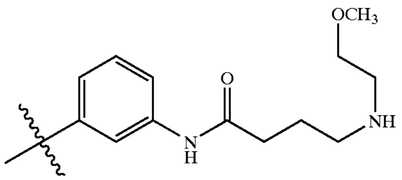 |

TABLE 7-continued
Compounds of Formula Vb
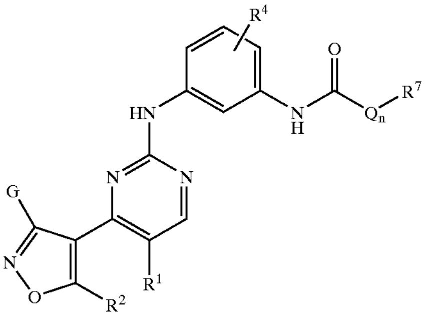
Vb
| No. | $R^1$ | 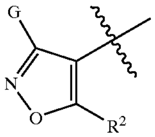 | 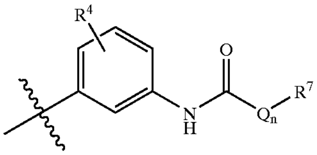 |
|---|---|---|---|
| Vb-9 | $NH_2$ | 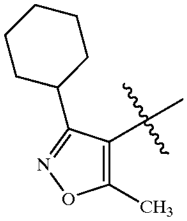 | 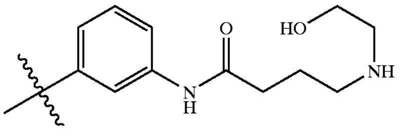 |
| Vb-10 | $CH_2CN$ | 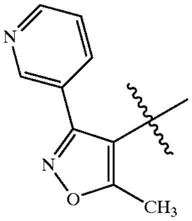 | 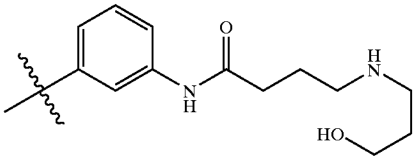 |
| Vb-11 | $CH_2OH$ | 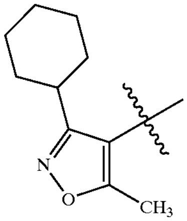 | 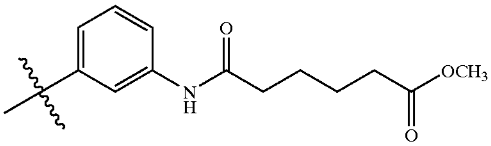 |
| Vb-12 | $NH_2$ | 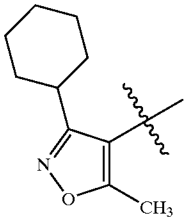 | 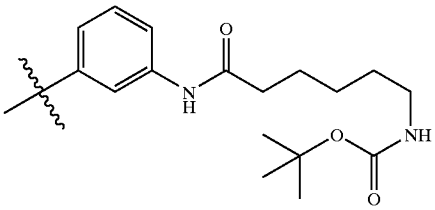 |

TABLE 7-continued
Compounds of Formula Vb
Vb
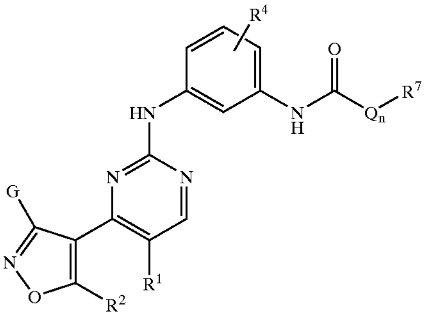
| No. | $R^1$ | 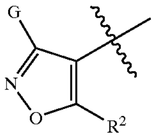 | 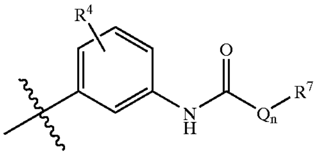 |
|---|---|---|---|
| Vb-13 | $CH_2OH$ | 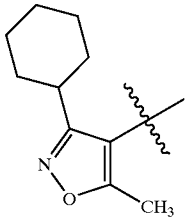 | 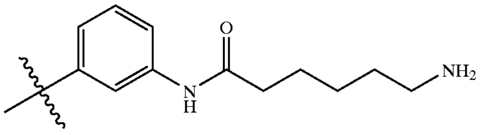 |
| Vb-14 | $CH_3$ | 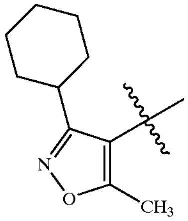 | 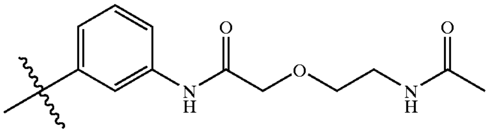 |
| Vb-15 | $CH_2CH_3$ | 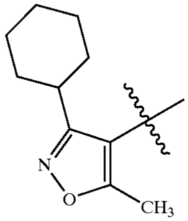 | 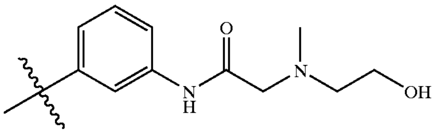 |
| Vb-16 | $CH_3$ | 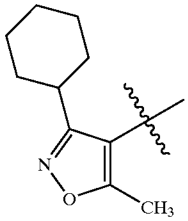 | 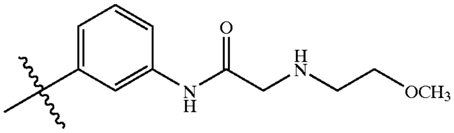 |

TABLE 7-continued
Compounds of Formula Vb
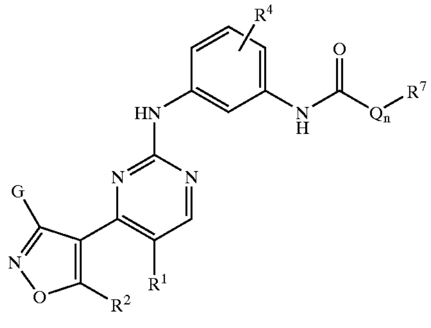
Vb
| No. | $R^1$ | 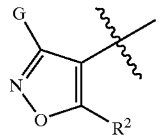 | 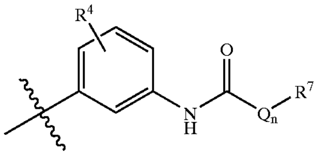 |
|---|---|---|---|
| Vb-17 | $CH_2OH$ | 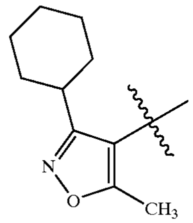 | 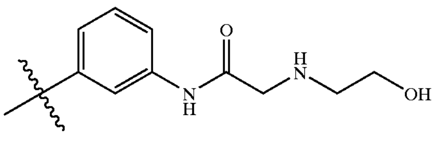 |
| Vb-18 | $OCH_3$ | 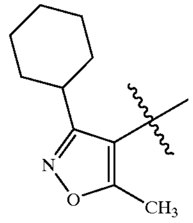 | 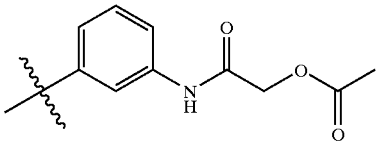 |
| Vb-19 | $CH_2OCH_3$ | 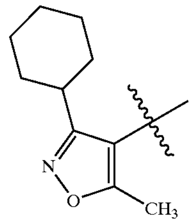 | 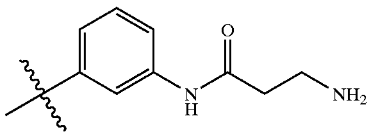 |
| Vb-20 | $CH_3$ | 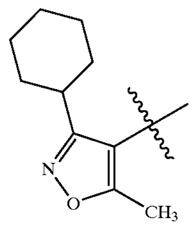 | 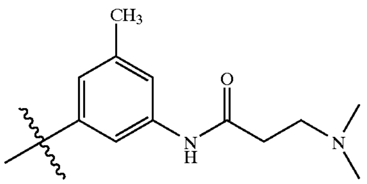 |

TABLE 7-continued
Compounds of Formula Vb
Vb
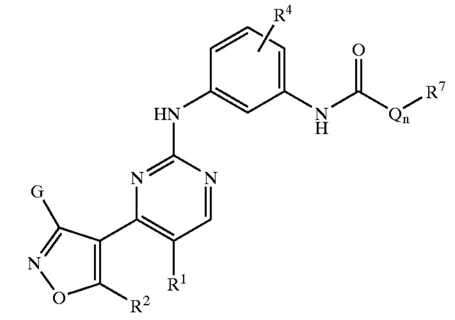
| No. | $R^1$ | 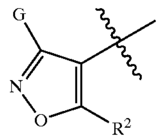 | 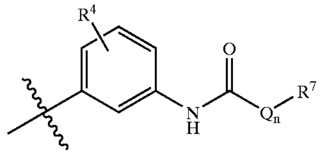 |
|---|---|---|---|
| Vb-21 | $CH_2CH_3$ | 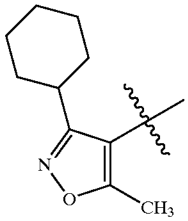 | 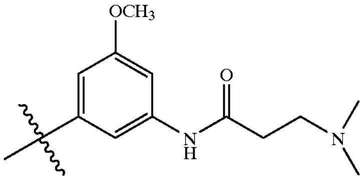 |
| Vb-22 | $CH_2OH$ | 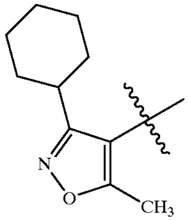 | 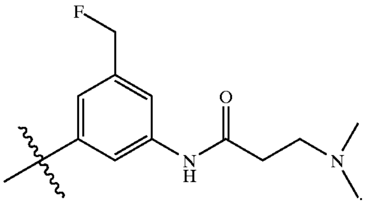 |
* * * * *